(12) United States Patent
Long et al.

(10) Patent No.: US 9,260,462 B2
(45) Date of Patent: *Feb. 16, 2016

(54) METHODS FOR SYNTHESIZING MOLYBDOPTERIN PRECURSOR Z DERIVATIVES

(75) Inventors: Xiangtian Long, Guangzhou (CN); Danmei Dai, Chongqin (CN); Andreas Brunner, Brig (CH); Derek Kevin Watt, Lower Hutt (NZ); Keith Clinch, Lower Hutt (NZ); Sylvia Myrna Baars, Hamilton (NZ); Rachel Anne Dixon, Wellington (NZ); Gillian Mary Little, Essex (GB); Cyrille Abel Sébastien Landreau, Essex (GB); Nicolas Georges Rene Proisy, Hertfordshire (GB)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/000,055

(22) PCT Filed: Feb. 17, 2012

(86) PCT No.: PCT/US2012/025689
§ 371 (c)(1),
(2), (4) Date: Mar. 24, 2014

(87) PCT Pub. No.: WO2012/112922
PCT Pub. Date: Aug. 23, 2012

(65) Prior Publication Data
US 2014/0323726 A1    Oct. 30, 2014

Related U.S. Application Data

(60) Provisional application No. 61/498,801, filed on Jun. 20, 2011, provisional application No. 61/444,389, filed on Feb. 18, 2011, provisional application No. 61/444,280, filed on Feb. 18, 2011, provisional application No. 61/444,399, filed on Feb. 18, 2011, provisional application No. 61/498,808, filed on Jun. 20, 2011, provisional application No. 61/599,314, filed on Feb. 15, 2012.

(51) Int. Cl.
*C07D 491/22* (2006.01)
*C07F 9/6574* (2006.01)
*C07D 491/14* (2006.01)
*C07D 491/147* (2006.01)

(52) U.S. Cl.
CPC .......... *C07F 9/65744* (2013.01); *C07D 491/14* (2013.01); *C07D 491/147* (2013.01)

(58) Field of Classification Search
CPC ..................... C07D 491/147; C07D 491/22
See application file for complete search history.

(56) References Cited

U.S. PATENT DOCUMENTS

| | | | |
|---|---|---|---|
| 4,522,811 A | 6/1985 | Eppstein et al. |
| 7,504,095 B2 | 3/2009 | Schwarz et al. |
| 7,888,506 B2 | 2/2011 | Basu et al. |
| 2003/0207430 A1 | 11/2003 | Tang et al. |
| 2004/0067554 A1 | 4/2004 | Lagace et al. |
| 2007/0037250 A1 | 2/2007 | Schwarz et al. |
| 2011/0009629 A1 | 1/2011 | Albert et al. |
| 2014/0303367 A1 | 10/2014 | Long et al. |

FOREIGN PATENT DOCUMENTS

| | | |
|---|---|---|
| EP | 0191335 | 8/1986 |
| WO | WO 02/00196 | 1/2002 |
| WO | WO 2007/052308 | 5/2007 |
| WO | WO 2008/089008 | 7/2008 |
| WO | WO 2009/088979 | 7/2009 |
| WO | WO2012112922 A1 | 8/2012 |

OTHER PUBLICATIONS

1Vigor.com. "Glucose is the Primary Source of Energy for Cells." © 2014. Available from: < http://www.1vigor.com/article/glucose-natural-food-sources/ >, pp. 1-5.*
Livestrong.com. "Foods with Mannose." © 2014. Available from: < http://www.livestrong.com/article/142964-foods-with-mannose/ >, pp. 1-4.*
Atherton et al., "The Fluorenylmethoxycarbonyl Amino Protecting Group," in The Peptides, S. Udenfriend and J. Meienhofer, Eds., Academic Press, New York, 1987, vol. 9, Chpt. 1, p. 1.
Béres et al., "Synthesis and antitumor and antiviral properties of 5-halo- and 5-(trifluoromethyl)-2'-deoxyuridine 3',5'-cyclic monophosphates and neutral triesters," *J Med Chem.*, 29(7):1243-1249, Jul. 1986.
Blom et al., "Preparative LC-MS purification: improved compound-specific method optimization," *J Comb Chem.*, 6(6):874-883, Nov.-Dec. 2004.
Bradshaw and Dinsmore, "Synthesis of a cobalt complex of a pyrano[2,3-b]quinoxaline-3,4-dithiolate related to molybdopterin," *Chem. Commun.*, 417-418, 1998.
Bradshaw et al., "Stable pyrano[2,3-b]quinoxalines and pyrano[2,3-g]pteridines related to molybdopterin," *Chem. Commun.*, 123-124, 2001.
Bradshaw et al., "Synthesis of the organic ligand of the molybdenum cofactor, in protected form," *J. Chem. Soc., Perkin Trans. 1*, 3239-3244, 2001.
Bradshaw et al., "The synthesis of pyrano[2,3-b]quinoxalines related to molybdopterin," *J. Chem. Soc., Perkin Trans. 1*, pp. 3232-3238, 2001.
Cordonniera, "Experimental and computational investigation of the unexpected formation of β-substituted polyoxygenated furans from conveniently functionalized carbohydrates," *Tetrahedron*, 66(3):736-742, Jan. 16, 2010.

(Continued)

*Primary Examiner* — Noble Jarrell
*Assistant Examiner* — John S Kenyon
(74) *Attorney, Agent, or Firm* — Fish & Richardson P.C.

(57) ABSTRACT

Provided herein are synthetic methods for preparing a compound of formula (I): Also provided herein are synthetic methods for preparing a compound of formula (XIII): The disclosure also provides useful intermediates, derivatives, prodrugs, and pharmaceutically acceptable salts, solvates and hydrates of the formula (I) and formula (XIII) compounds. These compounds are useful for treating diseases associated with molybdenum cofactor deficiency.

48 Claims, 3 Drawing Sheets

(56) References Cited

OTHER PUBLICATIONS

Corey et al., "A key intermediate for the synthesis of maytansine and related antitumor agents," *Tetrahedron Lett.*, 19(12):1051-1054, 1978.
Eberlein et al., "The interconversion of the 5,6,7,8-tetrahydro-, 6,7,8-dihydro-, and radical forms of 6,6,7,7-tetramethyldihydropterin. A model for the biopterin center of aromatic amino acid mixed function oxidases," *J Am Chem Soc*, 106(25): 7916-7924, 1984.
Evans, "Asymmetric synthesis of calyculin A. 3. Assemblage of the calyculin skeleton and the introduction of a new phosphate monoester synthesis," *J. Org. Chem.*, 57(7): 1964-1966, 1992.
Fugedi, "Oligosaccharide Synthesis," *The Organic Chemistry of Sugars*, Taylor & Francis, 2006, Chpt. 5, p. 181.
Fun et al., "6-Amino-2,5-bis (pivaloylamino)pyrimidin-4(3H)-one dehydrate," *Acta Crystallogr Sect E Struct Rep Online.*, 65(Pt 7):o1484-o1485, Jun. 6, 2009.
Genieser et al., "Synthesis of the 3',5'-Cyclic Phosphates from Unprotected Nucleosides," Synthesis 1989; 1989(1): 53-54, 1989.
Goswami and Adak "A novel one-pot two-component synthesis of tricyclic pyrano[2,3-b]quinoxalines," *Tetrahedron Lett.*, 46(2):221-224, Jan. 10, 2005.
Greatbanks et al., "The relative stabilities of dihydropterins; a comment on the structure of Moco, the cofactor of the oxomolybdoenzymes," *J. Chem. Soc., Perkin Trans. 2*, 1529-1534, 1997.
Guillory, "Generation of Polymorphs, Hydrates, Solvates, and Amorphous Solids," Polymorphism in Pharmaceutical Solids, ed. Harry Brittan, vol. 95, Marcel Dekker, Inc., NY, 1999, pp. 202-209.
Guiney et al., "Syntheses of highly functionalised 6-substituted pteridines," *Org Biomol Chem.*, 1(4):664-675, Feb. 21, 2003.
Guschin et al., "New Pyranopterin Chemistry Related to Molybdentum and Tungsten Enzymes," *Chemistry and Biology of Pteridines and Folates*, Proceedings of the 12th International Symposium on Pteridines and Folates, National Institutes of Health, Bethesda, Maryland, Jun. 17-22, 2001, 43-47.
Hanaya, et al. "Efficient total syntheses of natural pterin glycosides: limipterin and tepidopterin," *Tetrahedron*, 64(9): 2090-2100, Feb. 25, 2008.
Hann et al., "1,3-Anhydro-2,4-methylene-D,L-xylitol and related compounds," *J. Am. Chem. Soc.*, 72(1): 561-566, Jan. 1950.
Hirai et al., "Stereocontrolled and convergent entry to CF2-sialosides: synthesis of CF2-linked ganglioside GM4," *J Am Chem Soc.*, 129(50):15420-1541. Epub Nov. 23, 2007.
Ho et al., "Synthesis and biological evaluation of 2-amino-4-hydroxy-6-hydroxymethylpteridine pyrophosphate," *J Pharm Sci.*, 63(9):1472-1476, Sep. 1974.
Imoto et al., "Synthesis, DNA polymerase incorporation, and enzymatic phosphate hydrolysis of formamidopyrimidine nucleoside triphosphates," *J Am Chem Soc.*, 128(45):14606-14611, Nov. 15, 2006.
Liu et al., "Stereoselective synthesis of 2-amino-2-deoxysugars: N-alkyl-D-allosamines.," *Org Biomol Chem.*, 1(10):1641-1642, May 21, 2003.
Liu et al., "Synthesis of Aminosugars Having New Structures from Oxosugars," Acta Chim. Sinica, Huaxue Xuebao, 61(7): 1149-1152, 2003, [English abstract].
López et al., "Synthesis and biological study of 6-polyhydroxyalkylpteridines," *J. Heterocyclic Chem.*, 38(3): 727-736, May/Jun. 2001.
Low et al., "(3R,4S,4aR,10aS)-5,10-Diacetyl-3,4,4a,5,6,7,10,10a-octahydro-8-methoxy-6-oxo-2H-pyrano[3,2-g]pteridin-3,4-diyl diacetate," *Acta Cryst.*, C55:452-454, 1999.
Low et al., "A Triacetyl Derivation of a Pyrano[3,2-g]pteridine," *Acta Cryst.*, C51:2141-2143, 1995.
Lyudnikova et al., "Investigation of the photochemical properties of biopterin and its reduced forms," *Appl. Biochem. Microbiol.* 5(1):104-109, Jan. 2009.
Manthorpe et al., A Scalable Synthesis of a Mycosamine Donor. Overcoming Difficult Reactivity in Allose Systems, *Synthesis*, 2005(19): 3380-3388, Dec. 2005.

Matsuura et al., "Stereochemistry of biopterin cofactor and facile methods for the determination of the stereochemistry of a biologically active 5,6,7,8-tetrahydropterin," *J Biochem.*, 98(5):1341-1348, Nov. 1985.
Mendel and Schwarz, "Biosynthesis and molecular biology of the molybdenum cofactor (Moco)," *Met Ions Biol Syst.*, 39:317-368, 2002.
Murata et al., "A Novel Ring Formation of 1,2-Dihydroquinoxalines," *Heterocycles*, 26(4):883-884, 1987.
Murata et al., "Recent Advances in Selective Syntheses of 6- and 7-Substituted Pteridines," *Heterocycles*, 48(6):1255-1274, 1998.
Murata, S. et al. "Tetrahydrobiopterin and Related Biologically Important Pterins," *Top. Heterocycl. Chem.*, 8:127-171, 2007.
Nieter Burgmayer, "Redox reactions of the pyranopterin system of the molybdenum cofactor," *J Biol Inorg Chem.*, 9(1):59-66, Epub Nov. 20, 2003.
Nord et al., "Synthesis, structure, and biological activity of certain 2-deoxy-beta-D-ribo-hexopyranosyl nucleosides and nucleotides," *J Med Chem.*, 30(6):1044-1054, Jun. 1987.
Petrie et al., "Synthesis and biological activity of certain nucleoside and nucleotide derivatives of pyrazofurin," *J Med Chem.*, 29(2):268-278, Feb. 1986.
Pétursson et al., "Protecting groups in carbohydrate chemistry," *J. Chem. Educ.*, 74 (11), p. 1297, Epub Nov. 1997.
Puthenveetil et al., "Yeast display evolution of a kinetically efficient 13-amino acid substrate for lipoic acid ligase," *J Am Chem Soc.*, 131(45):16430-16438, Nov. 18, 2009.
Qiao, "Synthesis of cyclic sphingosine 1,3-phosphate (cSPP) through a photolytic reaction," *Tetrahedron Lett*, 39(49): 8959-8962, Dec. 3, 1998.
Raboisson et al., "A general approach toward the synthesis of C-nucleoside pyrazolo[1,5-a]-1,3,5-triazines and their 3',5'-bisphosphate C-nucleotide analogues as the first reported in vivo stable P2Y(1)-receptor antagonists," *J Org Chem.*, 67(23):8063-8071, Nov. 15, 2002.
Ruttens et al., "Synthesis of Phosphorylated, Conjugation-Ready Di-, Tri- and Tetrasaccharide Fragments of the O-Specific Polysaccharide of V. cholerae O139," *Eur. J. Org. Chem.*, 2007(26):4366-4375, Sep. 2007.
Sakaitani et al., "One-pot conversion of N-benzyloxycarbonyl group into N-tert-butoxycarbonyl group," *Tetrahedron Lett.* 29(24): 2983-2984, 1988.
Santamaria-Araujo et al., "The tetrahydropyranopterin structure of the sulfur-free and metal-free molybdenum cofactor precursor." *J Biol Chem.*, 279(16):15994-15999, Epub Feb. 3, 2004.
Sharma et al, "Bisheterocyclic synthesis and antimicrobial studies on some biologically significant 2-[N-(3¢-chloro-4¢-substituted azetidinone-2)]-ami-no-4-hydroxypurines," Indian Journal of Chemistry, Section B: Organic Chemistry Including Medicinal Chemistry, 43B(2): 385-388, Feb. 2004.
Shi et al., "Bisubstrate analogue inhibitors of 6-hydroxymethyl-7,8-dihydropterin pyrophosphokinase: synthesis and biochemical and crystallographic studies," *J Med Chem.*, 44(9):1364-1371, Apr. 26, 2001.
Shing et al., "Catalytic asymmetric epoxidation of alkenes with arabinose-derived uloses," *Tetrahedron*, 59(12):2159-2168, Mar. 17, 2003.
Soyka et al., "Pteridine. Teil XCIV. Synthese und Eigenschaften von 5,6-Dihydro-6-(1,2,3-trihydroxypropyl)pteridinen: Kovalente intramolekulare Addukte." *Helvetica Chimica Acta*, 73: 808-826, Jun 20, 1990.
Stahl et al., "General procedure for the synthesis of mono-N-acylated 1,6-diaminohexanes," *J Org. Chern.*, 43(11): 2285-2286, May 1978).
Switchenko and Brown, "The enzymatic conversion of dihydroneopterin triphosphate to tripolyphosphate and 6-pyruvoyl-tetrahydropterin, an intermediate in the biosynthesis of other pterins in *Drosophila melanogaster*," *J Biol Chem.*, 260(5):2945-2951, Mar. 10, 1985.
Tarbell et al., "New Method to Prepare N-t-Butoxycarbonyl Derivatives and the Corresponding Sulfur Analogs from di-t-Butyl Dicarbonate or di-t-Butyl Dithiol Dicarbonates and Amino Acids," *Proc Natl Acad Sci U S A.*, 69(3):730-732, Mar. 1972.

(56) References Cited

OTHER PUBLICATIONS

Taylor and Reiter, "Pteridines. 50. Unequivocal total synthesis of deoxyurothione," *J Org Chem.*, 47(3):528-531, 1982.
Testani et al., "Chemical reduction of pterins to dihydropterins as substrates for enzymatic reactions," *Anal Biochem.*, 358(1):20-24, Epub Aug. 17, 2006.
Thomas et al., "Fluorescence of pterin, 6-formylpterin, 6-carboxypterin and folic acid in aqueous solution: pH effects," *Photochem Photobiol Sci.*, 1(6):421-426, Jun. 2002.
Tidwell, "Oxidation of Alcohols to Carbonyl Compounds via Alkoxysulfonium Ylides: The Moffatt, Swern, and Related Oxidations," *Organic Reactions*, 39:297-555, 1990.
Tsuda et al., "Regioselective Mono-oxidation of Non-protected Carbohydrates by Brominolysis of the Tin Intermediates," *Chem. Pharm. Bull.*, 37(9): 2344-2350, 1989.
Van Allan, "2,4-Diamino-6-hydroxypyrimidine," *Org. Synth.*, 32:45, 1952; also published in *Org Synth.* Coll. vol. 4, p. 245, 1963.
Wei et al., "Tetrahydrobiopterin radical enzymology," *Chem Rev.*, 103(6):2365-2383, Jun. 2003.
Wood and Rashid, "The "off-template" problem: synthesis and alkylation of a fused-butyrolactone from d-glucose," *Tetrahedron Lett*, 28(17): 1933-1936, 1987.
Wuebbens and Rajagopalan, "Mechanistic and mutational studies of *Escherichia coli* molybdopterin synthase clarify the final step of molybdopterin biosynthesis," *J Biol Chem.* 278(16):14523-14532, Epub Feb. 3, 2003.
International Preliminary Report on Patentability for PCT/US2012/025689 issued Aug. 21, 2013, 6 pages.
International Search Report and Written Opinion for PCT/US2012/25689, mailed May 29, 2012, 14 pages.
Daniels et al., "Crystal structure of a molybdopterin synthase-precursor Z complex: insight into its sulfur transfer mechanism and its role in molybdenum cofactor deficiency," Biochemistry, Jan. 15, 2008; 47(2):615-626. Epub Dec. 20, 2007.
European Search Report for App. No. 12747519.2 dated Jul. 22, 2014, 2 pages.
Clinch et al., "Synthesis of cyclic pyranopterin monophosphate, a biosynthetic intermediate in the molybdenum cofactor pathway," J Med Chem., 56(4):1730-1738, Epub Feb. 19, 2013.
Hitzert et al., "Favorable outcome in a newborn with molybdenum cofactor type A deficiency treated with cPMP," Pediatrics, 130(4):e1005-e1010, Epub Sep. 17, 2012.
Johnson and Duran, "Molybdenum cofactor deficiency and isolated sulfite oxidase deficiency," The metabolic & molecular bases of inherited disease [eight edition] Chapter 128, 3163-3177, 2001.
Per et al., "Molybdenum cofactor deficiency: clinical features in a Turkish patient," Brain Dev., 29(6):365-368, Epub Dec. 8, 2006.
Schwahn et al., "Follow-up of two infants with molybdenum cofactor deficiency (MOCD) group A, on long-term treatment with cyclic pyranopterin monophosphate (CPMP)," J Inherit Metab Dis., 34 (Suppl 3):S84, Abstract P-024, 2011.
Schwarz "Molybdenum cofactor biosynthesis and deficiency," Cellular and Molecular Life Sciences CMLS, 62 (23):2792-2810, Dec. 2005.
Schwarz et al., "Rescue of lethal molybdenum cofactor deficiency by a biosynthetic precursor from *Escherichia coli*," Hum Mol Genet., 13(12):1249-1255, Epub Apr. 28, 2004.
van der Knaap and Valk, "Molybdenum cofactor deficiency and isolated sulfite oxidase deficiency," Magnetic resonance of myelination and myelin disorders, Third Edition, Chpt. 48, pp. 372-376, 2005.
Veldman et al., "Efficacy and safety of cyclic pyranoptern monophosphate in the treatment of six newborn patients with molybdenum cofactor deficiency type A," J Inherit Metab Dis., 34 (Suppl 3):S84, Abstract P-023, 2011.
Veldman et al., "Successful treatment of molybdenum cofactor deficiency type A with cPMP," Pediatrics, 125(5):e1249- e1254, Epub Apr. 12, 2010.
Berge et al., "Pharmaceutical Salts," J Pharm Sci., 66(1):1-19, Jan. 1977.

\* cited by examiner

METHODS FOR SYNTHESIZING MOLYBDOPTERIN PRECURSOR Z DERIVATIVES

CROSS-REFERENCE TO RELATED APPLICATIONS

This application is a National Stage application under 35 U.S.C. §371 of International Application No. PCT/US2012/025689, having an International Filing Date of Feb. 17, 2012, which claims priority to U.S. Provisional Application Ser. Nos. 61/444,399, filed Feb. 18, 2011; 61/498,801, filed Jun. 20, 2011; 61/444,280, filed Feb. 18, 2011; 61/498,808, filed Jun. 20, 2011; and 61/444,389, filed Feb. 18, 2011; and 61/599,314, filed Feb. 15, 2012; all of which are incorporated by reference in their entireties.

TECHNICAL FIELD

Provided herein are synthetic methods for preparing the molybdopterin derivative precursor Z and novel synthetic intermediates useful therein. Also provided herein are useful intermediates, derivatives, prodrugs, and pharmaceutically acceptable salts, solvates, and hydrates of precursor Z. These compounds are useful for, among other things, treating diseases associated with molybdenum cofactor deficiency.

BACKGROUND

Molybdenum cofactor (Moco) deficiency is a pleiotropic genetic disorder. Moco consists of molybdenum covalently bound to one or two dithiolates attached to a unique tricyclic pterin moiety commonly referred to as molybdopterin (MPT). Moco is synthesized by a biosynthetic pathway that can be divided into four steps, according to the biosynthetic intermediates precursor Z (cyclic pyranopterin monophosphate; cPMP), MPT, and adenylated MPT. Mutations in the Moco biosynthetase genes result in the loss of production of the molybdenum dependent enzymes sulfite-oxidase, xanthine oxidoreductase, and aldehyde oxidase. Whereas the activities of all three of these cofactor-containing enzymes are impaired by cofactor deficiency, the devastating consequences of the disease can be traced to the loss of sulfite oxidase activity. Human Moco deficiency is a rare but severe disorder accompanied by serious neurological symptoms including attenuated growth of the brain, untreatable seizures, dislocated ocular lenses, and mental retardation. Until recently, no effective therapy was available and afflicted patients suffering from Moco deficiency died in early infancy.

It has been found that administration of the molybdopterin derivative precursor Z, a relatively stable intermediate in the Moco biosynthetic pathway, is an effective means of therapy for human Moco deficiency and associated diseases related to altered Moco synthesis (see U.S. Pat. No. 7,504,095). As with most replacement therapies for illnesses, however, the treatment is limited by the availability of the therapeutic active agent.

SUMMARY

Precursor Z (a compound of formula (I) and (XIII)) has previously been prepared using fermentation processes. These processes, however, have stability issues, low yields, and are cost-prohibitive for large-scale production. The following synthetic processes are proposed as an alternative to these fermentation processes.

Provided herein is a process for preparing a compound of formula (I):

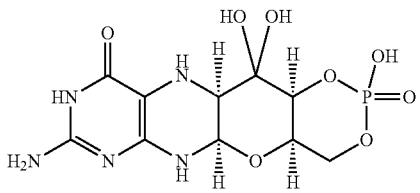

or a pharmaceutically acceptable salt thereof, the process comprising: reacting a compound of formula (II):

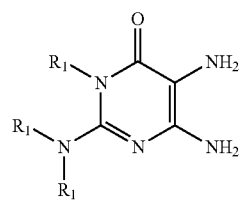

wherein each $R_1$ is independently H or a protecting group, with a compound of formula (III):

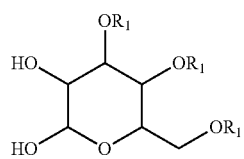

to produce a compound of formula (IV):

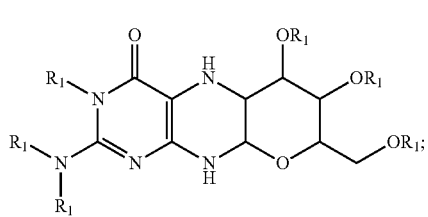

selectively protecting the compound of formula (IV) to prepare a compound of formula (V):

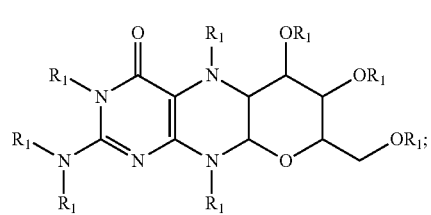

phosphorylating the compound of formula (V) to prepare a compound of formula (VI):

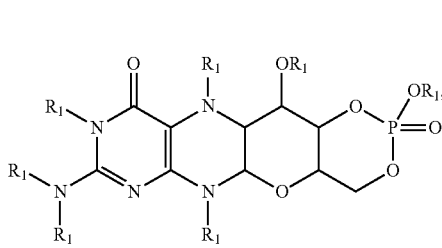

oxidizing the compound of formula (VI) to prepare a compound of formula (VII):

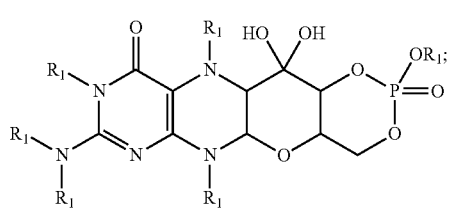

and deprotecting the compound of formula (VII) to prepare the compound of formula (I).

In some embodiments, the pharmaceutically acceptable salt is an HCl salt. In some embodiments, the pharmaceutically acceptable salt is an HBr salt.

In some embodiments, the compound of formula (II) is:

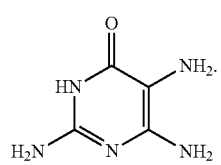

In some embodiments, the compound of formula (III) is a protected or unprotected galactose, mannose, glucose, or gulose. For example, a compound of formula (III) can be:

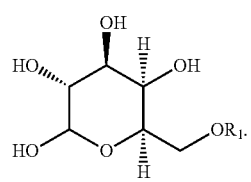

In some embodiments, two adjacent $R_1$ groups come together to form an isopropylidine acetal or benzylidine acetal moiety.

In some embodiments, the reaction between the compounds of formula (II) and (III) comprises reacting the compound of formula (II) and the compound of formula (III) in the presence of a hydrazine. For example, the hydrazine can be selected from the group consisting of phenylhydrazines and alkylhydrazines. In some embodiments, the hydrazine is phenylhydrazine.

In some embodiments, the phosphorylation step comprises reacting the compound of formula (V) with a P(V) phosphorylating agent. For example, a P(V) phosphorylating agent can be selected from the group consisting of: $POCl_3$; $H_3PO_4$; $PO(OBn)_xCl_{3-x}$; $Cl_3CCH_2OP(O)Cl_2$; and $(BnO)_2P(O)OP(O)(OBn)_2$. In some embodiments, the P(V) phosphorylating agent is $POCl_3$. In some embodiments, the phosphorylation step comprises reacting the compound of formula (V) with a P(III) phosphitylating agent. For example, the P(III) phosphitylating agent can be selected from the group consisting of: $P(OCH_2CH_2CN)_2Cl$; $P(OCH_2CH_2CN)(NPr_2-i)Cl$; and cyanoethyl-O—$P[N(i-Pr)_2]_2$. In some embodiments, the phosphorylation step further comprises oxidizing the resulting phosphite to prepare the phosphate of compound (VI).

In some embodiments, the oxidation step comprises reacting the compound of formula (VI) with an oxidizing agent selected from the group consisting of: $RuO_4$; Dess-Martin; DMSO/triflic anhydride; and PDC.

In some embodiments, the deprotection of the compound of formula (VII) is performed under anaerobic conditions.

Also provided herein is a process for preparing a compound of formula (I), or a pharmaceutically acceptable salt thereof, the process comprising: reacting a compound of formula (II-A):

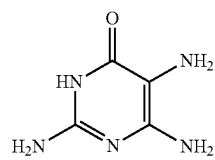

with a compound of formula (III-A):

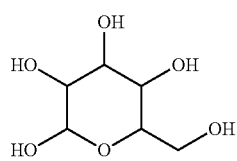

in the presence of a hydrazine to produce a compound of formula (IV-A):

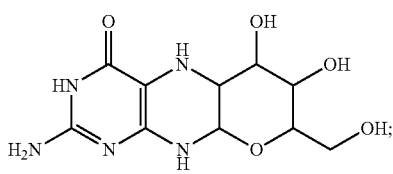

selectively protecting the compound of formula (IV-A) to prepare a compound of formula (V-A):

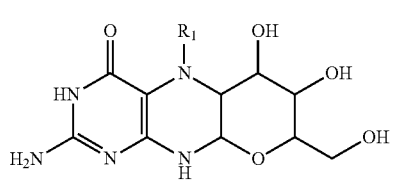

wherein $R_1$ is a protecting group; phosphorylating the compound of formula (V-A) to prepare a compound of formula (VI-A):

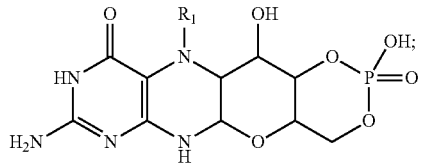

(VI-A)

oxidizing the compound of formula (VI-A) to prepare a compound of formula (VII-A):

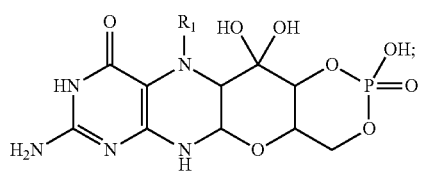

(VII-A)

and deprotecting the compound of formula (VII-A) to prepare the compound of formula (I).

Further provided herein is a process for preparing a compound of formula (I), or a pharmaceutically acceptable salt thereof, the process comprising: reacting a compound of formula (II-A) with a compound of formula (III-A) in the presence of a hydrazine to produce a compound of formula (IV-A); selectively protecting the compound of formula (IV-A) to prepare a compound of formula (V-B):

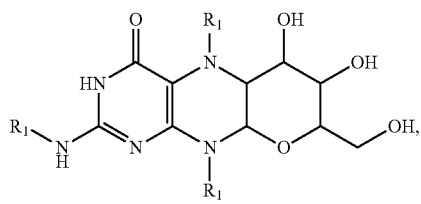

(V-B)

wherein each $R_1$ is independently a protecting group; phosphorylating the compound of formula (V-B) to prepare a compound of formula (VI-B):

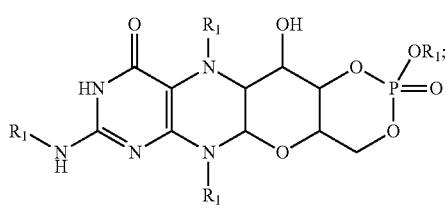

(VI-B)

oxidizing the compound of formula (VI-B) to prepare a compound of formula (VII-B):

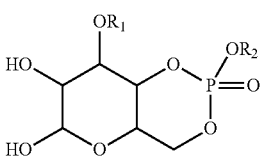

(VII-B)

and deprotecting the compound of formula (VII-B) to prepare the compound of formula (I).

Also provided herein is a process for preparing a compound of formula (I), or a pharmaceutically acceptable salt thereof, comprising: reacting a compound of formula (II) with a compound of formula (VIII):

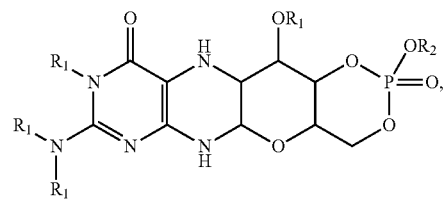

(VIII)

wherein each $R_1$ and $R_2$ are independently H or a protecting group; to produce a compound of formula (IX):

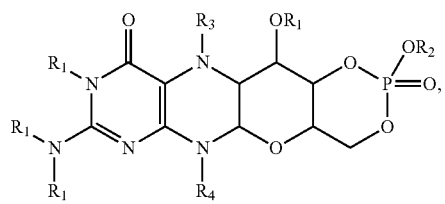

(IX)

selectively protecting the compound of formula (IX) to prepare a compound of formula (X):

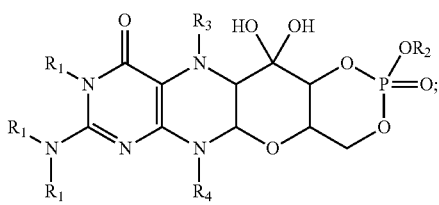

(X)

wherein $R_3$ is a protecting group and $R_4$ is H or a protecting group; oxidizing the compound of formula (X) to prepare a compound of formula (XI):

(XI)

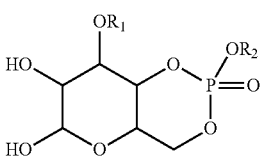

and deprotecting the compound of formula (XI) to prepare the compound of formula (I).

Further provided herein is a process for preparing a compound of formula (I), or a pharmaceutically acceptable salt thereof, the process comprising reacting a compound of formula (II) with a compound of formula (III) to produce a compound of formula (IV); selectively protecting the compound of formula (IV) to prepare a compound of formula (V); oxidizing the compound of formula (V) to prepare a compound of formula (XII):

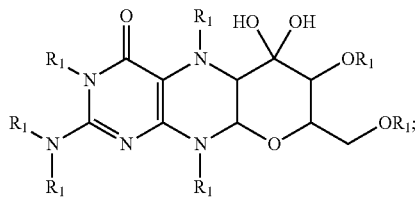

(XII)

phosphorylating the compound of formula (XII) to prepare a compound of formula (VII); and deprotecting the compound of formula (VII) to prepare the compound of formula (I).

This disclosure also provides a process for preparing a compound of formula (I), or a pharmaceutically acceptable salt thereof, the process comprising: reacting a compound of formula (II) with a compound of formula (XXII):

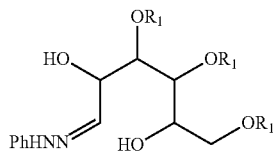

(XXII)

wherein each $R_1$ is independently H or a protecting group, to produce a compound of formula (IV); selectively protecting the compound of formula (IV) to prepare a compound of formula (V); phosphorylating the compound of formula (V) to prepare a compound of formula (VI); oxidizing the compound of formula (VI) to prepare a compound of formula (VII); and deprotecting the compound of formula (VII) to prepare the compound of formula (I).

In some embodiments, the compound of formula (II) is:

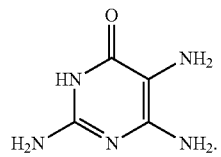

In some embodiments, the compound of formula (XXII) is:

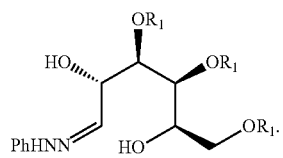

In some embodiments, the phosphorylation step comprises reacting the compound of formula (V) with a P(V) phosphorylating agent. For example, a P(V) phosphorylating agent can be selected from the group consisting of: $POCl_3$; $H_3PO_4$; $PO(OBn)_xCl_{3-x}$; $Cl_3CCH_2OP(O)Cl_2$; and $(BnO)_2P(O)OP(O)(OBn)_2$. In some embodiments, the P(V) phosphorylating agent is $Cl_2PO(OCH_3)$.

In some embodiments, the oxidation step comprises reacting the compound of formula (VI) with an oxidizing agent selected from the group consisting of: $RuO_4$; Dess-Martin; DMSO/triflic anhydride; DMSO/TFAA; and PDC.

In some embodiments, the deprotection of the compound of formula (VII) is performed under anaerobic conditions.

Further provided herein is a process for preparing a compound of formula (I), or a pharmaceutically acceptable salt thereof, the process comprising: reacting a compound of formula (II-A):

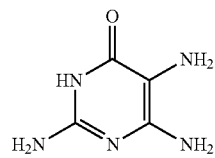

(II-A)

with a compound of formula (XXII-A):

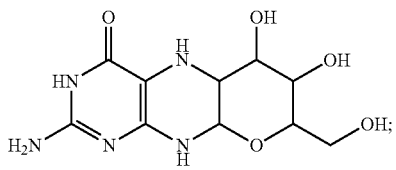

in the presence of a base to produce a compound of formula (IV-A):

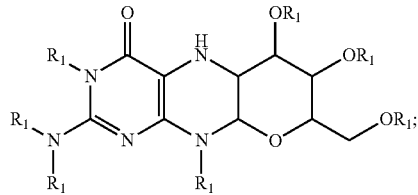

(IV-A)

selectively protecting the compound of formula (IV-A) to prepare a compound of formula (V-C):

(V-C)

wherein each $R_1$ is independently H or a protecting group, phosphorylating the compound of formula (V-C) to prepare a compound of formula (VI-C):

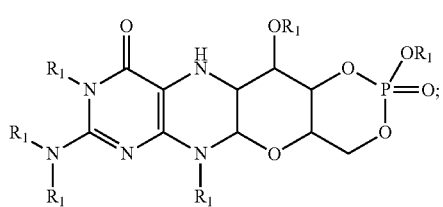
(VI-C)

oxidizing the compound of formula (VI-C) to prepare a compound of formula (VII-C):

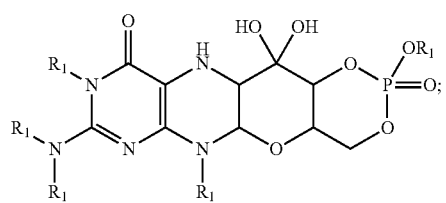
(VII-C)

and deprotecting the compound of formula (VII-C) to prepare the compound of formula (I).

This disclosure also provides a process for preparing a compound of formula (I), or a pharmaceutically acceptable salt thereof, the process comprising: reacting a compound of formula (XXIII):

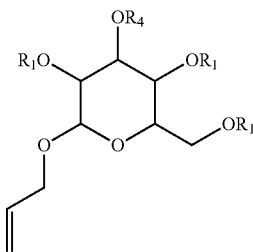
(XXIII)

wherein each $R_1$ is independently H or a protecting group and $R_4$ is H or a leaving group; to produce a compound of formula (XXIV):

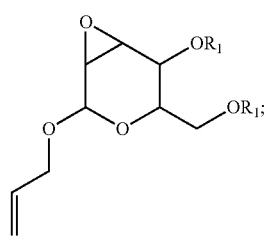
(XXIV)

reacting a compound of formula (XXIV) with a compound of formula (II) to produce a compound of formula (XXV):

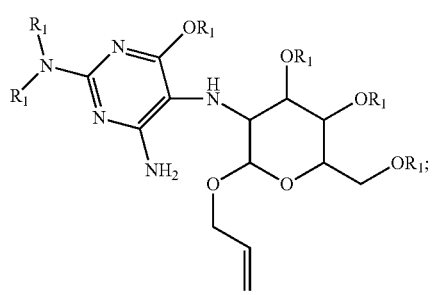
(XXV)

catalyzing ring formation of the compound of formula (XXV) to produce a compound of formula (IV); selectively protecting the compound of formula (IV) to prepare a compound of formula (V); phosphorylating the compound of formula (V) to prepare a compound of formula (VI); oxidizing the compound of formula (VI) to prepare a compound of formula (VII); and deprotecting the compound of formula (VII) to prepare the compound of formula (I).

In some embodiments, the compound of formula (XXIII) is selected from the group consisting of:

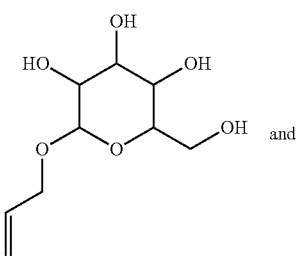
and

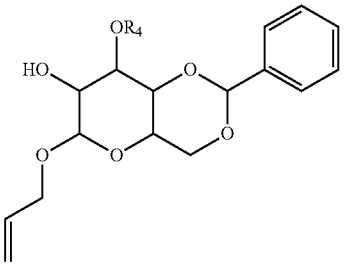

In some embodiments, the compound of formula (XXIV) can be:

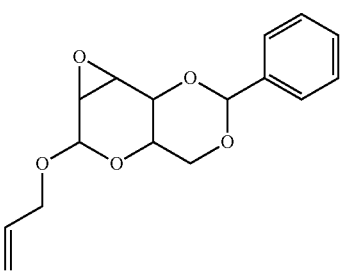

In some embodiments, the compound of formula (XXV) is:

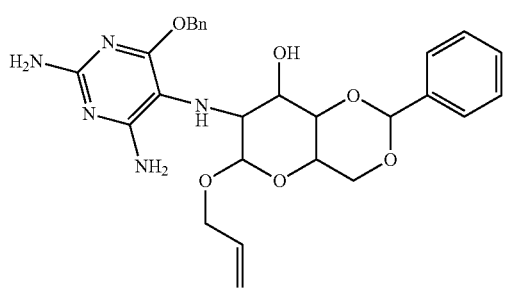

In some embodiments, the phosphorylation step comprises reacting the compound of formula (V) with a P(V) phosphorylating agent. For example, a P(V) phosphorylating agent can be selected from the group consisting of: $POCl_3$; $H_3PO_4$; $PO(OBn)_xCl_3$; $Cl_3CCH_2OP(O)Cl_2$; and $(BnO)_2P(O)OP(O)(OBn)_2$. In some embodiments, the P(V) phosphorylating agent is $Cl_2PO(OCH_3)$.

In some embodiments, the oxidation step comprises reacting the compound of formula (VI) with an oxidizing agent selected from the group consisting of: $RuO_4$; Dess-Martin; DMSO/triflic anhydride; DMSO/TFAA; and PDC.

In some embodiments, the deprotection of the compound of formula (VII) is performed under anaerobic conditions.

In some embodiments, the compound of formula (XXIII) is:

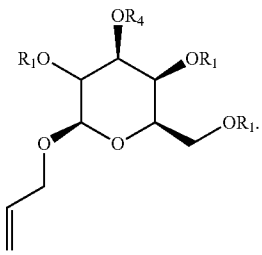

In some embodiments, the compound of formula (XXIV) is:

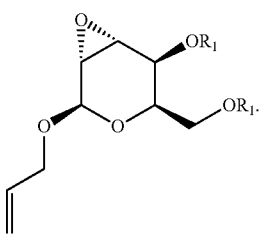

In some embodiments, the compound formula (XXV) is:

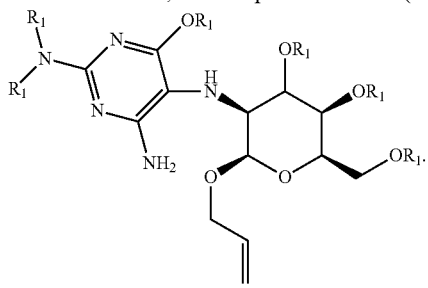

In some embodiments, a leaving group is selected from the group consisting of: tosylates, brosylates, nosylates, mesylates, oxoniums, triflates, nonaflates, and tresylates.

Also provided herein is a process for preparing a compound of formula (I), or a pharmaceutically acceptable salt thereof, the process comprising: reacting a compound of formula (XXIII-A):

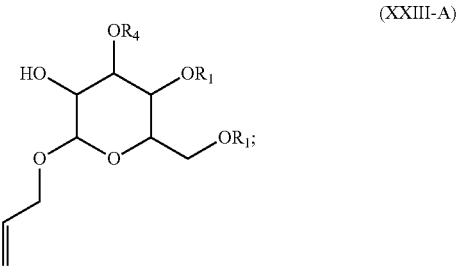

(XXIII-A)

wherein: each $R_1$ is independently H or a protecting group, and $R_4$ is H or a leaving group, to produce a compound of formula (XXIV):

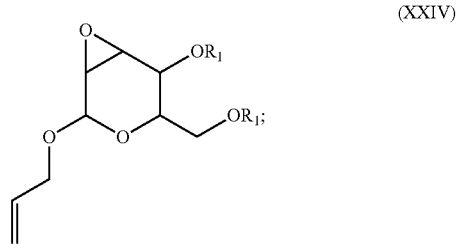

(XXIV)

reacting a compound of formula (XXIV) with a compound of formula (II-A):

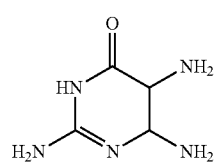

(II-A)

to produce a compound of formula (XXV-A):

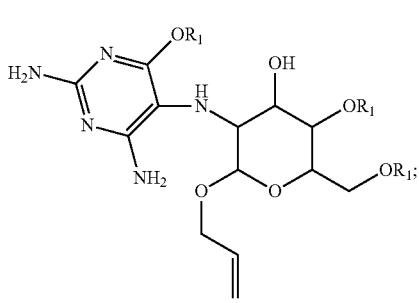

(XXV-A)

catalyzing ring formation of the compound of formula (XXV-A) to produce a compound of formula (IV-D):

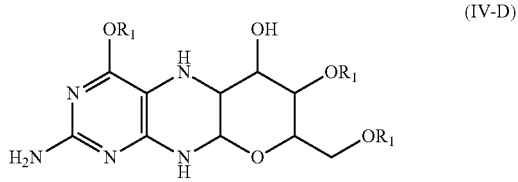

selectively protecting the compound of formula (IV-D) to prepare a compound of formula (V-D):

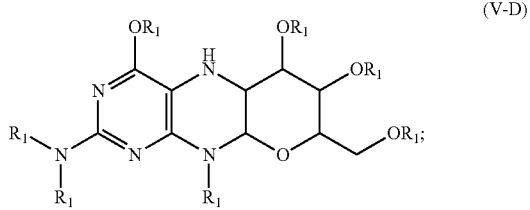

phosphorylating the compound of formula (V-D) to prepare a compound of formula (VI-D):

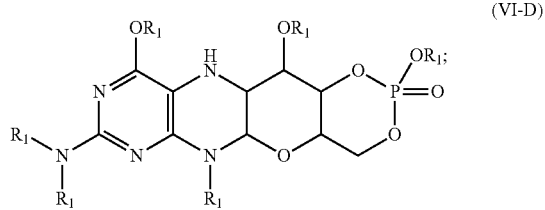

oxidizing the compound of formula (VI-D) to prepare a compound of formula (VII-D):

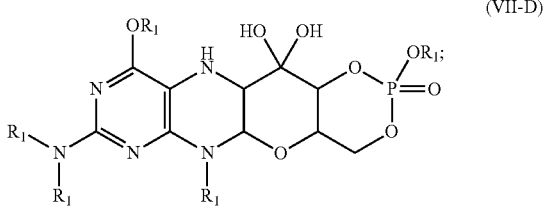

and deprotecting the compound of formula (VII-D) to prepare the compound of formula (I).

This disclosure also provides a process for preparing a compound of formula (I), or a pharmaceutically acceptable salt thereof, the process comprising: oxidizing the compound of formula (VI) to prepare a compound of formula (VII); and deprotecting the compound of formula (VII) to prepare the compound of formula (I).

In some embodiments, a compound of formula (I), or a pharmaceutically acceptable salt thereof, can be prepared by phosphorylating the compound of formula (V) to prepare a compound of formula (VI); oxidizing the compound of formula (VI) to prepare a compound of formula (VII); and deprotecting the compound of formula (VII) to prepare the compound of formula (I).

Also provided herein is a process for preparing a compound of formula (I), or a pharmaceutically acceptable salt thereof, the process comprising: selectively protecting the compound of formula (IV) to prepare a compound of formula (V); phosphorylating the compound of formula (V) to prepare a compound of formula (VI); oxidizing the compound of formula (VI) to prepare a compound of formula (VII); and deprotecting the compound of formula (VII) to prepare the compound of formula (I).

In some embodiments, the processes described above further comprise formulating the compound of formula (I) as a pharmaceutical composition.

Further provided herein is a compound of formula (I), or a pharmaceutically acceptable salt thereof, prepared by any of the processes described above. In some embodiments, a pharmaceutical composition is provided comprising a compound of formula (I), or a pharmaceutically acceptable salt thereof, prepared by any of the processes described above and a pharmaceutically acceptable excipient.

This disclosure also provides a process for preparing a compound of formula (XIII):

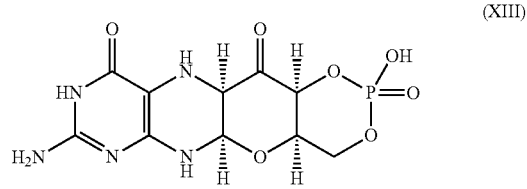 [SMILES: Nc1nc2c(c(=O)[nH]1)N[C@H]1C(=O)[C@H]3OP(=O)(O)OC[C@H]3O[C@H]1N2]

or a pharmaceutically acceptable salt form thereof, the process comprising: reacting a compound of formula (II):

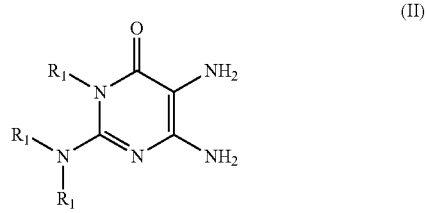

wherein each $R_1$ is independently H or a protecting group, with a compound of formula (III):

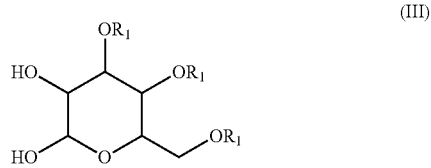

to produce a compound of formula (IV):

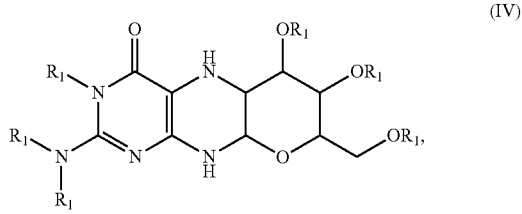

selectively protecting the compound of formula (IV) to prepare a compound of formula (V):

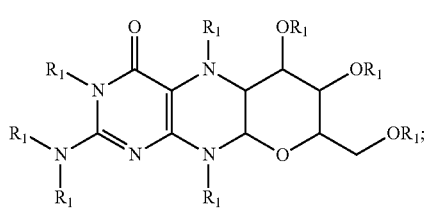
(V)

phosphorylating the compound of formula (V) to prepare a compound of formula (VI):

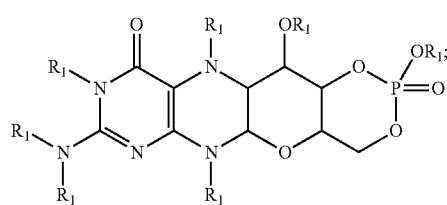
(VI)

oxidizing the compound of formula (VI) to prepare a compound of formula (XIV):

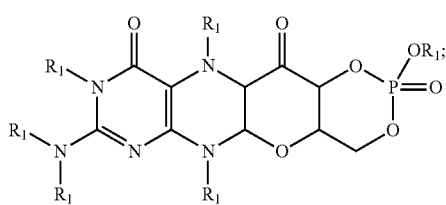
(XIV)

and (e) deprotecting the compound of formula (XIV) to prepare the compound of formula (XIII).

Also provided herein is a process for preparing a compound of formula (XIII), or a pharmaceutically acceptable salt thereof, the process comprising: reacting a compound of formula (II) with a compound of formula (VIII):

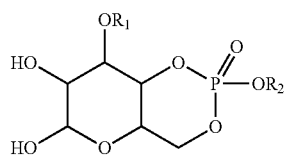
(VIII)

wherein each $R_1$ and $R_2$ is H or a protecting group, to produce a compound of formula (IX):

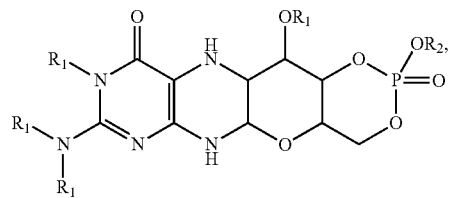
(IX)

selectively protecting the compound of formula (IX) to prepare a compound of formula (X):

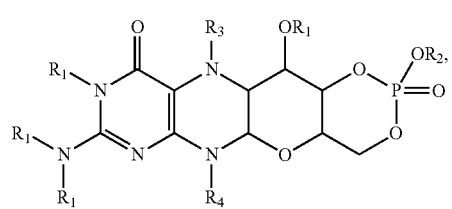
(X)

wherein $R_3$ is a protecting group and $R_4$ is H or a protecting group; oxidizing the compound of formula (X) to prepare a compound of formula (XV):

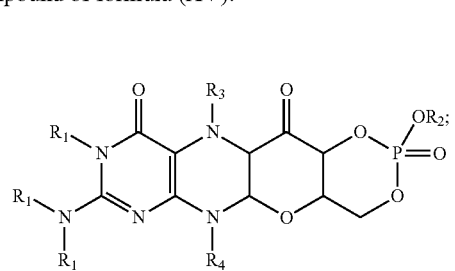
(XV)

and deprotecting the compound of formula (XV) to prepare the compound of formula (XIII).

Further provided herein is a process for preparing a compound of formula (XIII), or a pharmaceutically acceptable salt thereof, the process comprising: reacting a compound of formula (II) with a compound of formula (III) to produce a compound of formula (IV); selectively protecting the compound of formula (IV) to prepare a compound of formula (V); phosphorylating the compound of formula (V) to prepare a compound of formula (VI); oxidizing the compound of formula (VI) to prepare a compound of formula (XIV); and deprotecting the compound of formula (XIV) to prepare the compound of formula (XIII).

This disclosure also provides a process for preparing a compound of formula (XIII), or a pharmaceutically acceptable salt form thereof, the process comprising: oxidizing the compound of formula (VI) to prepare a compound of formula (XIV); and deprotecting the compound of formula (XIV) to prepare the compound of formula (XIII).

In some embodiments, a compound of formula (XIII), or a pharmaceutically acceptable salt thereof, is prepared phosphorylating the compound of formula (V) to prepare a compound of formula (VI); oxidizing the compound of formula (VI) to prepare a compound of formula (XIV); and deprotecting the compound of formula (XIV) to prepare the compound of formula (XIII).

Also provided herein is a process for preparing a compound of formula (XIII), or a pharmaceutically acceptable salt form thereof, the process comprising: selectively protecting the compound of formula (IV) to prepare a compound of formula (V); phosphorylating the compound of formula (V) to prepare a compound of formula (VI); oxidizing the compound of formula (VI) to prepare a compound of formula (XIV); and deprotecting the compound of formula (XIV) to prepare the compound of formula (XIII).

This disclosure also provides a process for preparing a compound of formula (XIII), or a pharmaceutically acceptable salt thereof, the process comprising: reacting a compound of formula (II) with a compound of formula (XXII) to produce a compound of formula (IV); selectively protecting the compound of formula (IV) to prepare a compound of formula (V); phosphorylating the compound of formula (V) to prepare a compound of formula (VI); oxidizing the compound of formula (VI) to prepare a compound of formula (XIV); and deprotecting the compound of formula (XIV) to prepare the compound of formula (XIII).

Also provided herein is a process for preparing a compound of formula (XIII), or a pharmaceutically acceptable salt thereof, the process comprising: reacting a compound of formula (XXIII) to produce a compound of formula (XXIV); reacting a compound of formula (XXIV) with a compound of formula (II) to produce a compound of formula (XXV); catalyzing ring formation of the compound of formula (XXV) to produce a compound of formula (IV); selectively protecting the compound of formula (IV) to prepare a compound of formula (V); phosphorylating the compound of formula (V) to prepare a compound of formula (VI); oxidizing the compound of formula (VI) to prepare a compound of formula (XIV); and deprotecting the compound of formula (XIV) to prepare the compound of formula (XIII).

In some embodiments, the processes described above further comprise formulating the compound of formula (XIII) as a pharmaceutical composition.

Further provided herein is a compound of formula (XIII) prepared by any of the processes described above. In some embodiments, a pharmaceutical composition is provided comprising a compound of formula (XIII), or a pharmaceutically acceptable salt thereof, prepared by any of the processes described above and a pharmaceutically acceptable excipient.

This disclosure also provides a compound of formula (IV):

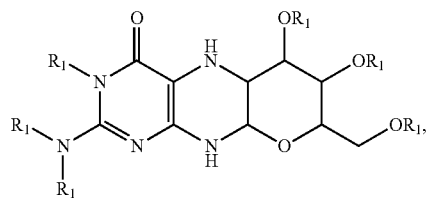

(IV)

or a pharmaceutically acceptable salt form thereof, wherein each $R_1$ is independently H or a protecting group. For example, a compound of formula (IV) can be:

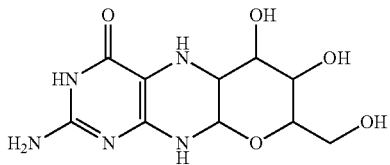 [SMILES: Nc1nc2c(c(=O)[nH]1)NC1C(N2)OC(CO)C(O)C1O]

or a pharmaceutically acceptable salt form thereof. In some embodiments, the compound of formula (IV) is:

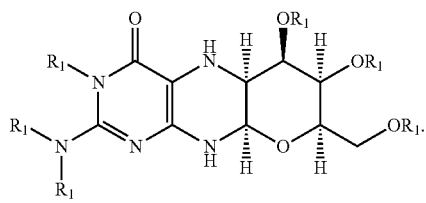

Also provided herein is a compound of formula (V):

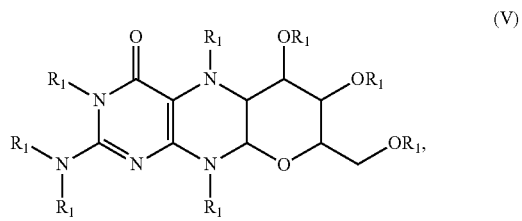

(V)

or a pharmaceutically acceptable salt form thereof, wherein each $R_1$ is independently H or a protecting group. For example, a compound of formula (V) can be selected from the group consisting of:

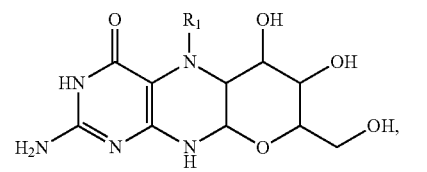

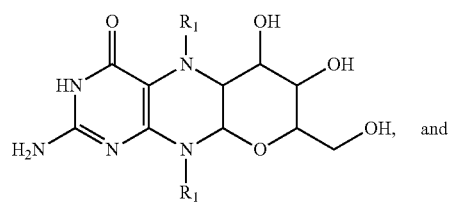

and

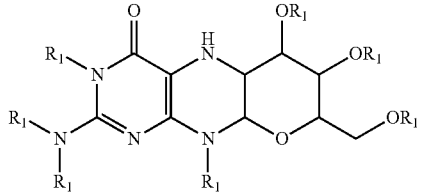

or a pharmaceutically acceptable salt form thereof. In some embodiments, a compound of formula (V) is selected from the group consisting of:

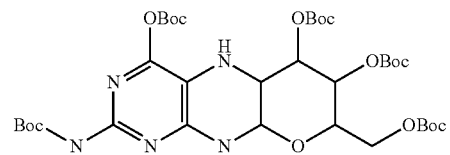

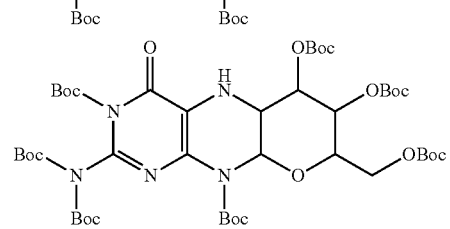

-continued

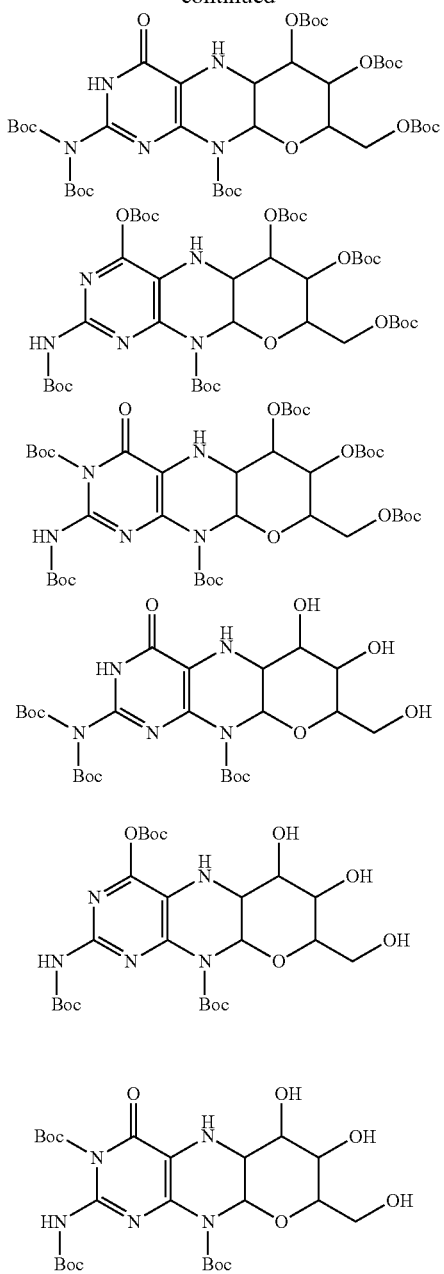

or a pharmaceutically acceptable salt thereof. In some embodiments, the compound of formula (V) is:

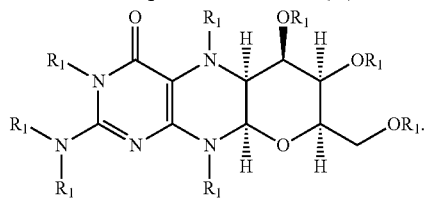

Further provided herein is a compound of formula (VI):

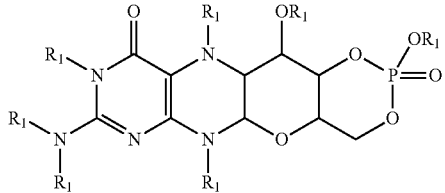

(VI)

or a pharmaceutically acceptable salt form thereof, wherein each $R_1$ is independently H or a protecting group. For example, a compound of formula (VI) can be selected from the group consisting of:

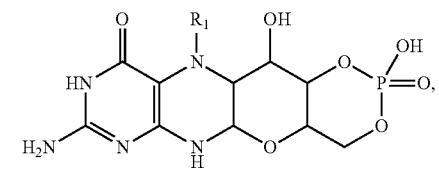

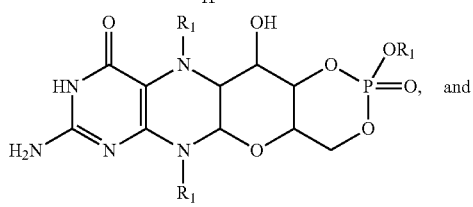

and

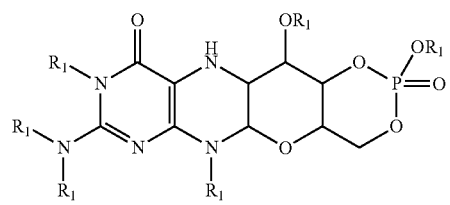

or a pharmaceutically acceptable salt form thereof. In some embodiments, a compound of formula (VI) is selected from the group consisting of:

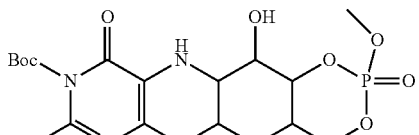

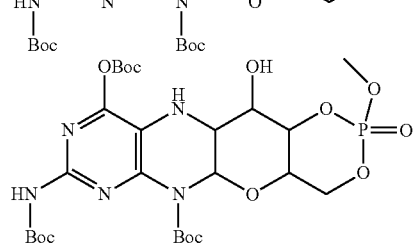

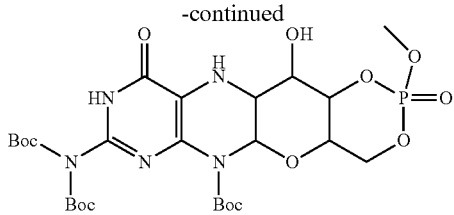

or a pharmaceutically acceptable salt thereof. In some embodiments, the compound formula (VI) is:

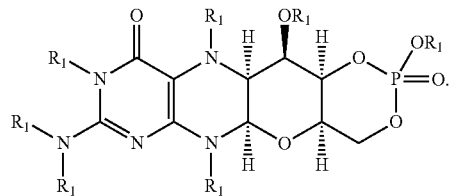

Provided herein is a compound of formula (VII):

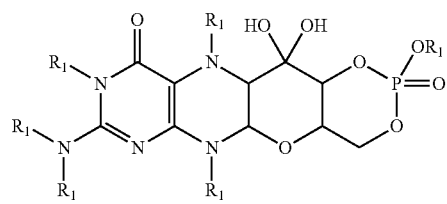

(VII)

or a pharmaceutically acceptable salt form thereof, wherein each $R_1$ is independently H or a protecting group. For example, a compound of formula (VII) is selected from the group consisting of:

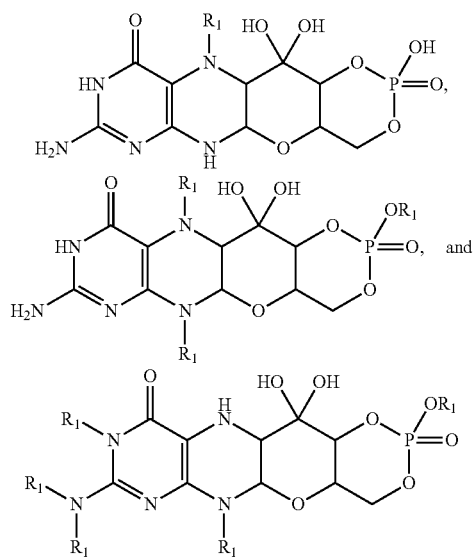

or a pharmaceutically acceptable salt form thereof. In some embodiments, a compound of formula (VII) is selected from the group consisting of:

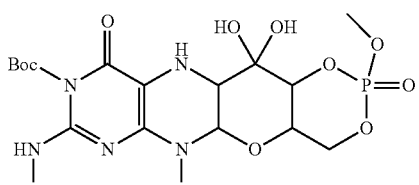

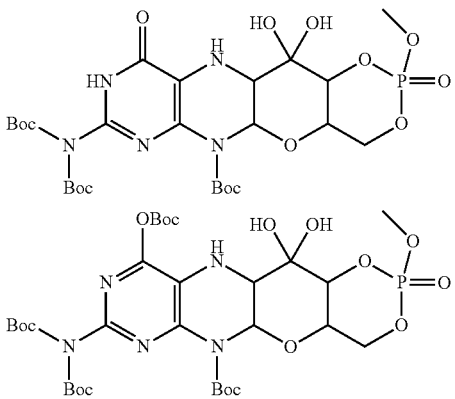

or a pharmaceutically acceptable salt form thereof. In some embodiments, the compound of formula (VII) is:

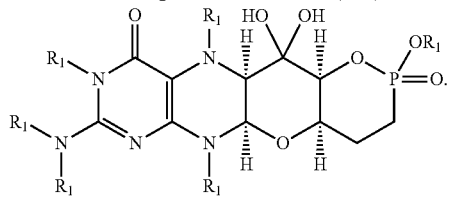

This disclosure also provides a process of preparing a compound of formula (XXIV):

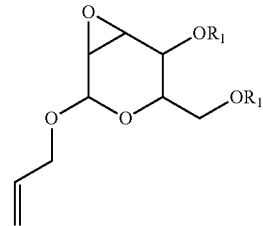

or a pharmaceutically acceptable salt thereof, wherein each $R_1$ is H or a protecting group, the method comprising: reacting a compound of formula (XXIII):

(XXIII)

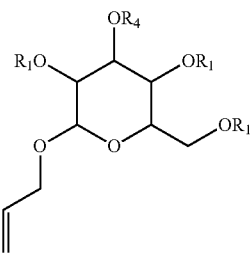

wherein $R_1$ is H or a protecting group and $R_4$ is H or a leaving group, with a base to prepare a compound of formula (XXIV).

DETAILED DESCRIPTION

Figure 1:
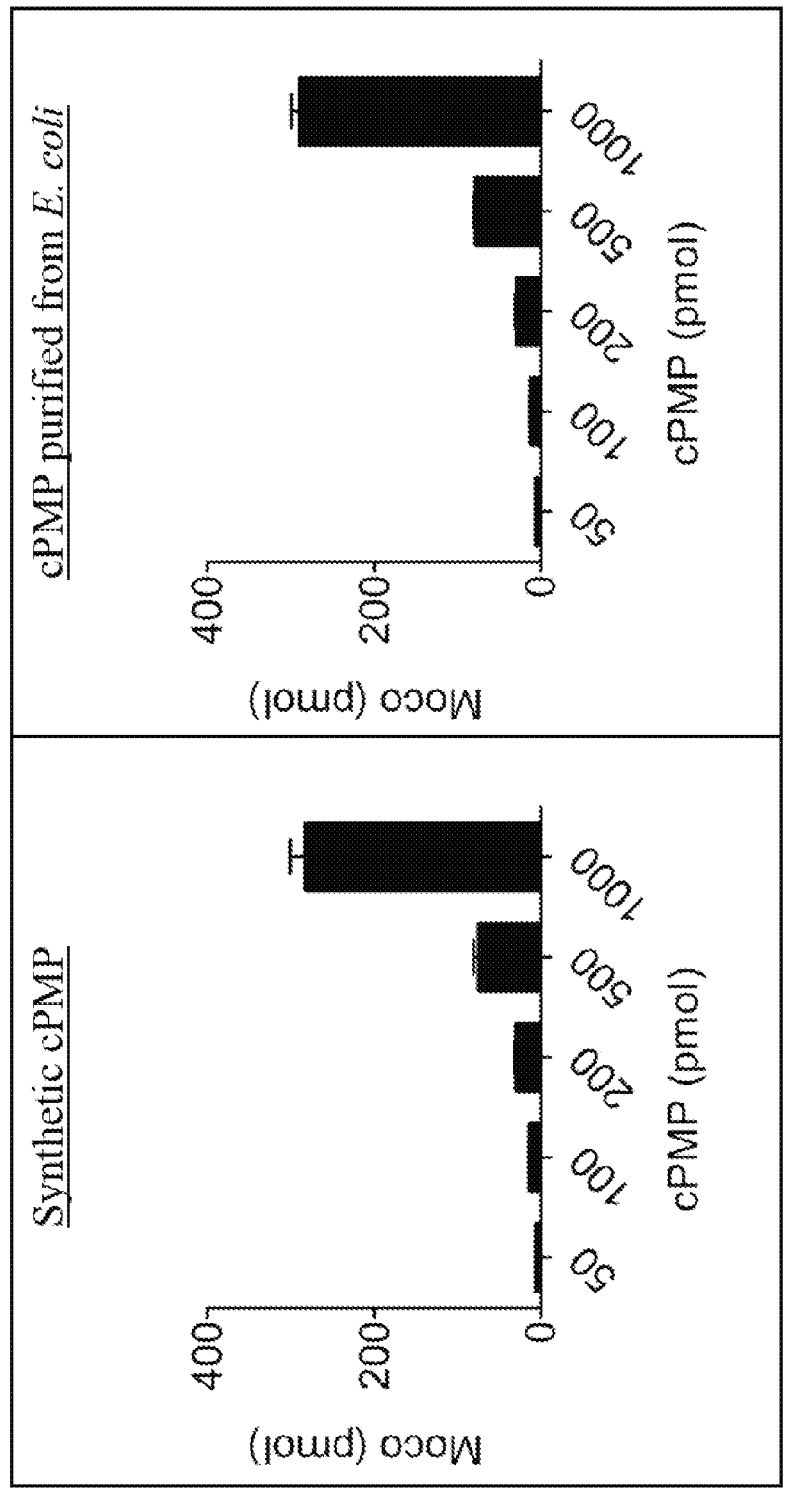
FIG. 1 shows bar graphs illustrating the in vitro synthesis of Moco using both synthetic precursor Z (cPMP) and precursor Z (cPMP) prepared and purified from a fermentation process.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Unless defined otherwise, all technical and scientific terms used herein have the same meaning as is commonly understood by one of ordinary skill in the art to which this disclosure belongs. All patents, applications, published applications, and other publications cited herein are incorporated by reference in their entirety. In the event that there is a plurality of definitions for terms cited herein, those in this section prevail unless otherwise stated.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trifluoroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

The term "prodrug," as used herein, refers to a compound which, upon administration to a subject, undergoes chemical conversion by metabolic or chemical processes to yield, e.g., the compounds described herein, and/or a salt and/or solvate thereof. The term "prodrugs" can include esters and carbonates formed, for example, by reacting one or more hydroxyl groups of the compounds described herein with alkyl, alkoxy, or aryl substituted acylating agents employing procedures known to those skilled in the art to generate, e.g., the corresponding acetates, pivalates, methylcarbonates, and benzoates. For example, compounds containing a carboxy group can form physiologically hydrolyzable esters which serve as prodrugs by being hydrolyzed in the body to yield the compounds provided herein. Such prodrugs can be administered orally since hydrolysis in many instances occurs under the influence of the digestive enzymes. Parenteral administration may also be used, e.g., in situations where hydrolysis occurs in the blood.

The term "solvate" is used herein to describe a molecular complex comprising a compound provided herein and a stoichiometric amount of one or more pharmaceutically acceptable solvent molecules, for example, ethanol. The term "hydrate" is employed when the solvent is water. Typical procedures for making and identifying hydrates and solvates are described on pages 202-209 of K. J. Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999, which is incorporated by reference herein in its entirety.

As used herein, chemical structures which contain one or more stereocenters depicted with dashed and bold bonds (i.e., ▬▬) are meant to indicate absolute stereochemistry of the stereocenter(s) present in the chemical structure. As used herein, bonds symbolized by a simple line do not indicate a stereo-preference. Unless otherwise indicated to the contrary, chemical structures, which include one or more stereocenters, illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

Resolution of racemic mixtures of compounds can be carried out by any of numerous methods known in the art. An examplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

Compounds provided herein can also include all isotopes of atoms occurring in the intermediates or final compounds. Isotopes include those atoms having the same atomic number but different mass numbers. For example, isotopes of hydrogen include hydrogen, tritium, and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, isopropanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. Conventional methods for preparing salt forms are described, for example, in *Handbook of Pharmaceutical Salts: Properties, Selection, and Use,* Wiley-VCH, 2002.

Synthesis

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry,* 1$^{st}$ Ed., Oxford University Press, 2000; *March's Advanced Organic Chemistry: Reactions, Mechanisms, and Structure,* 5$^{th}$ Ed., Wiley-Interscience Publication, 2001; and Peturssion, S. et al., "*Protecting Groups in Carbohydrate Chemistry,*" *J. Chem. Educ.,* 74(11), 1297 (1997) (each of which is incorporated herein by reference in its entirety).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

The compound of formula (I), and other useful compounds and intermediates, can be formed as shown in Scheme 1. For example, a diaminopyrimidinone compound of formula (II) can be reacted with a protected or unprotected hexose sugar of formula (III) to give a compound of formula (IV). The ring nitrogen atoms of the piperizine ring of formula (IV) can then be selectively protected using standard conditions to give a derivative of formula (V). Phosphorylation of the compound of formula (V) can furnish a phosphate intermediate of formula (VI). The phosphate of formula (VI) can be converted to a diol of formula (VII) under appropriate oxidation conditions. Finally, the compound of formula (VII) can be deprotected to give the compound of formula (I).

Scheme 1

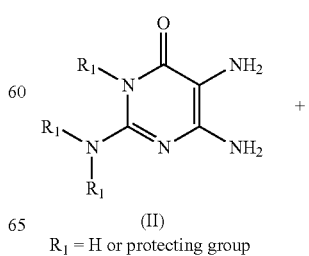

(II)

R$_1$ = H or protecting group

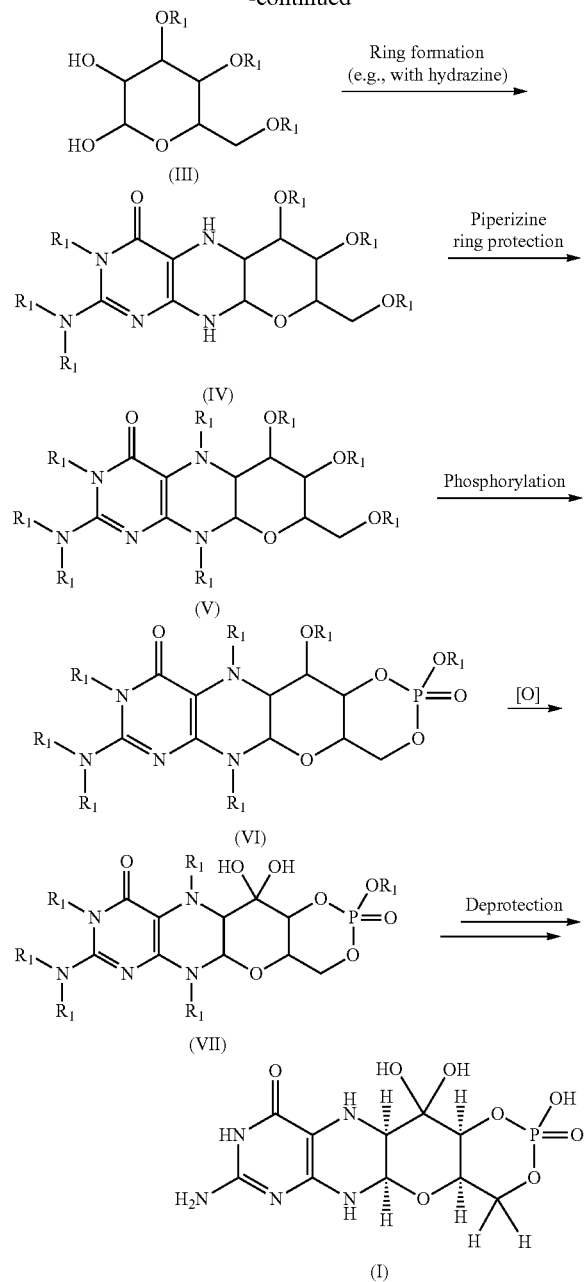

Compounds of Formula (II):

In some embodiments, the preparation of compounds of formula (II) is contemplated:

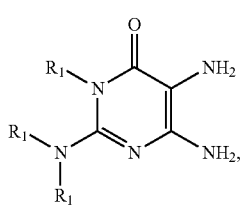
(II)

wherein each $R_1$ is independently H or a protecting group.

Formula (II) can include, for example, the compound 2,5,6-triaminopyrimidin-4(3H)-one:

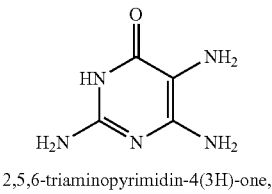

2,5,6-triaminopyrimidin-4(3H)-one, and salts and derivatives thereof. In some embodiments, a compound of formula (II) can be in the form of a hydrochloride salt:

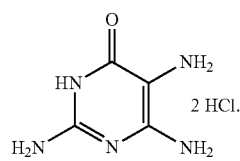

As indicated, certain functional groups of the formula (II) structure (e.g., the amino group, the 2-position of the pyrimidine ring, and the ring nitrogen atom at the 3-position) may be protected with an $R_1$ protecting group. For this purpose, $R_1$ may include any suitable amino protecting groups, including, but not limited to, carbamate, amide, N-alkyl, or N-aryl-derived protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz).

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

Compounds of formula (II) can be prepared using known methods, such as those described by Sharma et al., *Indian Journal of Chemistry, Section B: Organic Chemistry Including Medicinal Chemistry*, 43B, 385 (2004). For example, the 2,5,6-triaminoprimidin-4(3H)-one is prepared as shown in Scheme 2.

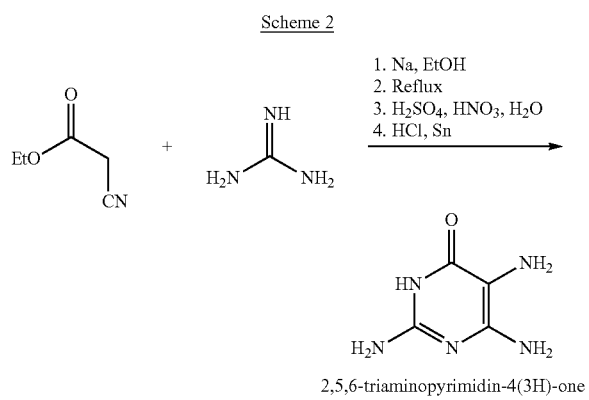

Compounds of formula (II) can also include the tautomeric structure:

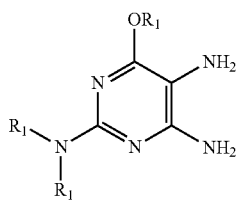

or a salt thereof.

Compounds of Formula (III):

Another embodiment of this disclosure provides the preparation of compounds of formula (III):

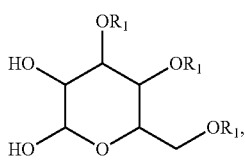

wherein each $R_1$ is independently H or a protecting group.

Formula (III) can include, for example, protected or unprotected hexose sugars. For example, a hexose sugar of formula (III) can include glucose, mannose, galactose, allose, altrose, gulose, idose, talose, and derivatives thereof. The hexoses can be in D or L form. For example, the following hexoses are included within the scope of formula (III):

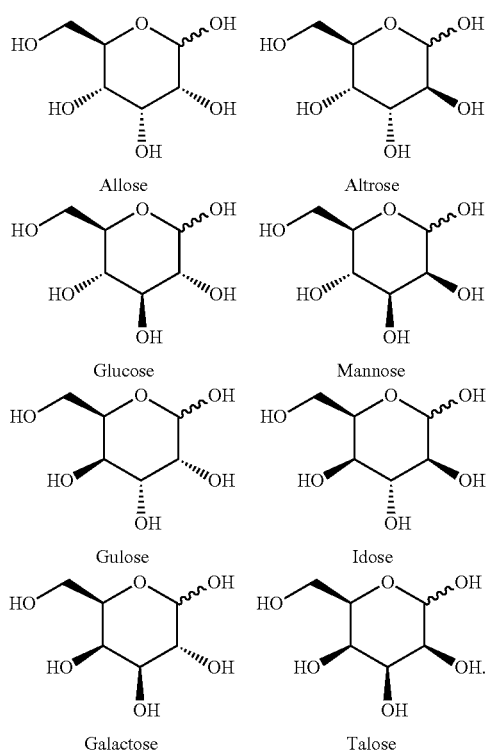

In some embodiments, the hexose is a protected or unprotected glucose or galactose. For example, the compound of formula (III) can be a protected or unprotected galactose (e.g., D-galactose). In some embodiments, the hexose is a protected or unprotected gulose or galactose.

As indicated, the compound of formula (III) may be in the form of a free sugar (i.e., an unprotected monosaccharide). Alternatively, certain hydroxyl groups of the formula (III) structure (e.g., the hydroxyl groups at the 3, 4, and 5-positions of the hexose) may be protected with an $R_1$ protecting group. For this purpose, $R_1$ may include any suitable hydroxyl functional group including, but not limited to, ether, ester, carbonate, or sulfonate protecting groups. The $R_1$ protecting groups may be the same or different.

In particular, the ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose sugar can combine to form one or more of the following protected hexoses:

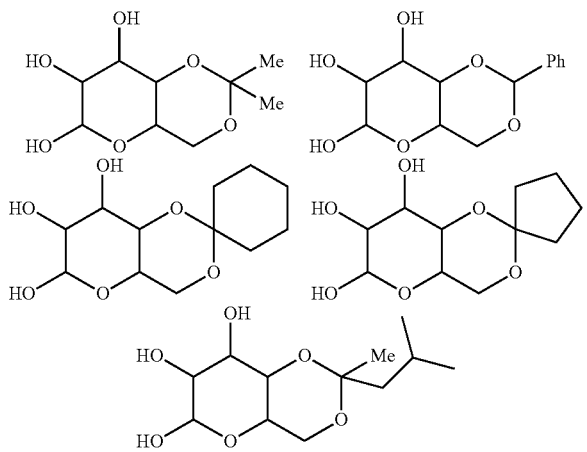

Compounds of formula (III) may be prepared according to known methods of carbohydrate synthesis. Methods of protecting carbohydrates are also known, as described in *The Organic Chemistry of Sugars*, Taylor & Francis, 2006, p. 181; and Peturssion, S. et al., *J. Chem. Educ.*, 74(11), 1297 (1997), each of which is incorporated herein by reference in its entirety.

As will be recognized by persons of ordinary skill in the art, and as discussed, infra, the stereochemistry of the formula (III) structure may govern the stereochemistry of subsequent intermediates in the synthesis of formula (I) or formula (XIII). Moreover, protection of certain hydroxyl groups can improve solubility of the formula (III) compounds and modulate stereospecificity of successive reaction steps.

Compounds of Formula (IV):

Another embodiment provided herein relates to the preparation of compounds of formula (IV):

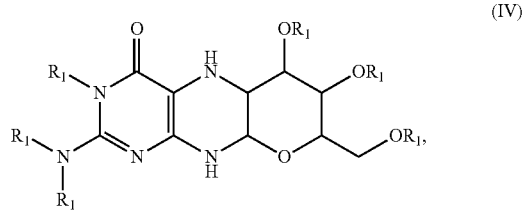

or pharmaceutically acceptable salts or hydrates thereof, wherein each $R_1$ is independently H or a protecting group.

As indicated, the amino and hydroxyl groups in the compound of formula (IV) may be in protected or unprotected form. For example, in an unprotected form, the compound for formula (IV) may include the compound 2-amino-6,7-dihydroxy-8-(hydroxymethyl)-5a,6,7,8,9a,10-hexahydro-3H-pyrano[3,2-g]pteridin-4(5H)-one:

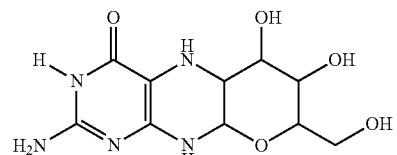

2-amino-6,7-dihydroxy-8-(hydroxymethyl)-5a,6,7,8,9a,10-hexahydro-3H-pyrano[3,2-g]pteridin-4(5H)-one, or a pharmaceutically acceptable salt, thereof.

Certain amino and/or hydroxyl groups of the formula (IV) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz) protecting groups.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

The ether protecting group may include methyl, methoxymethyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose ring component of formula (IV) can combine to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety.

Protection of certain amino and hydroxyl groups can improve solubility of the formula (IV) compounds. For example, preparation of acetyl derivatives of formula (IV) can improve solubility and increase product isolation yield.

A compound of formula (IV) may be prepared by reacting a compound of formula (II):

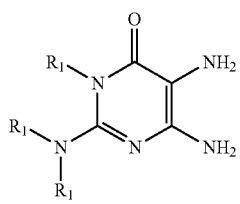

(II)

with a compound of formula (III):

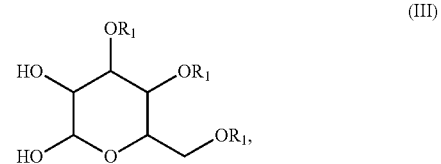

(III)

to produce a compound of formula (IV):

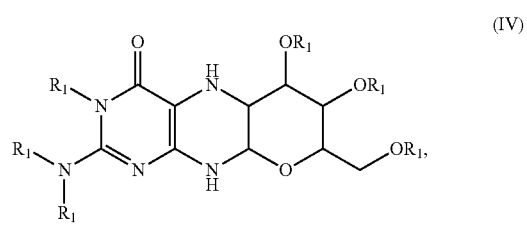

(IV)

wherein:
each $R_1$ is independently H or a protecting group, as defined above.

In particular, a compound of formula (IV) may be prepared upon reaction of a compound of formula (II) and formula (III) in the presence of any reagent which would achieve the desired cyclization. Such a reagent can be readily determined by the skilled person and can include, for example, substituted or unsubstituted hydrazines. Non-limiting examples of suitable hydrazine reagents include phenylhydrazines and alkylhydrazines, for example, phenylhydrazine and p-nitrophenylhydrazine.

As will be understood, the isomeric form of the formula (IV) structure may govern the stereospecificity of subsequent intermediates in the successive steps of the synthesis of formula (I) or formula (XIII). Accordingly, a particular isomer may be isolated at this step of the synthesis or, alternatively, isomeric mixtures of formula (IV) may be carried through and isolated at later stages of the synthesis.

In some embodiments, the compound of formula (IV) includes the isomer:

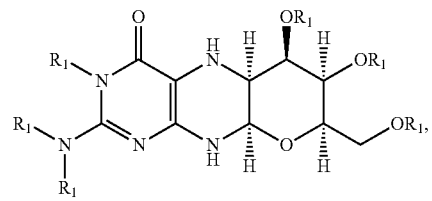

or pharmaceutically acceptable salts or hydrates thereof.

During the synthesis, the stereochemistry of the formula (IV) product may optionally be controlled by manipulating the stereochemistry of the C-3 and C-4 positions of the formula (III) hexose. For example, formula (III) reactants derived from glucose, mannose, galactose, allose, altrose, gulose, idose, and talose, and derivatives which differ with respect to the stereochemistry of the C-3 and C-4 positions of the sugar will produce different isomer mixtures of the formula (IV) product.

The stereoselectivity of the formula (IV) synthesis can also be controlled by incorporating bulky protecting groups at certain positions of the formula (III) compound. For example, introducing an isopropylidine acetal at any of the C-3, C-4, or C-5 positions of the formula (III) sugar can modulate stereoselectivity of the reaction.

Compounds of Formula (V):

Another embodiment provided herein relates to the preparation of compounds of formula (V):

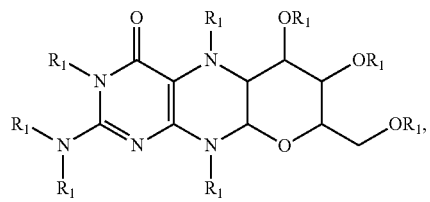

(V)

or pharmaceutically acceptable salts or hydrates thereof, wherein each $R_1$ is independently H or a protecting group. For example, the compound of formula (V) includes the compound (V-A), (V-B), and (V-C):

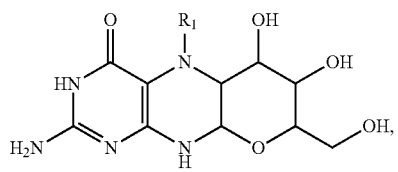

(V-A)

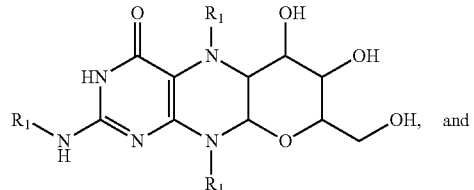

(V-B)

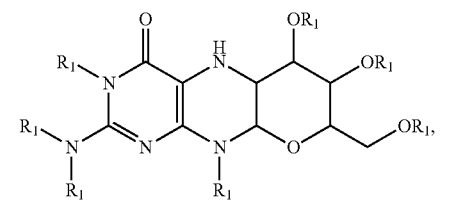

(V-C)

or a pharmaceutically acceptable salt thereof, wherein $R_1$ is H or a protecting group. The compound of formula (V) also includes, for example, the compound (9H-fluoren-9-yl)methyl 2-amino-6,7-dihydroxy-8-(hydroxymethyl)-4-oxo-5a,6,7,8,9a,10-hexahydro-3H-pyrano[3,2-g]pteridine-5(4H)-carboxylate:

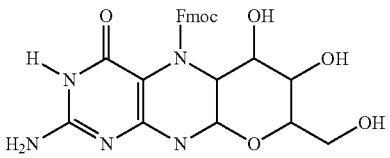

(9H-fluoren-9-yl)methyl 2-amino-6,7-dihydroxy-8-(hydroxymethyl)-4-oxo-5a,6,7,8,9a,10-hexahydro-3H-pyrano[3,2-g]pteridine-5-(4H)-carboxylate, or a pharmaceutically acceptable salt thereof. In some embodiments, the compound of formula (V) can include, for example, one or more of the following compounds:

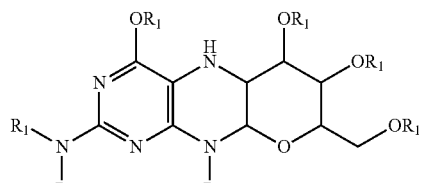

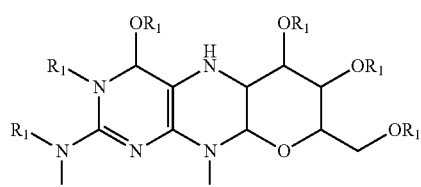

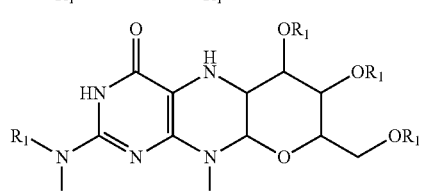

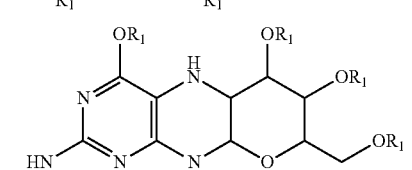

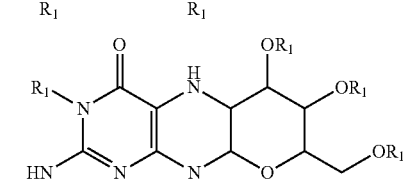

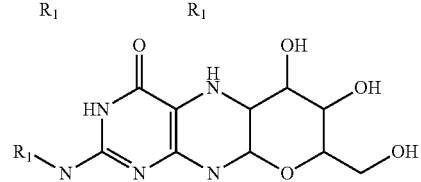

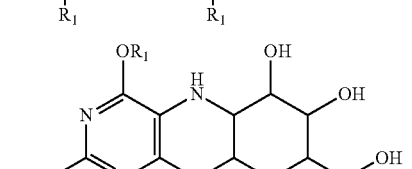

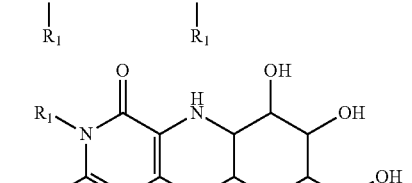

or a pharmaceutically acceptable salt thereof. For example, a compound of formula (V) can include one or more of:

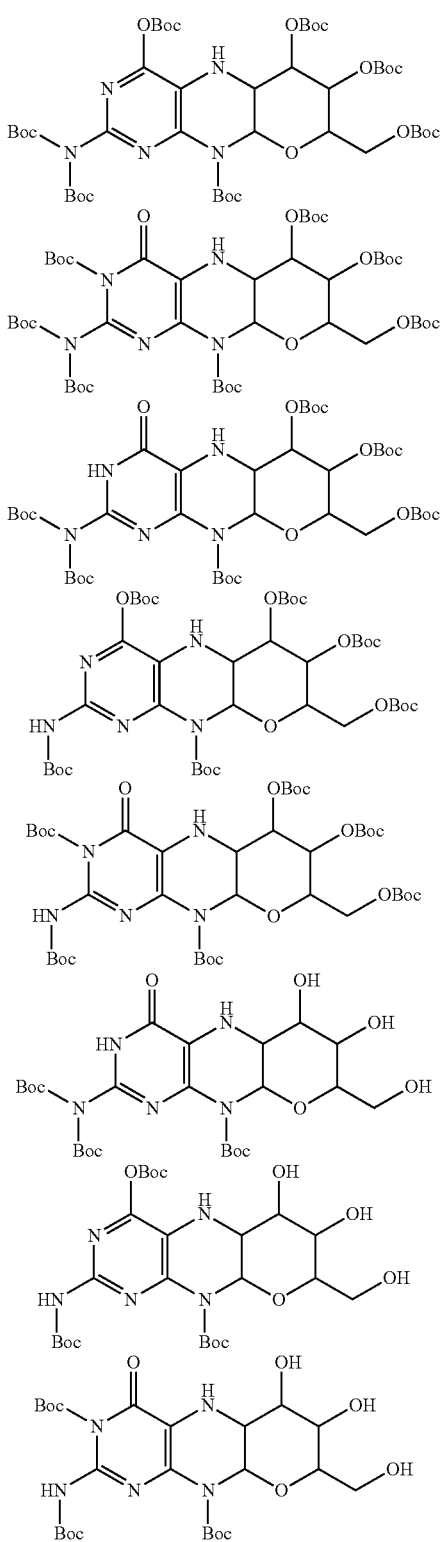

or a pharmaceutically acceptable salt thereof.

In some embodiments, one or more of the above compounds can be separated by those skilled in the art by a variety of methods, including high performance liquid chromatography (HPLC) ("Preparative LC-MS Purification: Improved Compound Specific Method Optimization" K. F. Blom, et al., J. Combi. Chem. 6(6), 874 (2004), which is incorporated herein by reference in its entirety) and normal phase silica chromatography.

As indicated, certain amino and/or hydroxyl groups of the formula (V) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolylcarbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz) protecting groups.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose ring component of formula (V) can combine to form an an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety.

Protection of certain amino and hydroxyl groups can improve solubility of the formula (V) compounds. For example, preparation of acetyl derivatives of formula (V) can improve solubility and increase product isolation yield.

A compound of formula (V) may be prepared by selectively protecting a compound of formula (IV):

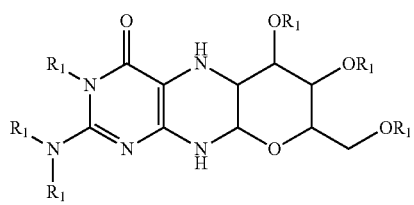

(IV)

to prepare a compound of formula (V):

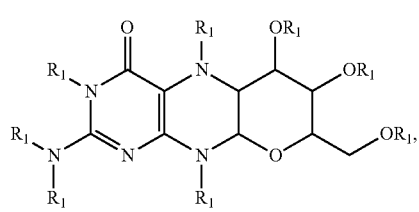

(V)

wherein:
each $R_1$ is independently H or a protecting group, as defined above.

In particular, a compound of formula (V) may be prepared by reacting a compound of formula (IV) with any reagent and using conditions to achieve selective installation of the $R_1$ protecting group at N-5. Suitable reagents and conditions for installing the $R_1$ protecting group can be readily determined by those of ordinary skill in the art. For example, 9-fluorenylmethyl carbamate (Fmoc) can be installed using an activated chloride derivative, as reported by E. Atherton et al., "The Fluorenylmethoxycarbonyl Amino Protecting Group," in The Peptides, S. Udenfriend and J. Meienhofer, Eds., Academic Press, New York, 1987, Vol. 9, page 1. Protection using t-butyl carbamate (Boc) is attained by reacting a compound of formula (IV) with, for example, (Boc)$_2$O in aqueous NaOH as described by D. Tarbell et al., *Proc. Natl. Acad. Sci., USA*, 69, 730 (1972). Methyl and ethyl carbamate can be readily introduced as described by E. J. Corey et al., *Tetrahedron Lett.*, 19(12), 1051 (1978).

As will be understood, the isomeric form of the formula (V) structure may govern the stereospecificity of subsequent intermediates in the successive steps of the synthesis of formula (I) or formula (XIII). Accordingly, a particular isomer may be isolated at this step of the synthesis or, alternatively, isomeric mixtures of formula (V) may be carried through and isolated at later stages of the synthesis.

In some embodiments, the compound of formula (V) includes the isomer:

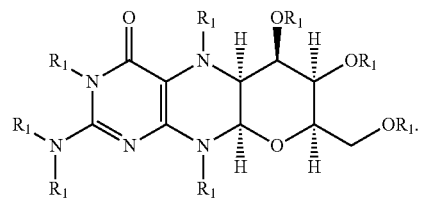

In addition, as shown above, the compound of formula (V) also includes the tautomeric structure:

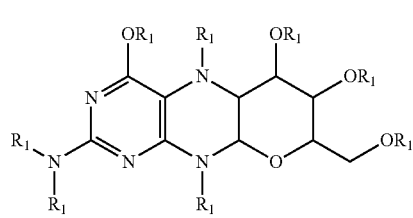

(V)

or a salt thereof.

Compounds of Formula (VI):

In another embodiment, compounds of formula (VI) are prepared:

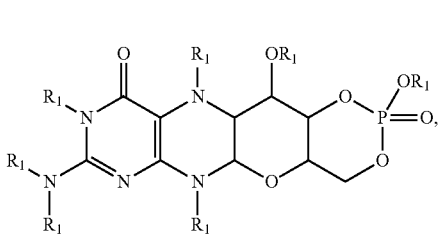

(VI)

or pharmaceutically acceptable salts or hydrates thereof, wherein each $R_1$ is independently H or a protecting group. For example, the compound for formula (VI) includes the compound (VI-A):

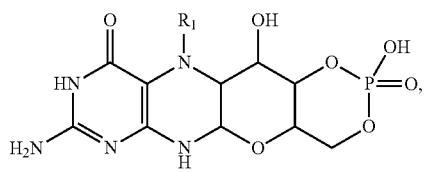

(VI-A)

or a pharmaceutically acceptable salt thereof, wherein $R_1$ is H or a protecting group. The compound of formula (VI) also includes, for example, the compound:

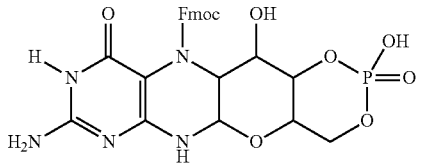

(9H-fluoren-9-yl)methyl 8-amino-2, 12-dihydroxy-10-oxo-4, 4a,5a,6,9,10,12,12a-octahydro-[1,3,2]dioxaphosphinino [4′,5′:5,6]pyrano[3,2-g]pteridine-11(11aH)-carboxylate 2-oxide, or a pharmaceutically acceptable salt thereof. In some embodiments, the compound of formula (VI) includes, for example, the compound (VI-B):

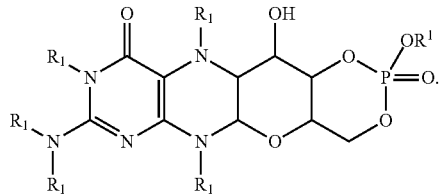

(VI-B)

or a pharmaceutically acceptable salt thereof. In some embodiments, the compound of formula (VI) includes, for example, the compound (VI-C):

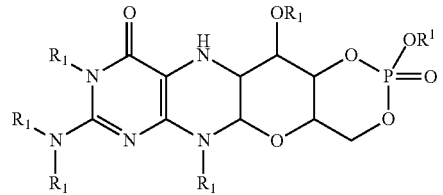

(VI-C)

or a pharmaceutically acceptable salt thereof. In some embodiments, the compound of formula (VI) can include one or more of:

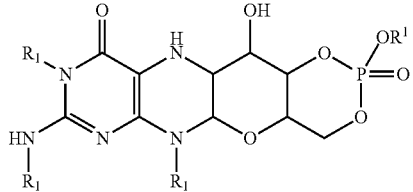

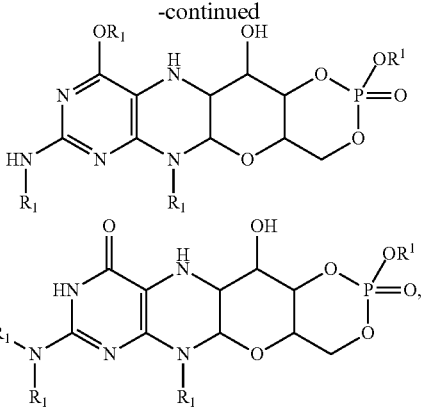

or a pharmaceutically acceptable salt thereof. For example, a compound of formula (VI) can include one or more of the following:

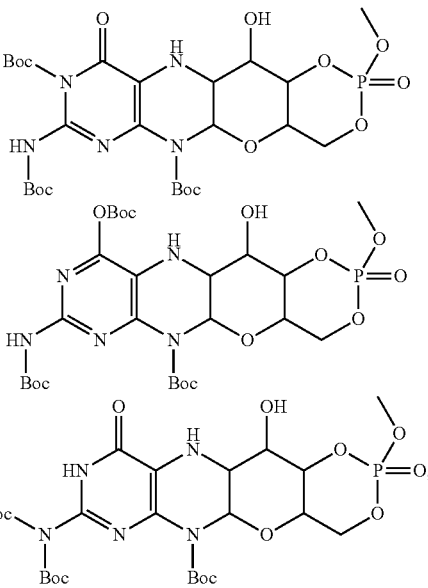

or a pharmaceutically acceptable salt thereof. In some embodiments, one or more of the above compounds can be separated by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

As indicated, certain amino and/or hydroxyl groups of the formula (VI) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, a carbamate protecting group can be chosen from 9-fluorenylmethyl carbamate (Fmoc), t-butyl carbamate (Boc), and carboxybenzyl carbamate (cbz) protecting groups.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

The ether protecting group may include methyl, methoxymethyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

Protection of certain amino and hydroxyl groups can improve solubility of the formula (VI) compounds. For example, preparation of acetyl derivatives of formula (VI) can improve solubility and increase product isolation yield.

A compound of formula (VI) may be prepared by phosphorylating a compound of formula (V):

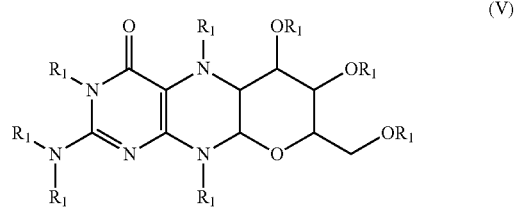

(V)

to prepare a compound of formula (VI):

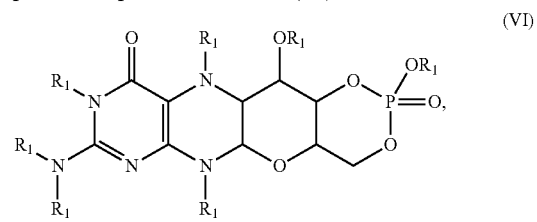

(VI)

or a pharmaceutically acceptable salt form thereof, wherein each $R_1$ is independently H or a protecting group, as defined above.

In particular, a compound of formula (VI) may be prepared by reacting a compound of formula (V) with any phosphorylating agent proper to form a compound of formula (VI). Suitable phosphorylation reagents and conditions can be readily determined by those of ordinary skill in the art. For example, a compound of formula (VI) may be achieved by treating a compound of formula (V) with a P(V) phosphorylating agent. Suitable P(V) phosphorylating agents include, but are not limited to, $POCl_3$, $H_3PO_4$, $PO(OBn)_xCl_{3-x}$, $Cl_3CCH_2OP(O)Cl_2$, $PO(OCH_3)_xCl_{3-x}$, $PO(OCH_3)Cl_2$, $PO(OCH_3)_xCl_{3-x}$, $PO(OCH_3)Cl_2$, and $(BnO)_2P(O)OP(O)(OBn)_2$. In some embodiments, the P(V) phosphorylating agent is $POCl_3$.

In one embodiment, the phosphorylation reaction is carried out by treating a compound of formula (V) with $POCl_3$ at ambient temperature to afford a compound of formula (VI). In another embodiment, a compound of formula (VI) is formed by treating a compound of formula (V) with $POCl_3$ at 60° C.

The phosphorylation reaction may also involve treating a compound of formula (V) with a P(III) phosphitylating agent to form a phosphite intermediate. Suitable P(III) phosphitylating agents include, for example, $P(OCH_2CH_2CN)_2Cl$; $P(OCH_2CH_2CN)(NPr_2-i)Cl$; and cyanoethyl-O—P[N(i-Pr)$_2$]$_2$. When a P(III) phosphitylating agent is used for phosphorylation, subsequent oxidation may be used to furnish the corresponding phosphate. When P(III) reagents are employed for the synthesis of a compound of formula (VI), Boc or Cbz groups may be used for $R_1$ protection of the N-5 of the compound of formula (IV) due to the basic environment used for phosphitylation.

As will be understood, the isomeric form of the formula (VI) structure may regulate the stereospecificity of successive steps in the synthesis of formula (I). Accordingly, a particular isomer may be isolated at this step of the synthesis or, alternatively, isomeric mixtures of a compound of formula (VI) may be carried through and isolated at later stages of the synthesis.

In some embodiments, the compound of formula (VI) includes the isomer:

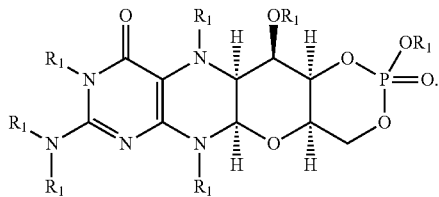

As shown above, the compound of formula (VI) can also include the tautomeric structure.

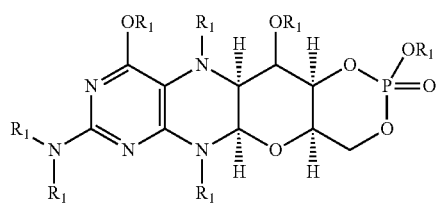

or a salt thereof.

Compounds of Formula (VII):

In another embodiment, compounds of formula (VII) are prepared:

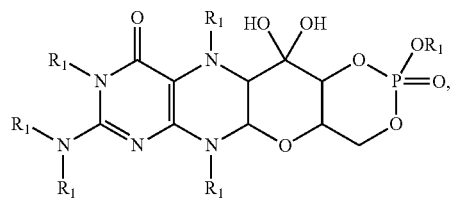

(VII)

or pharmaceutically acceptable salts or hydrates thereof, wherein each $R_1$ is independently H or a protecting group. For example, the compound for formula (VII) includes the compound (VII-A):

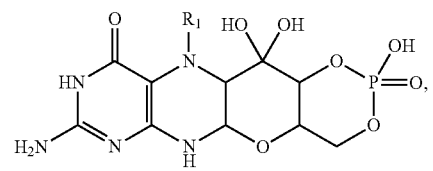

(VII-A)

or a pharmaceutically acceptable salt thereof, wherein $R_1$ is H or a protecting group. The compound of formula (VII) also includes, for example, the compound:

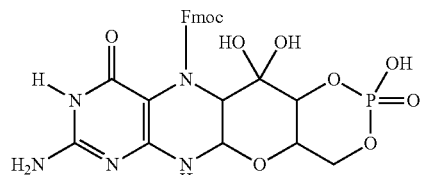

(9H-fluoren-9-yl)methyl 8-amino-2,12,
12-trihydroxy-10-oxo-4,4a,5a,6,9,10,12,12a-octahydro-
[1,3,2]dioxaphosphinino[4',5':5,6]pyrano[3,2-g]pteridine-
11(11aH)-carboxylate 2-oxide or a pharmaceutically acceptable salt thereof. In some embodiments, the compound of formula (VII) includes the compound (VII-B):

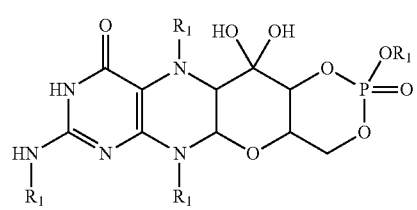

(VII-B)

or a pharmaceutically acceptable salt thereof. In some embodiments, the compound of formula (VII) includes the compound (VII-C):

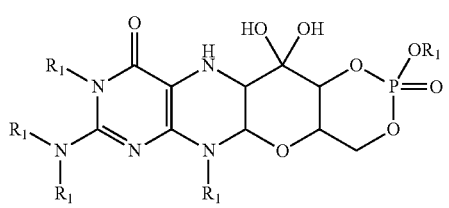

(VII-C)

or a pharmaceutically acceptable salt thereof. In some embodiments, a compound of formula (VII) can include one or more of the following:

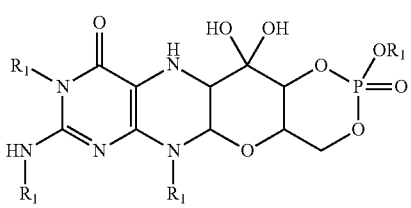

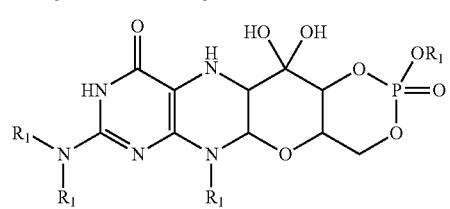

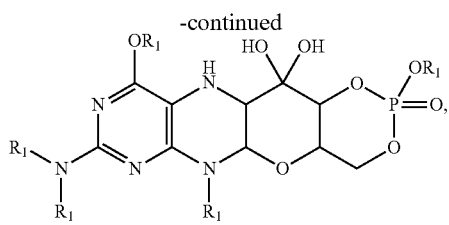

or a pharmaceutically acceptable salt thereof. For example, a compound of formula (VII) can include one or more of the following:

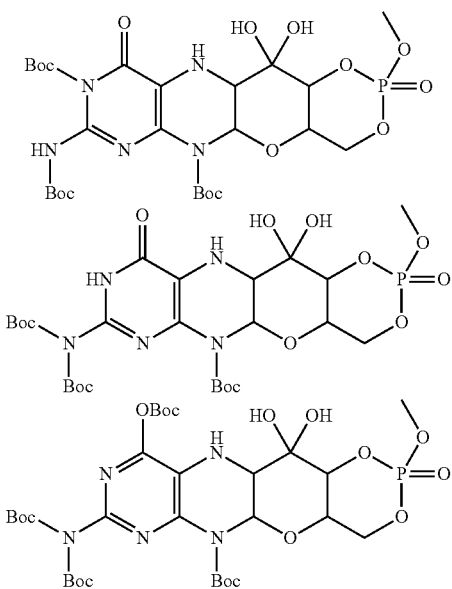

or a pharmaceutically acceptable salt thereof. In some embodiments, one or more of the above compounds can be separated by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

As indicated, certain amino and/or hydroxyl groups of the formula (VII) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, the carbamate protecting group is chosen from 9-fluorenylmethyl carbamate (Fmoc), t-butyl carbamate (Boc), and carboxybenzyl carbamate (cbz) protecting groups.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetate, aryl formate, aryl acetate, aryl levulinate, aryl pivaloate, aryl benzoate, and aryl 9-fluoroenecarboxylate.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

Protection of certain amino and hydroxyl groups can improve solubility of the formula (VII) compounds. For example, preparation of acetyl derivatives of formula (VII) compounds can improve solubility and increase product isolation yield.

A compound of formula (VII) may be prepared by oxidizing the compound of formula (VI):

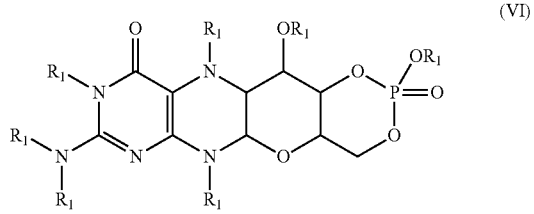
(VI)

to prepare a compound of formula (VII):

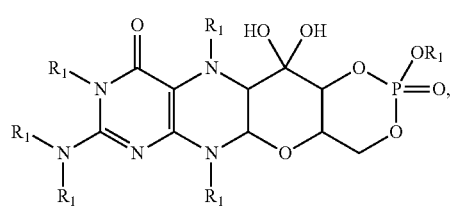
(VII)

wherein:
each $R_1$ is independently H or a protecting group, as defined above.

In this synthesis, a compound of formula (VII) may be prepared by reacting a compound of formula (VI) with any oxidizing agent proper to selectively form the diol of formula (VII). Suitable oxidizing agents and conditions can be readily determined by those of ordinary skill in the art. For example, a compound of formula (VII) may be formed upon treatment of a compound of formula (VI) with a ruthenium compound, such as $RuO_4^-$/NMO. Other oxidants, such as Dess-Martin's reagent, DMSO/triflic anhydride, TFAA/DMSO, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridyldisulfide (DPS), and osmium tetroxide may also be used. In one embodiment, the oxidation conditions are performed so that the pyrazine ring of compound (VI) is not oxidized. In some embodiments, the oxidizing agent is chosen from $RuO_4^-$/NMO, Dess-Martin's reagent, DMSO/triflic anhydride, and PDC.

For example, the oxidation reaction may be carried out by treating a compound of formula (VI) with $RuO_4^-$/NMO at ambient temperature to afford a compound of formula (VII). In another embodiment, a compound of formula (VII) is formed by treating a compound of formula (VI) with $RuO_4^-$/NMO at a temperature from 20-60° C., or at 20, 25, 30, 35, 40, 45, 50, or 55° C.

A compound of formula (VII) can be used to prepare a compound of formula (XIV) via dehydration. Suitable reaction conditions for such a dehydration reaction are readily determined by those of ordinary skill in the art. For example, a compound of formula (VII) can be combined with a concentrated acid or base to prepare a compound of formula (XIV). In some embodiments, any of the oxidation methods provided herein can include the further step of dehydrating the reaction product to obtain the corresponding ketone.

As will be understood, the isomeric form of the formula (VII) structure may regulate the stereospecificity of successive steps in the synthesis of formula (I). Accordingly, a particular isomer may be isolated at this step of the synthesis or, alternatively, isomeric mixtures of a compound of formula (VII) may be carried through and isolated at later stages of the synthesis.

In some embodiments, the compound of formula (VII) includes the isomer:

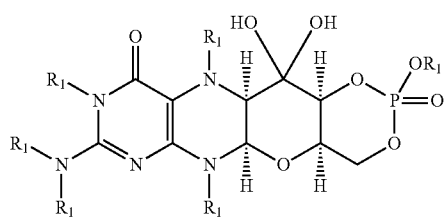

or a pharmaceutically acceptable salt thereof. As shown above, the compound of formula (VII) can also include the tautomeric structure:

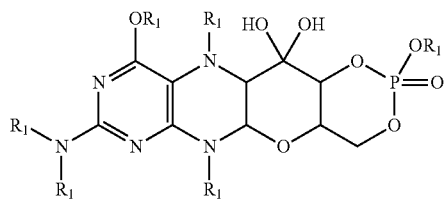

or a pharmaceutically acceptable salt thereof.

Compound of Formula (I):

In some embodiments, the preparation of a compound of formula (I):

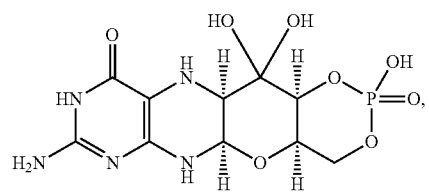 [SMILES: Nc1nc2c(c(=O)[nH]1)N[C@@H]1[C@H](N2)O[C@@H]2COP(=O)(O)O[C@@H]2C1(O)O]

and pharmaceutically acceptable salts and hydrates thereof is provided. The compound of formula (I) also includes the tautomeric structure:

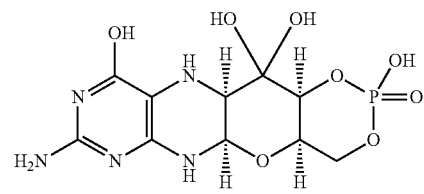 [SMILES: Nc1nc(O)c2c(n1)N[C@@H]1O[C@@H]3COP(=O)(O)O[C@@H]3C(O)(O)[C@@H]1N2]

or a pharmaceutically acceptable salt thereof.

The synthesis of the compound of formula (I) is preferably carried out so as to achieve the desired stereochemistry and avoid oxidation due to pyran ring opening during the chemical synthesis.

The compound of formula (I) may be prepared, for example, by deprotecting the compound of formula (VII):

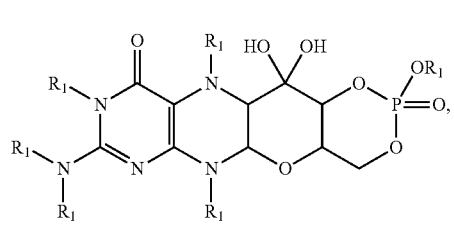
(VII)

wherein each $R_1$ is independently H or a protecting group, as defined above, to prepare the compound of formula (I).

In this synthesis, the deprotection may involve, for example, either sequential or one-pot deprotection of certain amino and hydroxyl protecting groups on a compound of formula (VII) to furnish the compound of formula (I). Suitable reagents and conditions for the deprotection of a compound of formula (VII) can be readily determined by those of ordinary skill in the art. For example, compound (I) may be formed upon treatment of a compound of formula (VII) under conditions so that hydroxyl protecting groups, such as acetate, isopropylidine, and benzylidine protecting groups, are removed from the formula (VII) structure. The acetate group can be cleaved, for example, under Zemplén conditions using catalytic NaOMe as a base in methanol. The benzylidene and isopropylidene groups can be cleaved by hydrogenation or using acidic hydrolysis as reported by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the compound of formula (VII). 9-fluorenylmethyl carbamate (Fmoc) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J. Org. Chem.*, 43, 2285 (1978), under acidic conditions (e.g., 3 M HCl in EtOAc). Hydrogenation can be used to cleave the carboxybenzyl carbamate (cbz) protecting group as described by J. Meienhofer et al., *Tetrahedron Lett.*, 29, 2983 (1988).

To prevent oxidation of formula (I) during the reaction, the deprotection may be performed under anaerobic conditions. The deprotection may also be performed at ambient temperature or at temperatures of from about 20-60° C. (e.g., 25, 30, 35, 40, 45, 50, or 55° C.).

The compound of formula (I) may be isolated in the form of a pharmaceutically acceptable salt. For example, the compound of formula (I) may be crystallized in the presence of HCl to form the HCl salt form of the compound. In some embodiments, the compound of formula (I) may be crystallized as the HBr salt form of the compound. The compound of formula (I) may also be isolated, e.g., by precipitation as a sodium salt by treating with NaOH. The compound of formula (I) is labile under certain reaction and storage conditions. In some embodiments, the final solution comprising the compound of formula (I) may be acidified by methods known in the art. For example, the compound of formula (I), if stored in solution, can be stored in an acidic solution.

In some embodiments, the compound of formula (I) may be prepared, for example, by: reacting a compound of formula (II-A):

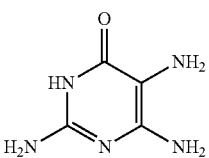
(II-A)

with a compound of formula (III-A):

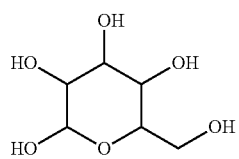
(III-A)

in the presence of a hydrazine to produce a compound of formula (IV-A):

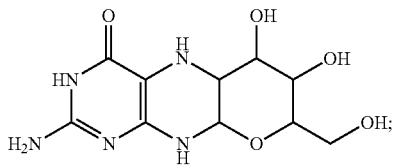
(IV-A)

selectively protecting the compound of formula (IV-A) to prepare a compound of formula (V-A):

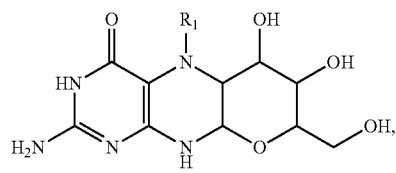
(V-A)

wherein:
$R_1$ is a protecting group, as defined above;
phosphorylating the compound of formula (V-A) to prepare a compound of formula (VI-A):

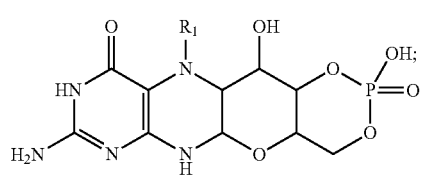
(VI-A)

oxidizing the compound of formula (VI-A) to prepare a compound of formula (VII-A):

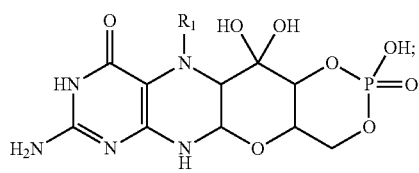

(VII-A)

and deprotecting the compound of formula (VII-A) to prepare the compound of formula (I). For example, a compound of formula (I) can be prepared as shown in Scheme 3.

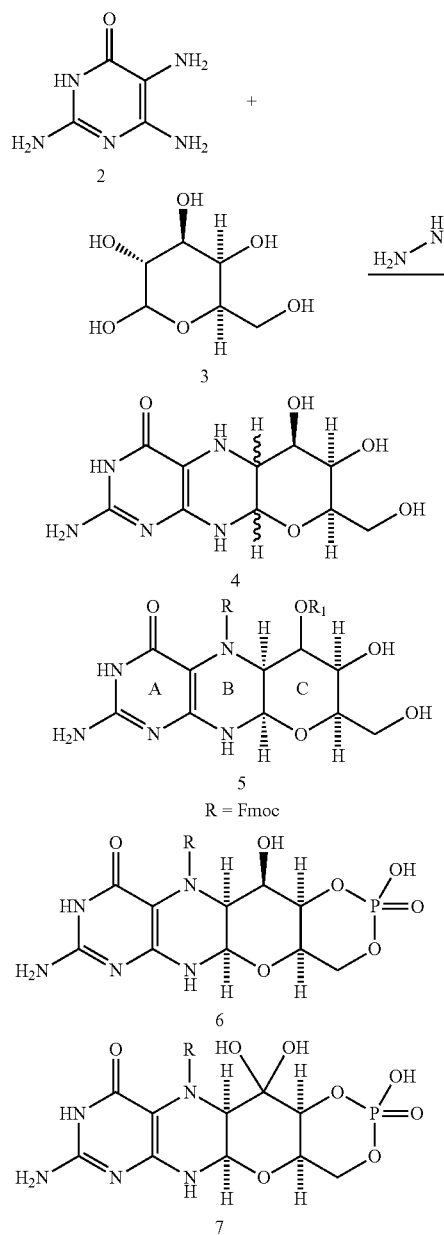

Scheme 3.

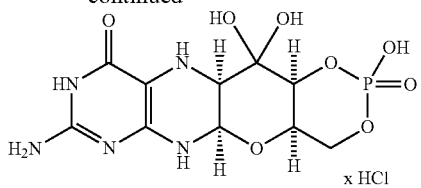

cPMP

In another embodiment, the compound of formula (I) is prepared by: reacting a compound of formula (II-A):

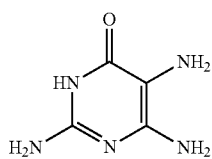

(II-A)

with a compound of formula (III-A):

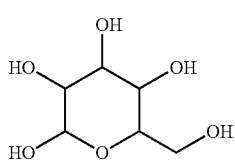

(III-A)

in the presence of a hydrazine to produce a compound of formula (IV-A):

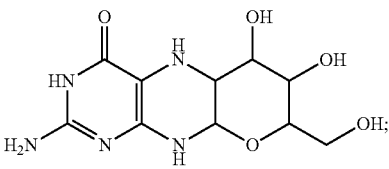

(IV-A)

selectively protecting the compound of formula (IV-A) to prepare a compound of formula (V-B):

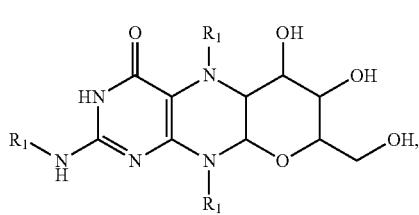

(V-B)

wherein:

each $R_1$ is independently a protecting group, as defined above;

phosphorylating the compound of formula (V-B) to prepare a compound of formula (VI-B):

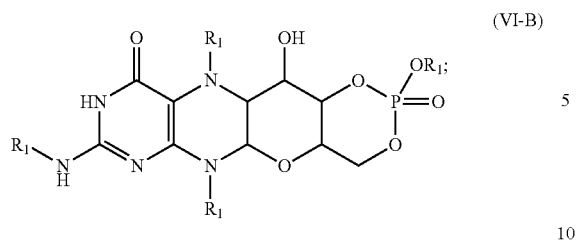
(VI-B)
oxidizing the compound of formula (VI-B) to prepare a compound of formula (VII-B):
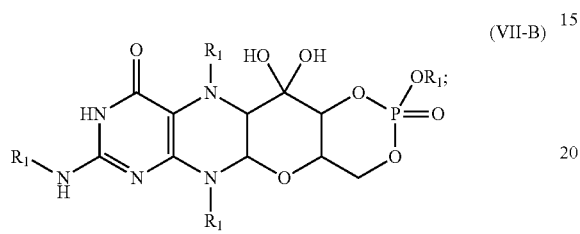
(VII-B)
and deprotecting the compound of formula (VII-B) to prepare the compound of formula (I). For example, a compound of formula (I) can be prepared as shown in Scheme 4.

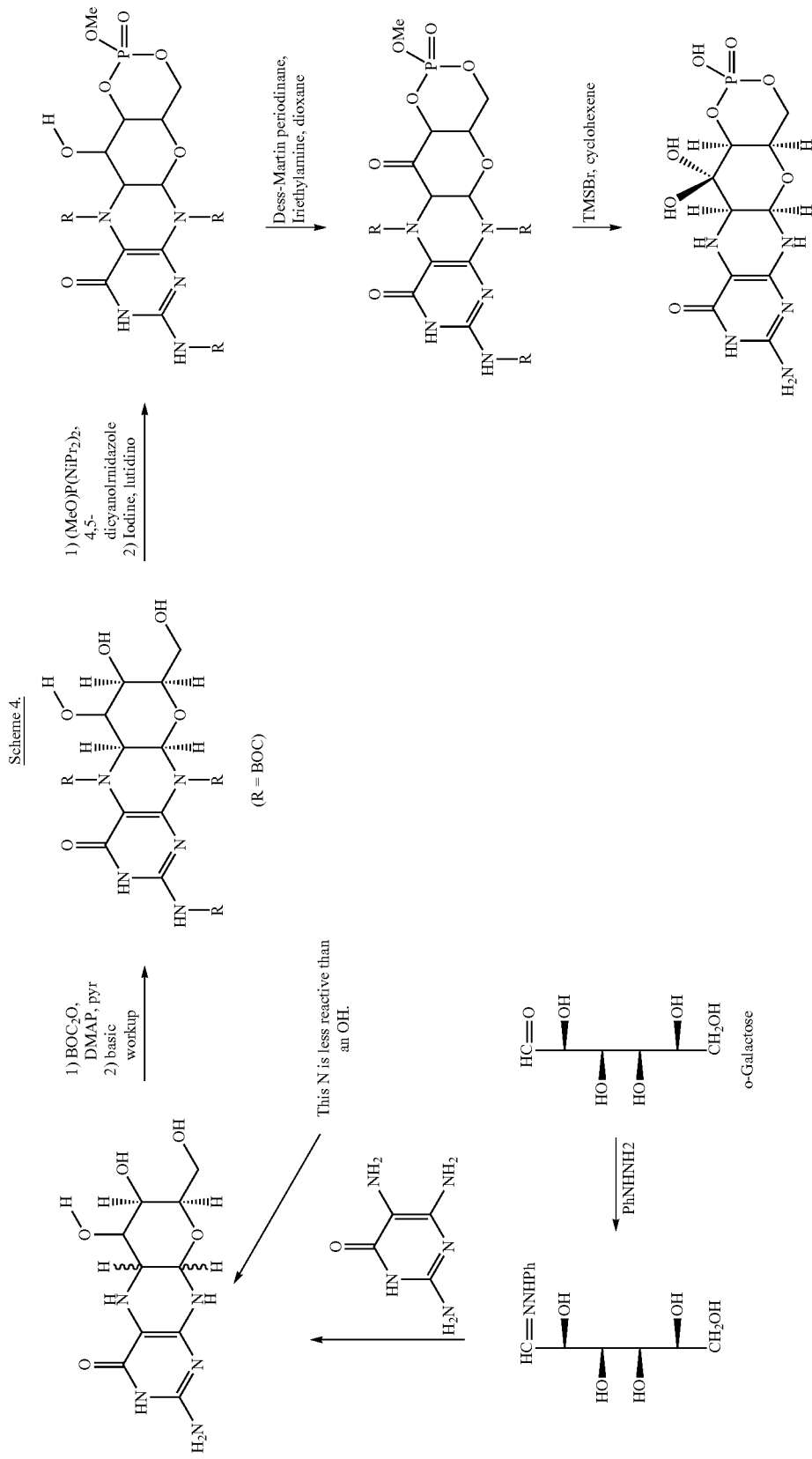

Alternatively, a compound of formula (I) can be formed as shown in Scheme 5. A diaminopyrimidinone compound of formula (II) can be coupled with a phosphorylated hexose sugar of formula (VIII), to give a compound of formula (IX). The piperizine ring nitrogen atoms can be protected to give a compound of formula (X) which can be oxidized to give a diol of formula (XI). The diol of formula (XI) can then be deprotected using appropriate conditions and converted to the compound of formula (I).

In this embodiment, the phosphate may be introduced at the beginning of the synthesis to avoid undesirable equilibrium between the pyrano and furano isomers during subsequent steps of the synthesis. For example, a compound of formula (I) can be prepared as shown in Scheme 6.

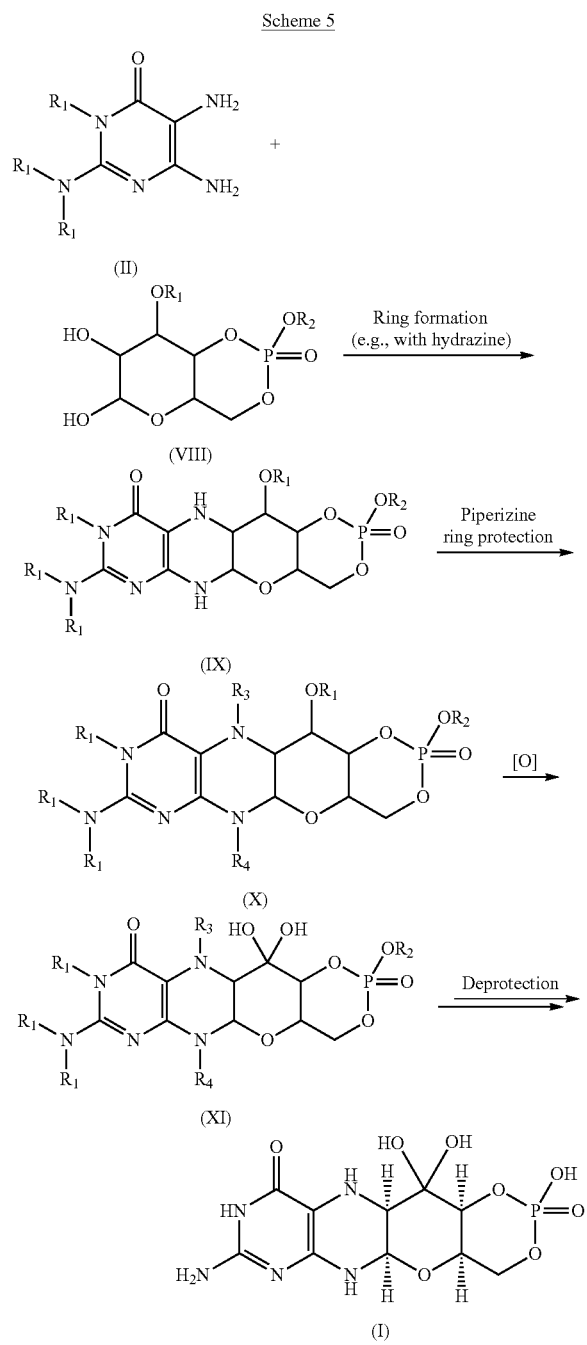

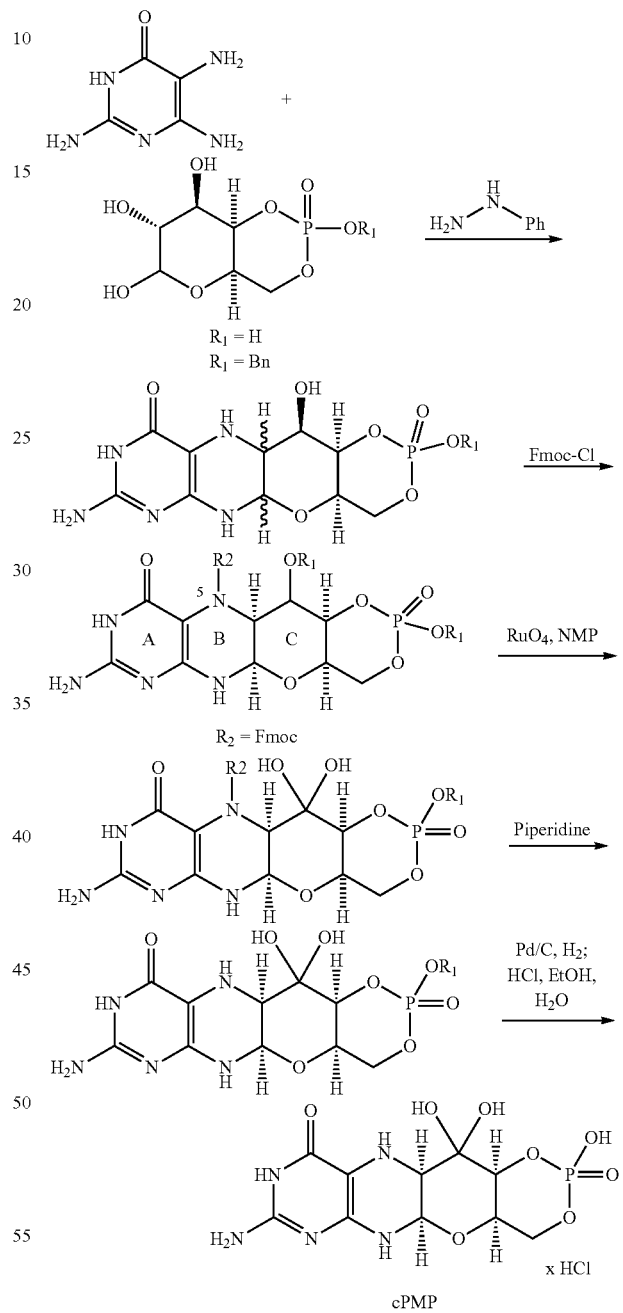

A compound of formula (I) can also be formed as shown in Scheme 7. A diaminopyrimidinone compound of formula (II) can be coupled to a compound of formula (III) to afford the piperizine derivative of formula (IV). The piperizine ring nitrogen atoms of the compound of formula (IV) can be protected under standard conditions to give a derivative of formula (V). The formula (V) structure can be oxidized to afford compounds of formula (XII). Phosphorylation of a compound of formula (XII) gives a compound of formula (VII). Global deprotection of the compound of formula (VII) can afford the compound of formula (I).

For example, a compound of formula (I) can be prepared as shown in Scheme 8.

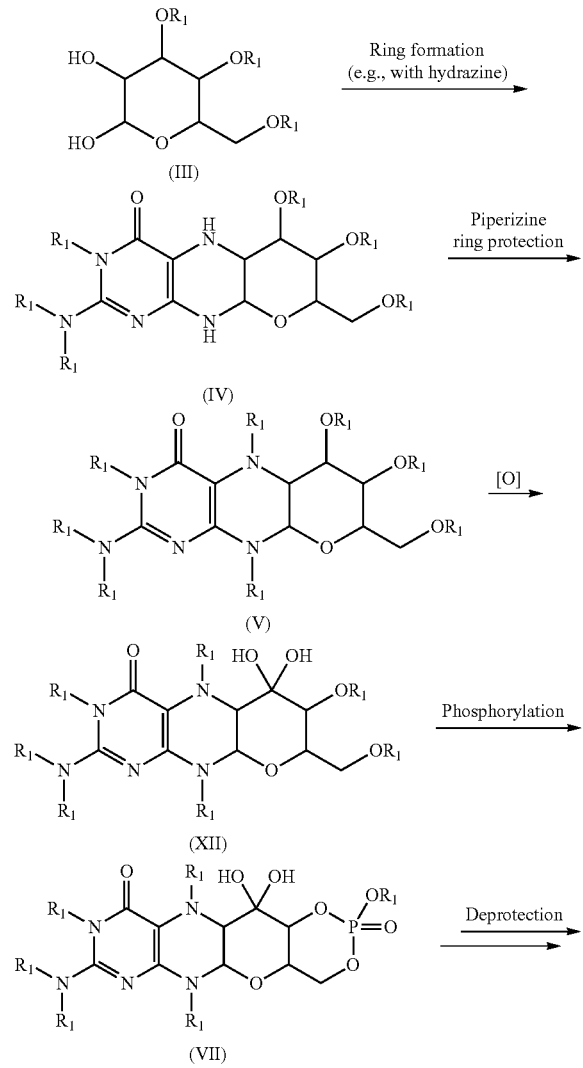

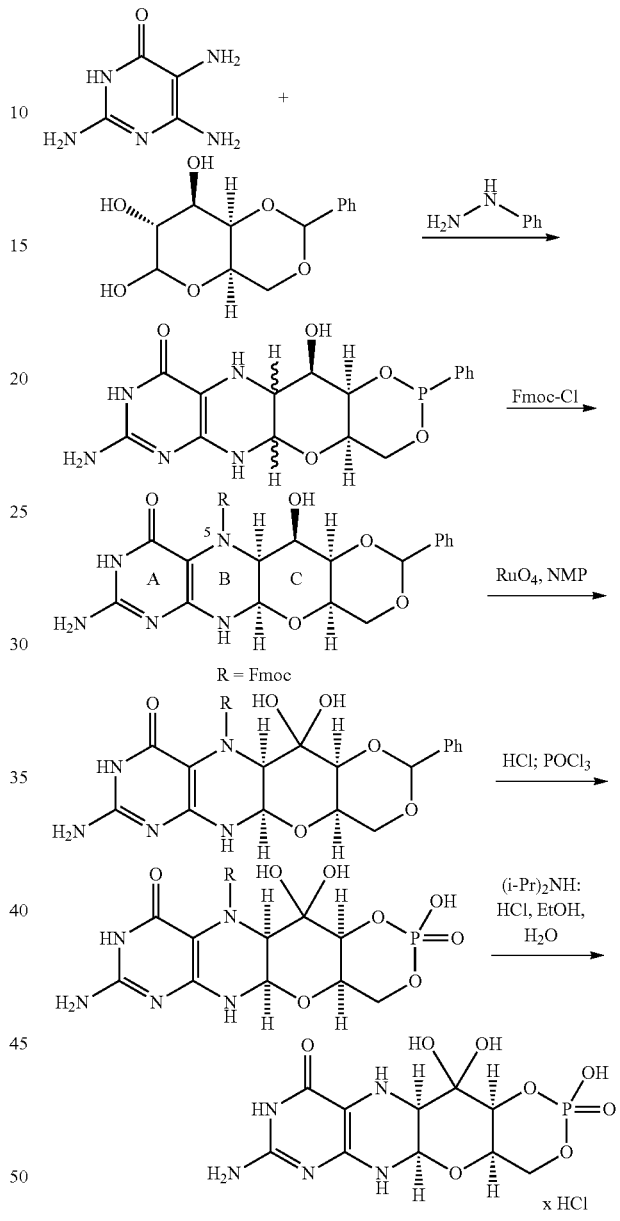

In an alternative embodiment, the compound of formula (I) can be formed as shown in Scheme 9. A diaminopyrimidinone compound of formula (II) can be condensed with a 2-carbonyl hexose building block of formula (XVIII) to produce an imine of formula (XX) with good regioselectivity. Further activation of a functional group at the anomeric position (such as an acetate) by a Lewis acid (LA) (e.g., TMSOTf) will furnish a cyclized compound of formula (XXI). The newly generated glycosidic bond may be in an equatorial position. Hydrogenation of a compound of formula (XXI) can produce a compound of formula (IV). Selective protection of a compound of formula (IV) gives a compound or formula (V) which is oxidized to give a compound of formula (XII). A compound of formula (XII) can then be treated as described herein to furnish the compound of formula (I).

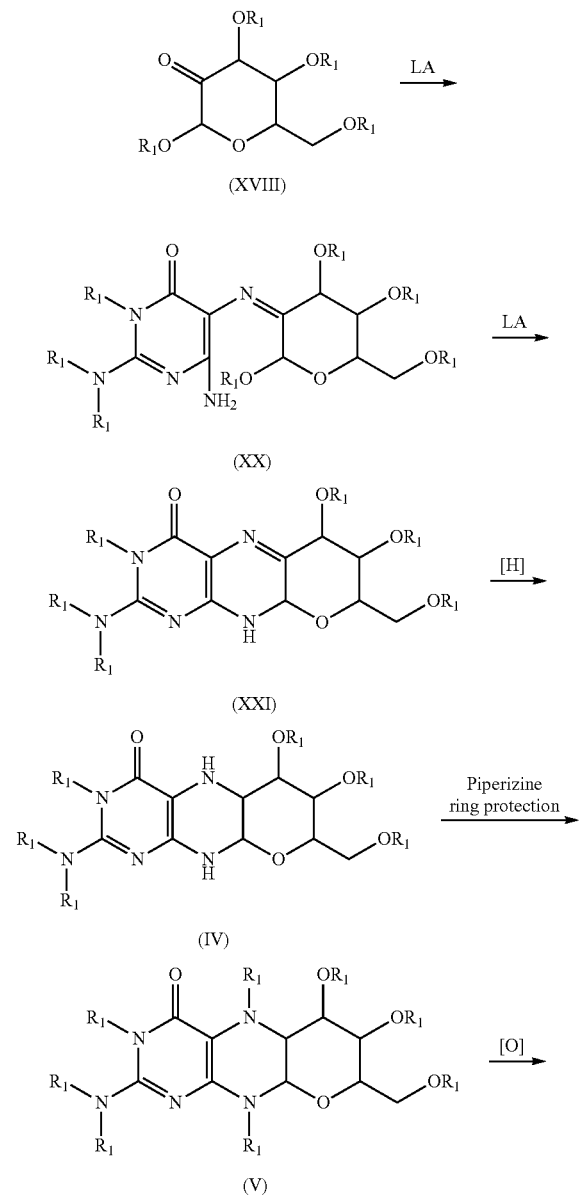

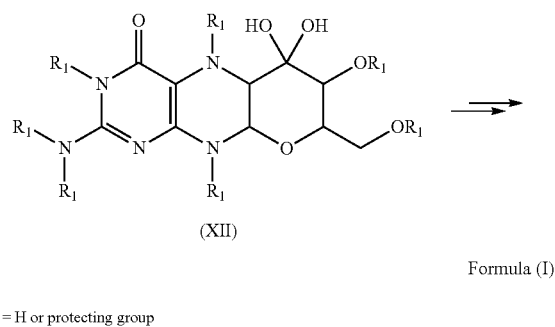

$R_1$ = H or protecting group

For example, a compound of formula (I) can be prepared as shown in Scheme 10.

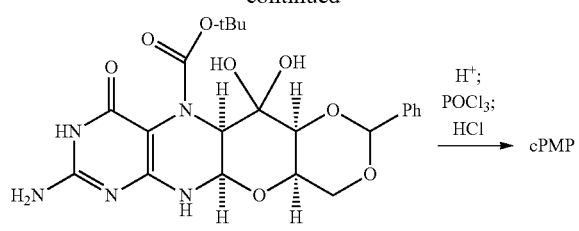

Alternatively, the compound of formula (I) can be formed as shown in Scheme 11. In this synthesis, the cyclization of a diaminopyrimidinone of formula (II) with a hexose building block can be carried out in the presence of base. Activation with a Lewis Acid (LA) affords a cyclic product, which can be deprotected to form an unprotected ketone. The ketone may be phosphorylated and/or globally deprotected as described herein to produce the compound of formula (I) or a compound of formula (XIII).

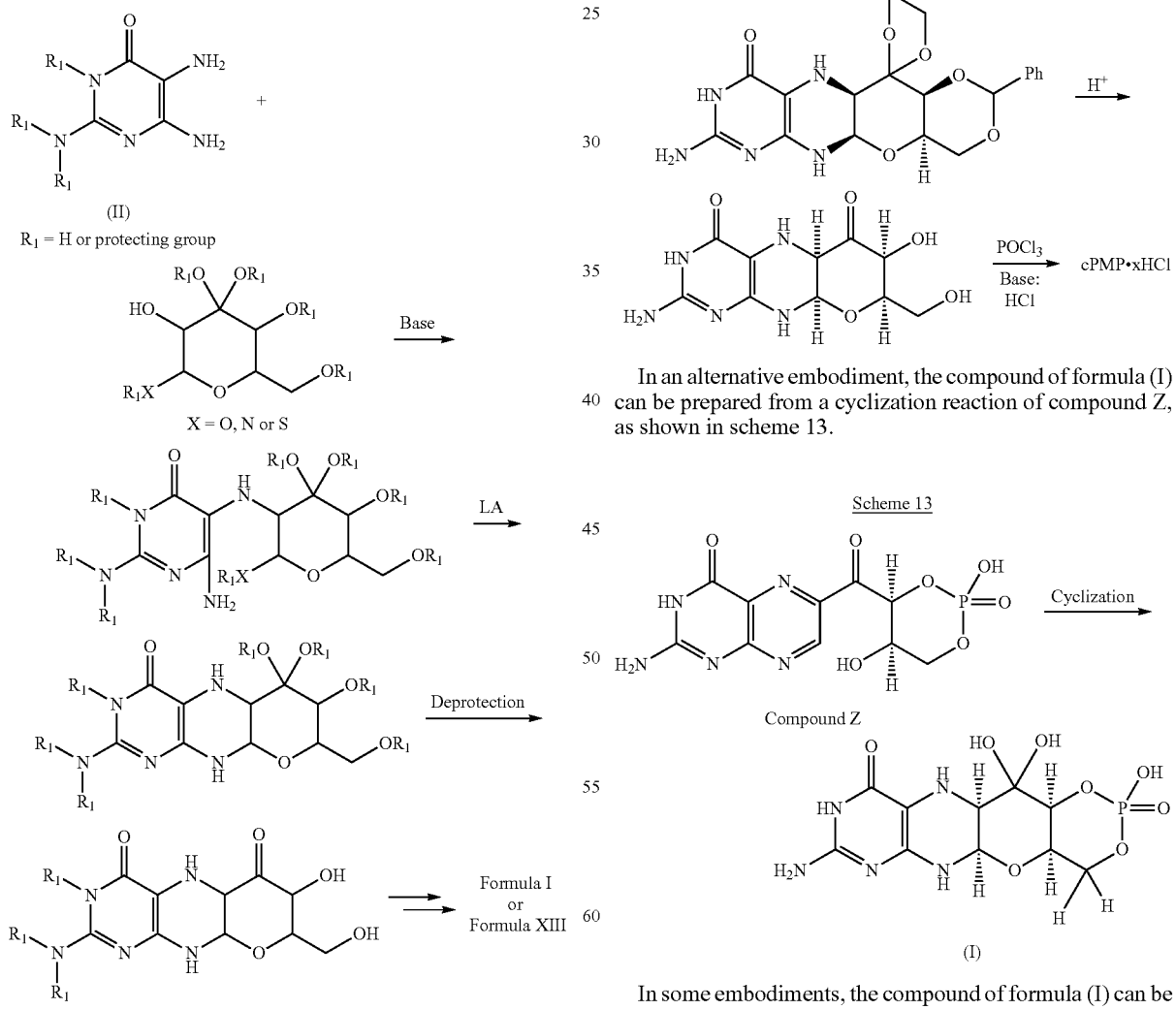

For example, a compound of formula (I) can be prepared as shown in Scheme 12.

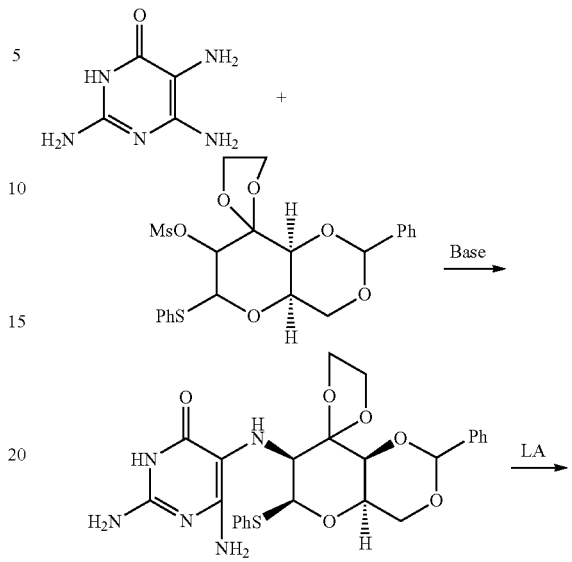

In an alternative embodiment, the compound of formula (I) can be prepared from a cyclization reaction of compound Z, as shown in scheme 13.

In some embodiments, the compound of formula (I) can be prepared as shown in Scheme 14. A diaminopyrimidinone compound of formula (II) can be coupled to a compound of formula (XXII) to afford the piperizine derivative of formula (IV). The piperizine ring nitrogen atoms of the compound of formula (IV) can be protected under standard conditions to give a derivative of formula (V). In some embodiments, the compound of formula (V) can undergo selective deprotection prior to phosphorylation. For example, one or more of the hydroxyl moieties can be deprotected prior to phosphorylation. Phosphorylation of a compound of formula (V) affords a compound of formula (VI). The formula (VI) structure can be oxidized to prepare a compound of formula (VII). Global deprotection of the compound of formula (VII) affords the compound of formula (I).

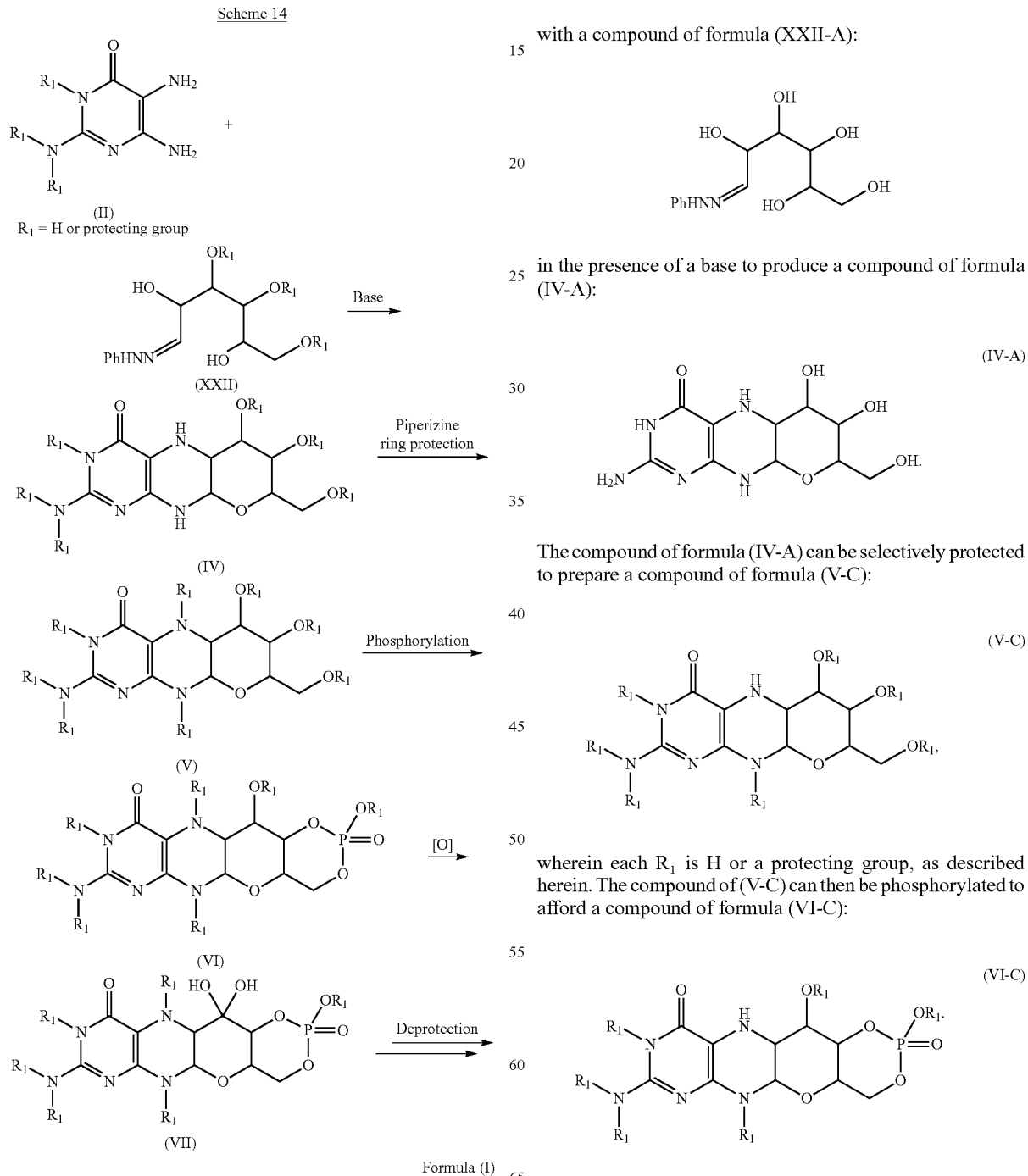

For example, a compound of formula (I), or a pharmaceutically acceptable salt thereof, can be prepared by reacting a compound of formula (II-A):

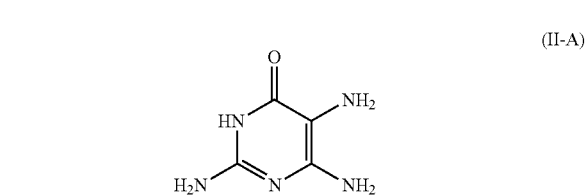

with a compound of formula (XXII-A):

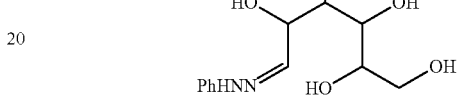

in the presence of a base to produce a compound of formula (IV-A):

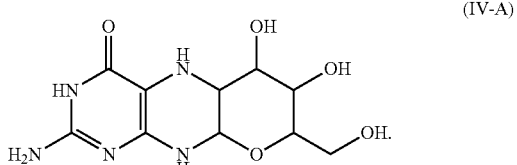

The compound of formula (IV-A) can be selectively protected to prepare a compound of formula (V-C):

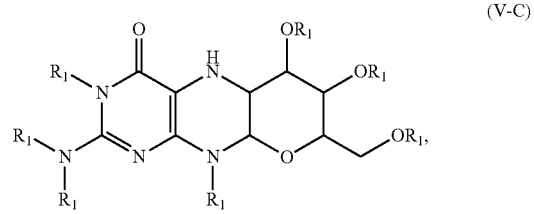

wherein each $R_1$ is H or a protecting group, as described herein. The compound of (V-C) can then be phosphorylated to afford a compound of formula (VI-C):

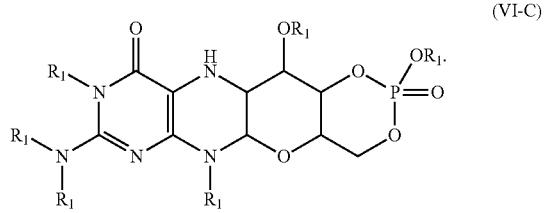

The compound of formula (VI-C) can then be oxidized to prepare a compound of formula (VII-C):

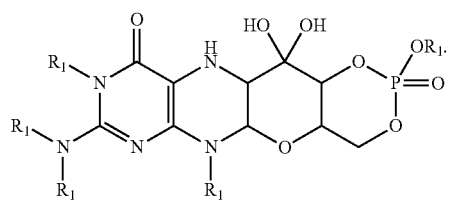

(VII-C)

Finally, the compound of formula (VII-C) is deprotected to prepare the compound of formula (I). In some embodiments, both nitrogens on the piperazine ring of compounds (V-C), (VI-C) and (VII-C) may be bound to $R_1$.

Alternatively, the compound of formula (I) can be prepared as shown in Scheme 15. A compound of formula (XXIII) can undergo epoxidation to provide a compound of formula (XXIV). The compound of formula (XXIV) can be coupled to a compound of formula (II) to prepare a compound of formula (XXV). The compound of formula (XXV) can undergo a ring closure reaction to afford the piperizine derivative of formula (IV). The piperizine ring nitrogen atoms of the compound of formula (IV) can be protected under standard conditions to give a derivative of formula (V). Phosphorylation of a compound of formula (V) affords a compound of formula (VI). The formula (VI) structure can be oxidized to provide a compound of formula (VII). Global deprotection of the compound of formula (VII) affords the compound of formula (I).

Scheme 15

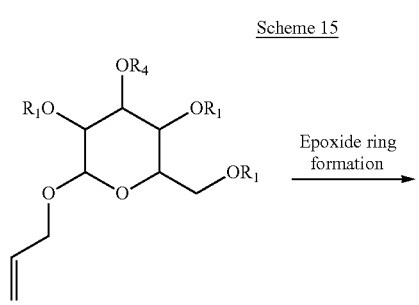

(XXIII)

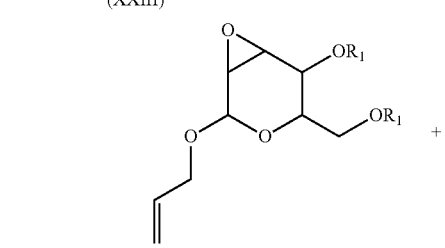

(XXIV)

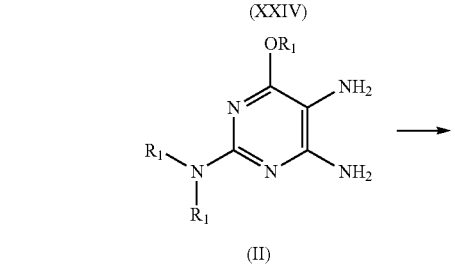

(II)

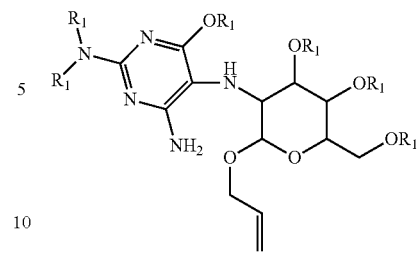

(XXV)

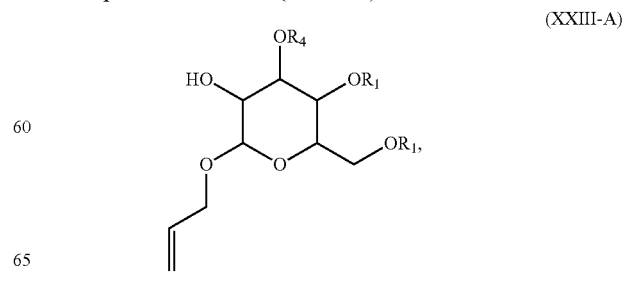

$R_1$ = H or protecting group
$R_4$ = H or leaving group

For example, the compound of formula (I), or a pharmaceutically acceptable salt thereof, can be prepared by reacting a compound of formula (XXIII-A):

(XXIII-A)

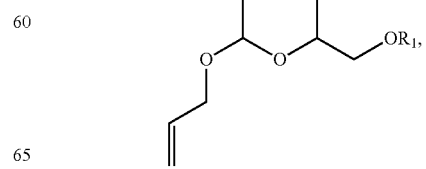

wherein each $R_1$ is independently H or a protecting group and $R_4$ is H or a leaving group, to produce a compound of formula (XXIV):

(XXIV)
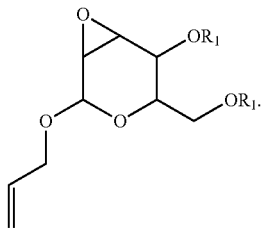

Reacting the compound of formula (XXIV) with a compound of formula (II-A):

(II-A)
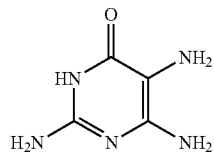

to produce a compound of formula (XXV-A):

(XXV-A)
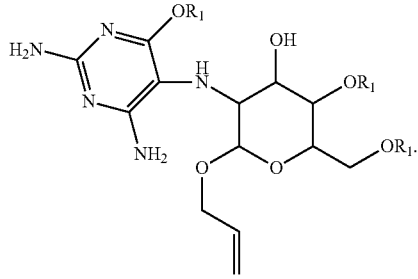

Catalyzing ring formation of the compound of formula (XXV-A) to produce a compound of formula (IV-D):

(IV-D)
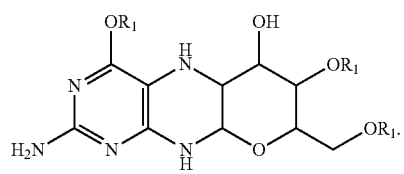

Selectively protecting the compound of formula (IV-D) to prepare a compound of formula (V-D):

(V-D)
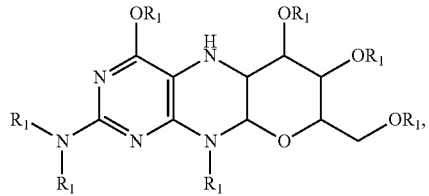

wherein each $R_1$ is H or a protecting group.

Phosphorylating the compound of formula (V-D) to prepare a compound of formula (VI-D):

(VI-D)
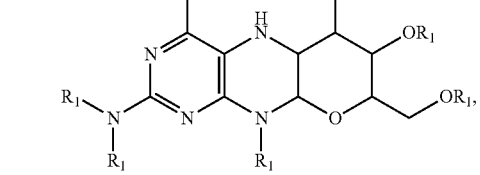

Oxidizing the compound of formula (VI-D) to prepare a compound of formula (VII-D):

(VII-D)
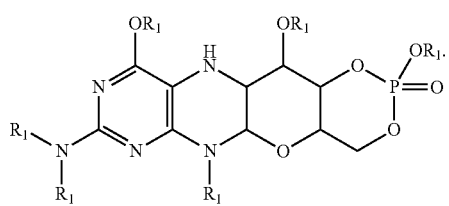

Finally, deprotecting the compound of formula (VII-D) to prepare the compound of formula (I).

Compounds of Formula (XII):

In another embodiment, compounds of formula (XII) are prepared:

(XII)
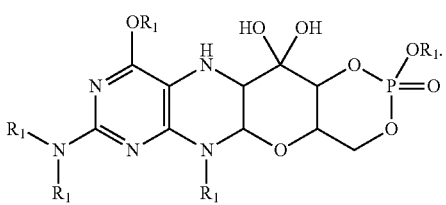

or pharmaceutically acceptable salts or hydrates thereof, wherein each $R_1$ is independently H or a protecting group.

As indicated, certain amino and/or hydroxyl groups of the formula (XII) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, a carbamate protecting group is chosen from 9-fluorenylmethyl carbamate (Fmoc), t-butyl carbamate (Boc), and carboxybenzyl carbamate (cbz) protecting groups.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

Protection of certain amino and hydroxyl groups can improve solubility of the formula (XII) compounds. For example, preparation of acetyl derivatives of a compound of formula (XII) can improve solubility and increase product isolation yield.

A compound of formula (XII) may be prepared by oxidizing a compound of formula (V):

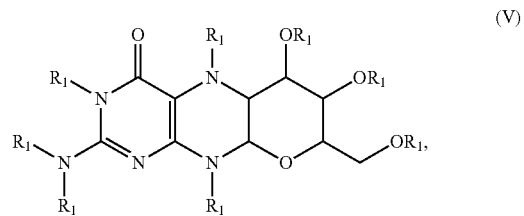

(V)

wherein:
each $R_1$ is independently H or a protecting group, as defined above,
to prepare a compound of formula (XII):

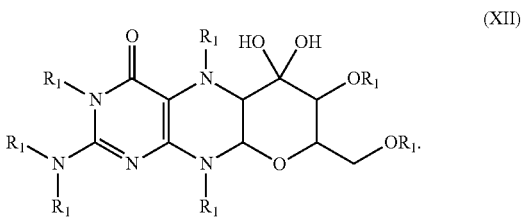

(XII)

In this synthesis, a compound of formula (XII) may be prepared by reacting a compound of formula (V) with any oxidizing agent proper to selectively form the diol of formula (XII). Suitable oxidizing agents and conditions can be readily determined by those of ordinary skill in the art. For example, a compound of formula (XII) may be formed upon treatment of a compound of formula (V) with a ruthenium compound, such as $RuO_4^-/NMO$. Other oxidants, such as Dess-Martin's reagent, DMSO/triflic anhydride, TFAA/DMSO, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridyldisulfide (DPS), and osmium tetroxide may also be used. In one embodiment, the oxidation conditions are performed so that the pyrazine ring of compound (XII) is not oxidized. In some embodiments, the oxidizing agent is chosen from $RuO_4^-/NMO$, Dess-Martin's reagent, DMSO/triflic anhydride, TFAA/DMSO, and PDC.

For example, the oxidation reaction may be carried out by treating a compound of formula (V) with RuO$_4^-$/NMO at ambient temperature to afford a compound of formula (XII). In another embodiment, a compound of formula (XII) is formed by treating a compound of formula (V) with RuO$_4^-$/NMO at a temperature from about 20-60° C. (e.g., at about 20, 25, 30, 35, 40, 45, 50, or 55° C.).

As will be understood, the isomeric form of the formula (XII) structure may regulate the stereospecificity of subsequent intermediates in the successive steps in the synthesis of formula (I) or formula (XIII). Accordingly, a particular isomer may be isolated at this step of the synthesis or, alternatively, isomeric mixtures of a compound of formula (XII) may be carried through and isolated at later stages of the synthesis. Compounds of Formula (XIII):

In another embodiment, a compound of the formula (XIII) is prepared:

Scheme 16.

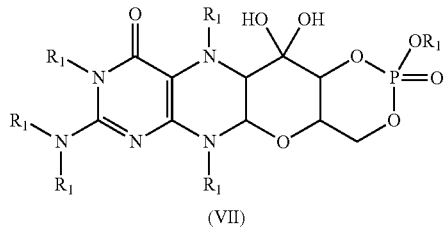

(VII)

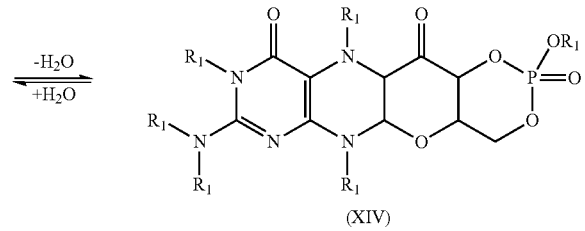

(XIV)

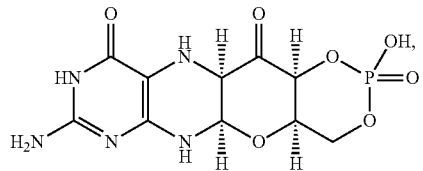

(XIII)

or pharmaceutically acceptable salts or hydrates thereof. A compound of formula (XIII) also includes the tautomeric structure:

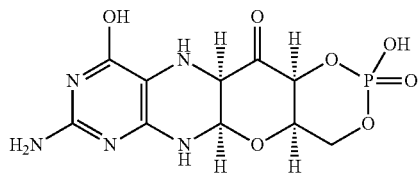 [SMILES: Nc1nc(O)c2c(n1)N[C@@H]1O[C@@H]3COP(=O)(O)O[C@@H]3C(=O)[C@@H]1N2]

or pharmaceutically acceptable salts or hydrates thereof.

The compound of formula (I) can be a reaction product of a compound of formula (XIII) and water. Alternatively, the compound of formula (XIII) can be a dehydration product of a compound of formula (I). Given the equilibrium created between these two products, at certain pHs and conditions, both species may be present in an aqueous solution. One of skill in the art can control synthetic conditions (e.g., working in the absence of water) to isolate the ketone species of formula (XIII) to reduce or eliminate the presence of the compound of formula (I). While the methods described above for producing a compound of formula (I) give rise to a gem-diol following oxidation (e.g., a compound of formula (VII)), the methods can include an additional step involving suitable dehydration conditions (e.g., concentrated acid or base) to produce a ketone (e.g., a compound of formula (XIV)). For example, the conversion can occur as shown in Scheme 16.

Following formation of the ketone, the remaining steps of the methods described below may be used to produce a compound of formula (XIII).

The compound of formula (XIII) may be prepared by deprotecting the compound of formula (XIV):

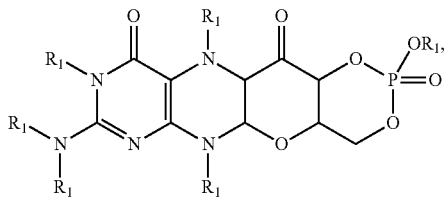

wherein:

each R$_1$ is independently H or a protecting group, as defined above, to prepare the compound of formula (XIII).

In this synthesis, the deprotection may involve, for example, either sequential or one-pot deprotection of certain amino and hydroxyl protecting groups of formula (XIV) to furnish the compound of formula (XIII). Suitable reagents and conditions for the deprotection of the compound of formula (XIV) can be readily determined by those of ordinary skill in the art. For example, compound (XIII) may be formed upon treatment of the compound of formula (XIV) under conditions so that hydroxyl protecting groups, such as acetate, isopropylidine, and benzylidine protecting groups, are removed from formula (XIV). The acetate group can be cleaved, for example, under Zemplén conditions using catalytic NaOMe as a base in methanol. The benzylidene and isopropylidene groups can be cleaved by hydrogenation or using acidic hydrolysis as reported by R. M. Hann et al., *J. Am. Chem. Soc.*, 72, 561 (1950). In yet another example, the deprotection can be performed so that amino protecting groups, such as 9-fluorenylmethyl carbamate (Fmoc), t-butyl carbamate (Boc), and carboxybenzyl carbamate (cbz) protecting groups are cleaved from the compound of formula (XIV). 9-fluorenylmethyl carbamate (Fmoc) can be removed under mild conditions with an amine base (e.g., piperidine) to afford the free amine and dibenzofulvene, as described by E. Atherton et al., "*The Fluorenylmethoxycarbonyl Amino Protecting Group*," in The Peptides, S. Udenfriend and J. Meienhofer, Academic Press, New York, 1987, p. 1. t-butyl carbamate (Boc) can be removed, as reported by G. L. Stahl et al., *J. Org. Chem.*, 43, 2285 (1978), under acidic conditions (e.g., 3

M HCl in EtOAc). Hydrogenation can be used to cleave the carboxybenzyl carbamate (cbz) protecting group as described by J. Meienhofer et al., *Tetrahedron Lett.*, 29, 2983 (1988).

To prevent oxidation of formula (XIII) during the reaction, the deprotection may be performed under anaerobic conditions. The deprotection may also be performed at ambient temperature or at temperatures of from 20-60° C., or 25, 30, 35, 40, 45, 50, or 55° C.

Alternatively, compounds of formula (XIII) can be formed as shown in Scheme 17. A diaminopyrimidinone compound of formula (II) can be coupled with a phosphorylated hexose sugar of formula (VIII), to give a compound of formula (IX). The piperizine ring nitrogen atoms can be protected to give a compound of formula (X) which can be oxidized to give a diol of formula (XV). The diol of formula (XV) can then be deprotected using appropriate conditions and converted to the compound of formula (XIII).

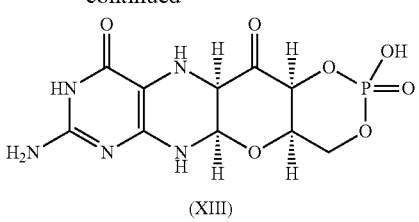

(XIII)

$R_1$ = H or protecting group
$R_2$ = H or protecting group
$R_3$ = protecting group
$R_4$ = H or protecting group In another embodiment, a compound of formula (XIII) may be formed as shown in Scheme 18. For example, a diaminopyrimidinone compound of formula (II) can be reacted with a protected or unprotected hexose sugar of formula (III) to give a compound of formula (IV). The ring nitrogen atoms of the piperizine ring of formula (IV) can then be selectively protected using standard conditions to give a derivative of formula (V). Phosphorylation of the compound of formula (V) can furnish a phosphate intermediate of formula (VI). The phosphate of formula (VI) can be converted to a ketone of formula (XIV) under appropriate oxidation conditions. Finally, the compound of formula (XIV) can be deprotected to give the compound of formula (XIII).

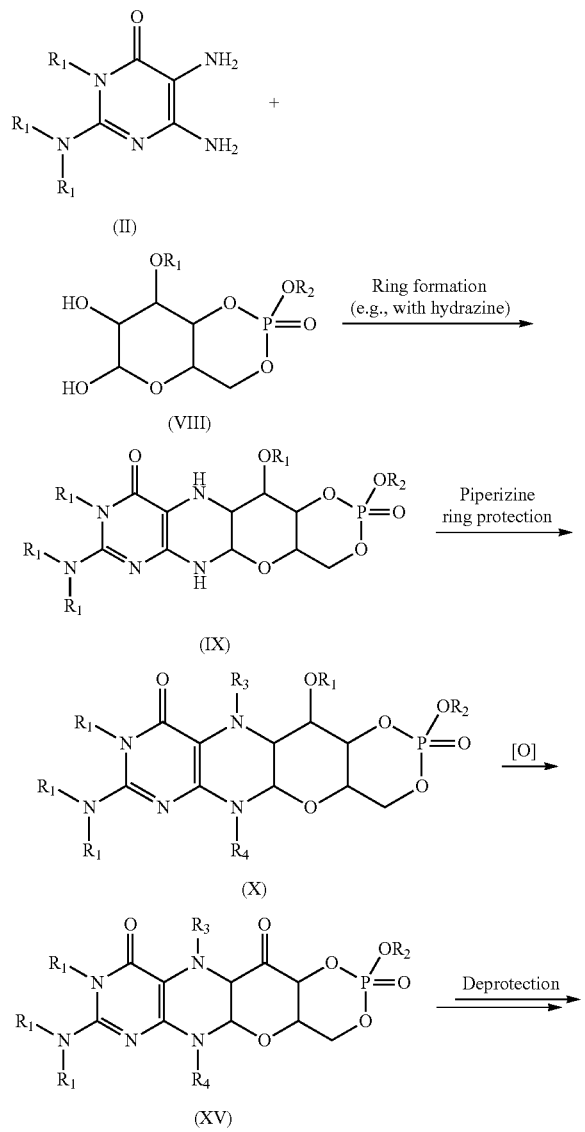

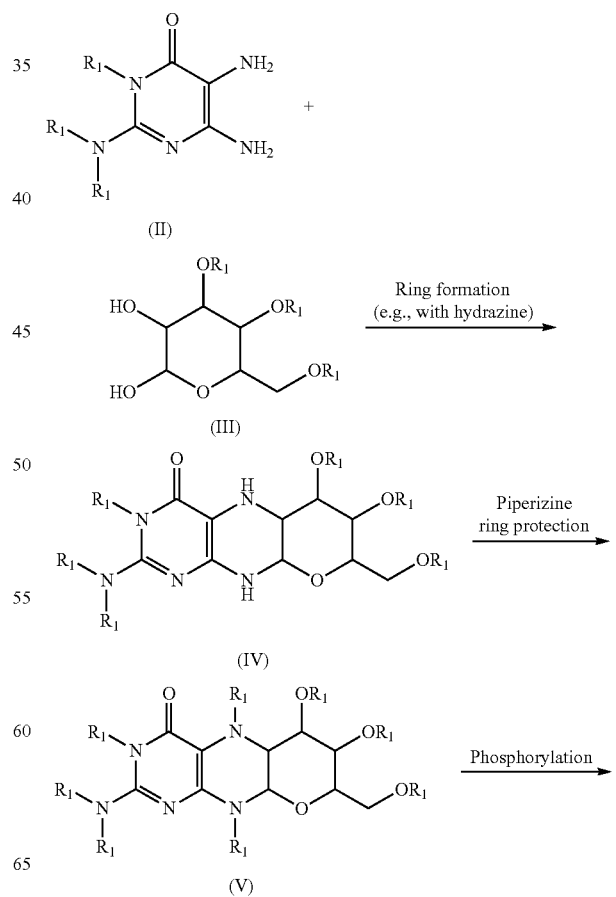

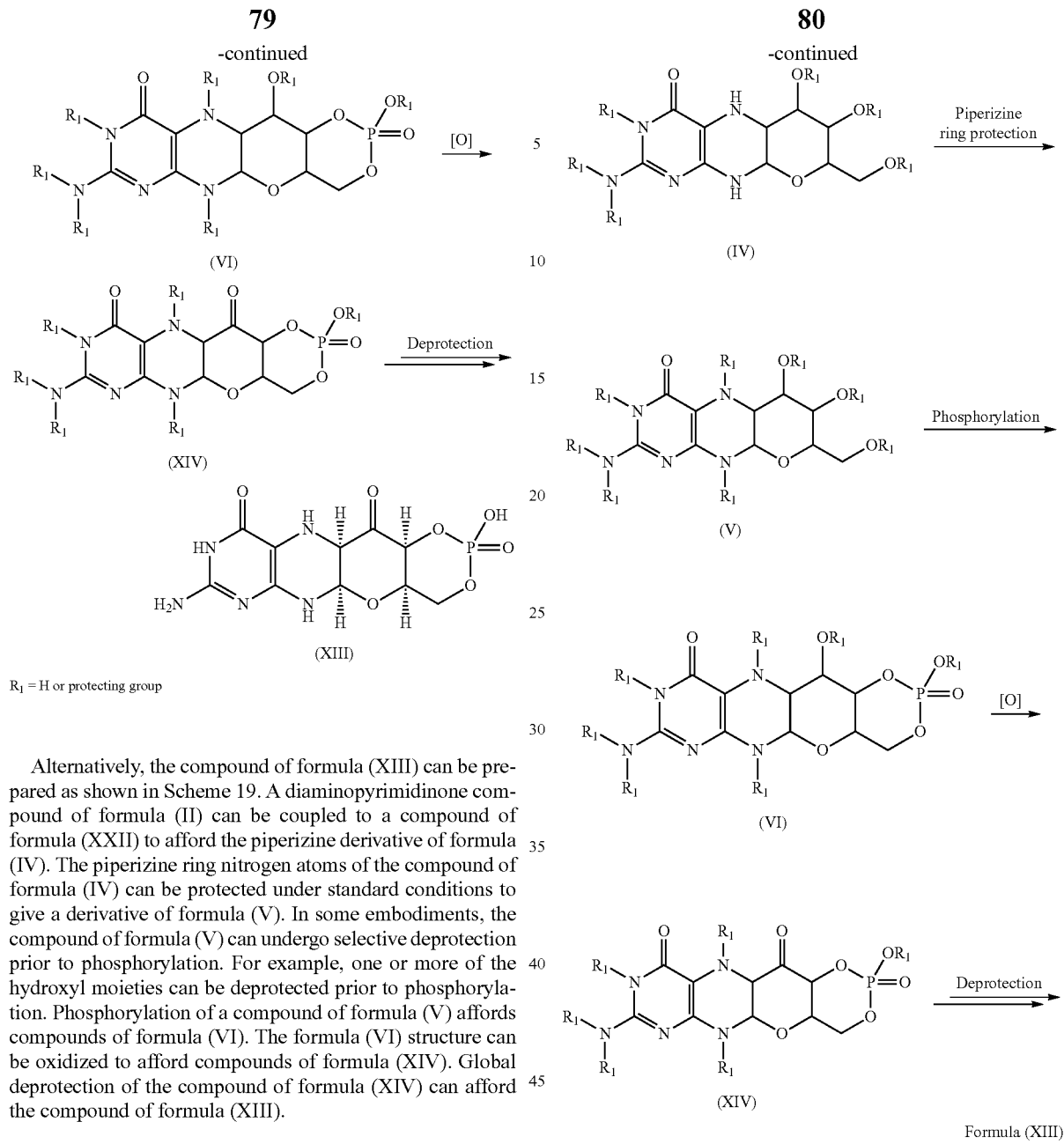

Alternatively, the compound of formula (XIII) can be prepared as shown in Scheme 19. A diaminopyrimidinone compound of formula (II) can be coupled to a compound of formula (XXII) to afford the piperizine derivative of formula (IV). The piperizine ring nitrogen atoms of the compound of formula (IV) can be protected under standard conditions to give a derivative of formula (V). In some embodiments, the compound of formula (V) can undergo selective deprotection prior to phosphorylation. For example, one or more of the hydroxyl moieties can be deprotected prior to phosphorylation. Phosphorylation of a compound of formula (V) affords compounds of formula (VI). The formula (VI) structure can be oxidized to afford compounds of formula (XIV). Global deprotection of the compound of formula (XIV) can afford the compound of formula (XIII).

Scheme 19

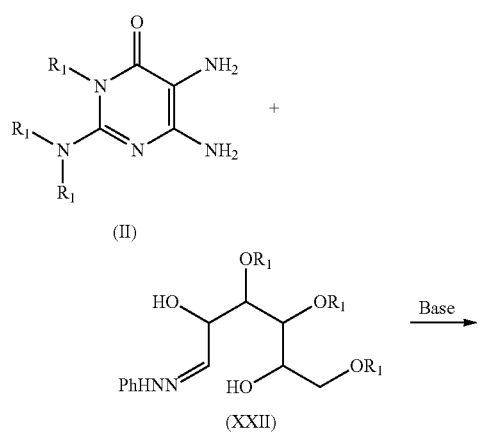

Alternatively, the compound of formula (XIII) can be prepared as shown in Scheme 20. A compound of formula (XXIII) can undergo epoxidation to provide a compound of formula (XXIV). The compound of formula (XXIV) can be coupled to a compound of formula (II) to prepare a compound of formula (XXV). The compound of formula (XXV) can undergo a ring closure reaction to afford the piperizine derivative of formula (IV). The piperizine ring nitrogen atoms of the compound of formula (IV) can be protected under standard conditions to give a derivative of formula (V). Phosphorylation of a compound of formula (V) affords compounds of formula (VI). The formula (VI) structure can be oxidized to afford compounds of formula (XIV). Global deprotection of the compound of formula (XIV) can afford the compound of formula (XIII).

Scheme 20

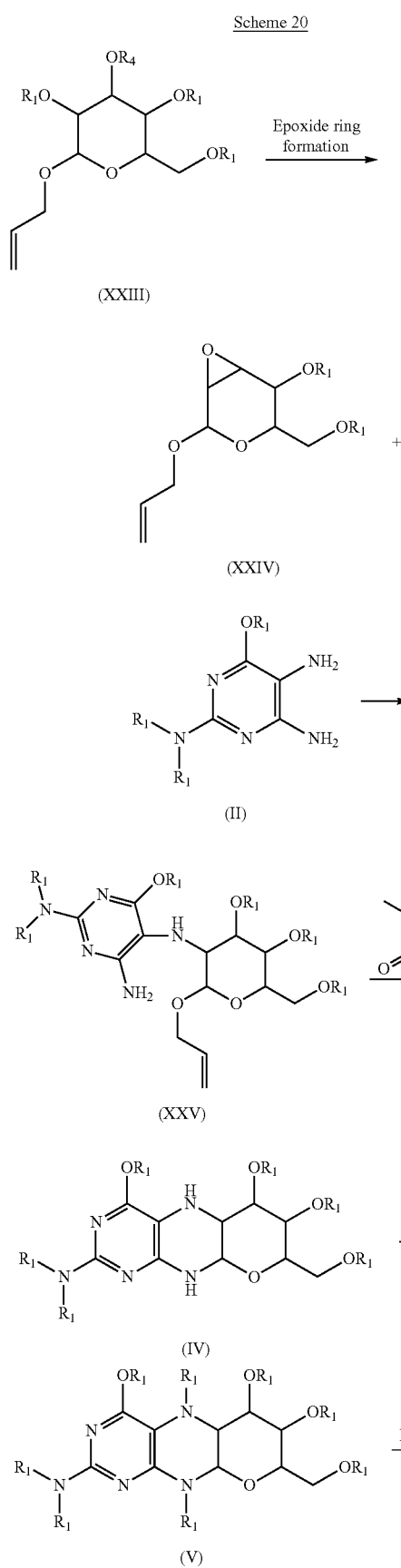

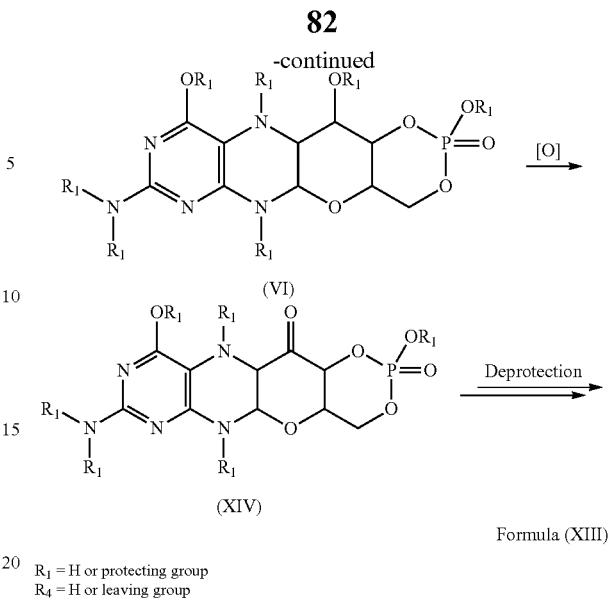

$R_1$ = H or protecting group
$R_4$ = H or leaving group

The compound of formula (XIII) may be isolated in the form a pharmaceutically acceptable salt. For example, the compound of formula (XIII) may be crystallized in the presence of HCl to form the HCl salt form of the compound. In some embodiments, the compound of formula (XIII) may be crystallized as the HBr salt form of the compound. The compound of formula (XIII) may also be isolated, e.g., by precipitation as a sodium salt by treating with NaOH. The compound of formula (XIII) is labile under certain reaction and storage conditions. In some embodiments, the final solution comprising the compound of formula (XIII) may be acidified by methods known in the art. For example, the compound of formula (XIII), if stored in solution, can be stored in an acidic solution.

Compounds of Formula (XIV)

In another embodiment, compounds of formula (XIV) are prepared:

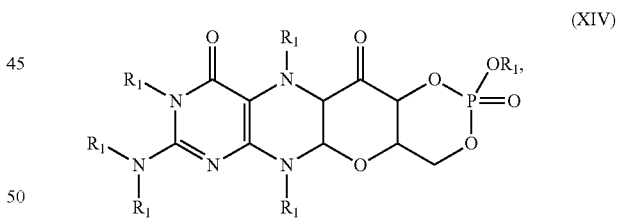

or pharmaceutically acceptable salts or hydrates thereof, wherein each $R_1$ is independently H or a protecting group. For example, the compound for formula (XIV) includes the compound (XIV-A):

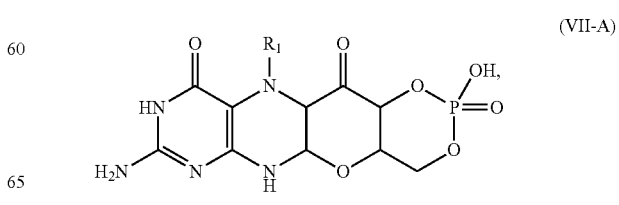

or a pharmaceutically acceptable salt thereof, wherein $R_1$ is H or a protecting group. The compound of formula (XIV) also includes, for example, the compound:

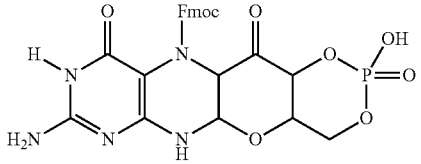

(9H-fluoren-9-yl)methyl 8-amino-2-hydroxy-10,12-dioxo-4-4a,5a,6,9,10,12,12a-octahydro-[1,3,2]dioxaphosphinino[4',5':5,6]pyrano[3,2-g]pteridine-11(11aH)-carboxylate 2-oxide or a pharmaceutically acceptable salt thereof. In some embodiments, the compound of formula (XIV) includes the compound (XIV-B):

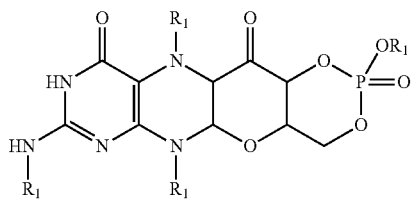

(VII-B)

or a pharmaceutically acceptable salt thereof. In some embodiments, the compound of formula (XIV) includes the compound (XIV-C):

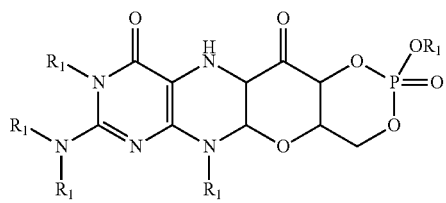

(VII-C)

or a pharmaceutically acceptable salt thereof. In some embodiments, a compound of formula (XIV) can include one or more of the following:

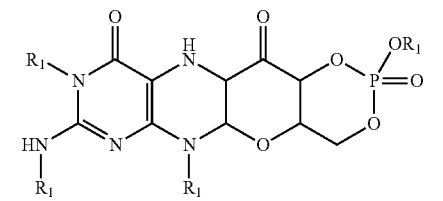

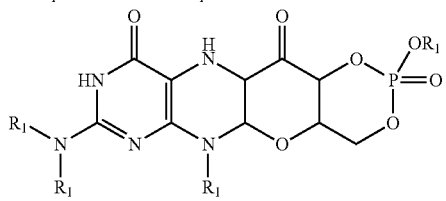

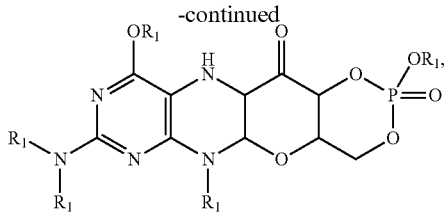

or a pharmaceutically acceptable salt thereof. For example, a compound of formula (XIV) can include one or more of the following:

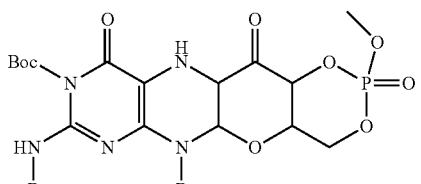

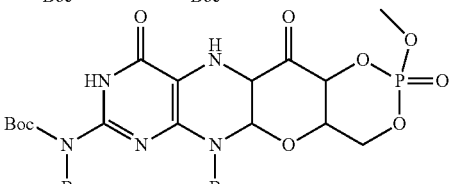

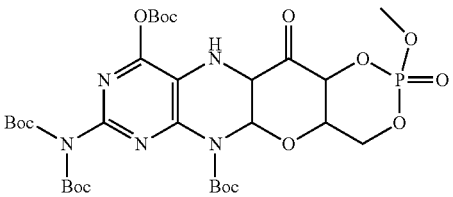

or a pharmaceutically acceptable salt thereof. In some embodiments, one or more of the above compounds can be separated by those skilled in the art by a variety of methods, including high performance liquid chromatography (HPLC) ("*Preparative LC-MS Purification: Improved Compound Specific Method Optimization*" K. F. Blom, et al., *J. Combi. Chem.* 6(6), 874 (2004), which is incorporated herein by reference in its entirety) and normal phase silica chromatography.

As indicated, certain amino and/or hydroxyl groups of the formula (XIV) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, 9-(2,7-dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene- 2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N, N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In particular, 9-fluorenylmethyl carbamate (Fmoc), t-butyl carbamate (Boc), and carboxybenzyl carbamate (cbz) protecting groups may be used.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide The ether protecting group may include methyl, methoxymethyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

Protection of certain amino and hydroxyl groups can improve solubility of the formula (XIV) compounds. For example, preparation of acetyl derivatives of formula (XIV) can improve solubility and increase product isolation yield.

The compound of formula (XIV) may be prepared by oxidizing the compound of formula (VI):

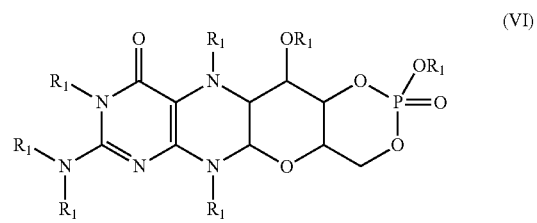

(VI)

to prepare a compound of formula (XIV):

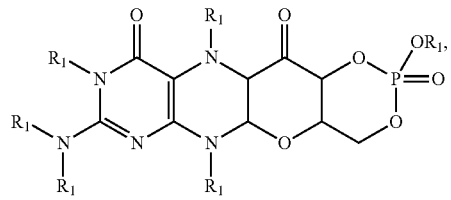

wherein:

each $R_1$ is independently H or a protecting group, as defined above.

In this synthesis, the compound of formula (XIV) may be prepared by reacting the compound of formula (VI) with any oxidizing agent proper to selectively form the ketone of formula (XIV). Suitable oxidizing agents and conditions can be readily determined by those of ordinary skill in the art. For example, compound (XIV) may be formed upon treatment of the compound of formula (VI) with a ruthenium compound, such as $RuO_4^-$/NMO. Other oxidants, such as Dess-Martin's reagent, DMSO/triflic anhydride, TFAA/DMSO, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridyldisulfide (DPS), and osmium tetroxide may also be used. In one embodiment, the oxidation conditions are performed so that the pyrazine ring of compound (XIV) is not oxidized. In particular, the oxidizing agents $RuO_4^-$/NMO, Dess-Martin's reagent, DMSO/triflic anhydride and PDC may be used.

For example, the oxidation reaction may be carried out by treating the compound of formula (VI) with $RuO_4^-$/NMO at ambient temperature to afford the compound of formula (XIV). In another embodiment, the compound of formula (XIV) is formed by treating the compound of formula (VI) with $RuO_4^-$/NMO at a temperature from 20-60° C., or at 20, 25, 30, 35, 40, 45, 50, or 55° C.

A compound of formula (XIV) can also be prepared by dehydrating a compound of formula (VII). Suitable reaction conditions for such a dehydration reaction are readily determined by those of ordinary skill in the art. For example, a compound of formula (VII) can be combined with a concentrated acid or base to prepare a compound of formula (XIV).

As will be understood, the isomeric form of the formula (XIV) structure may regulate the stereospecificity of subsequent intermediates in the successive steps of the synthesis of formula (XIII). Accordingly, a particular isomer may be isolated at this step of the synthesis or, alternatively, isomeric mixtures of formula (XIV) may be carried through and isolated at later stages of the synthesis.

In one embodiment, the compound of formula (XIV) includes the isomer:

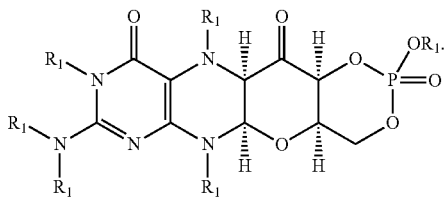

The compound of formula (XIV) also includes the tautomeric structure:

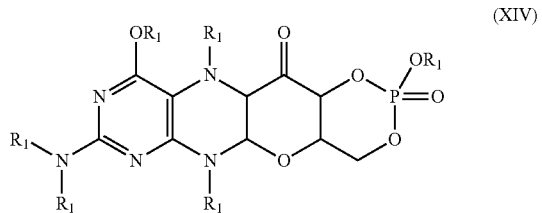

or a pharmaceutically acceptable salt thereof.

Compounds of Formula (XXII)

Another embodiment relates to a compound of formula (XXII):

(XXII)

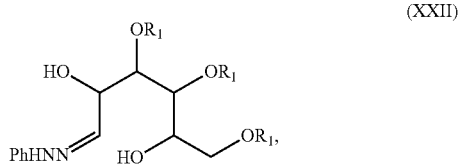

or pharmaceutically acceptable salts or hydrates thereof, wherein each $R_1$ is independently H or a protecting group.

As indicated, the hydroxyl groups in the compound of formula (XXII) may be in protected or unprotected form. For example, in an unprotected form, the compound for formula (XXII) may include the compound (XXII-A):

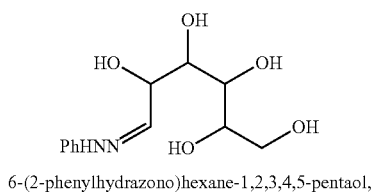

6-(2-phenylhydrazono)hexane-1,2,3,4,5-pentaol, or a pharmaceutically acceptable salt, thereof.

Certain hydroxyl groups of the formula (XXII) structure may be protected with an $R_1$ protecting group. For this purpose, $R_1$ may include any suitable hydroxyl functional group chosen by a person skilled in the chemical arts. For example, non-limiting examples of hydroxyl protecting groups may include ether, ester, carbonate, or sulfonate protecting groups. The $R_1$ protecting groups may be the same or different.

The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose ring component of formula (XXII) can combine to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety.

Protection of certain amino and hydroxyl groups can improve solubility of the formula (XXII) compounds. For example, preparation of acetyl derivatives of formula (XXII) can improve solubility and increase product isolation yield.

A compound of formula (XXII) may be prepared by known methods (see, e.g., Goswami, S.; Adak, A. K. *Tetrahedron Lett.* (2005), 46, 221-224) or purchased commercially.

As will be understood, the isomeric form of the formula (XXII) structure may govern the stereospecificity of subsequent intermediates in the successive steps of the synthesis of formula (I) or formula (XIII). Accordingly, a particular isomer may be isolated at this step of the synthesis or, alternatively, isomeric mixtures of formula (XXII) may be carried through and isolated at later stages of the synthesis.

In some embodiments, the compound of formula (XXII) includes the isomer:

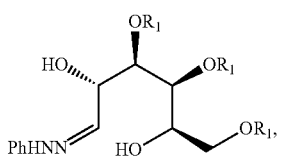

or pharmaceutically acceptable salts or hydrates thereof.

Compounds of Formula (XXIII)

Another embodiment relates to a compound of formula (XXIII):

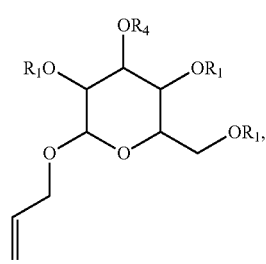

or pharmaceutically acceptable salts or hydrates thereof, wherein each $R_1$ is independently H or a protecting group and $R_4$ is H or a leaving group.

As indicated, the hydroxyl groups in the compound of formula (XXIII) may be in protected or unprotected form. For example, in an unprotected form, the compound for formula (XXIII) may include the compound 2-(allyloxy)-6-(hydroxymethyl)tetrahydro-2H-pyran-3,4,5-triol:

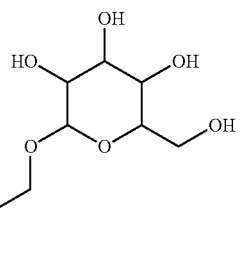

2-(allyloxy)-6-(hydroxymethyl)tetrahydro-2H-, pyran-3,4,5-triol or a pharmaceutically acceptable salt, thereof.

Certain hydroxyl groups of the formula (XXIII) structure may be protected with an $R_1$ protecting group. For this purpose, $R_1$ may include any suitable hydroxyl functional group chosen by a person skilled in the chemical arts. For example, non-limiting examples of hydroxyl protecting groups may include ether, ester, carbonate, or sulfonate protecting groups. The $R_1$ protecting groups may be the same or different.

The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5,5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose ring component of formula (XXIII) can combine to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, a compound of formula (XXIII) can be a compound of formula (XXIII-B):

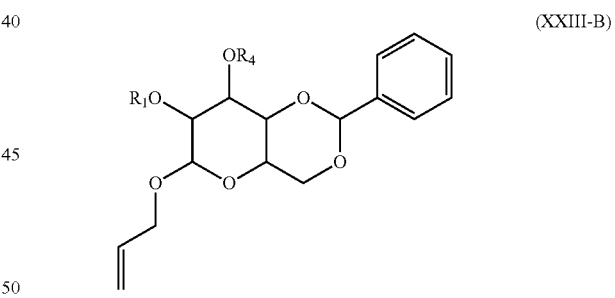

or a pharmaceutically acceptable salt thereof. For example, a compound of (XXIII) can include a compound:

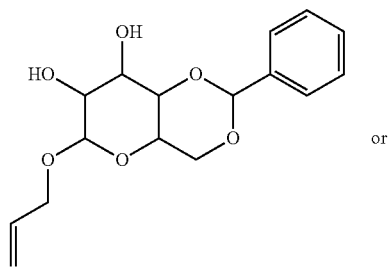

or

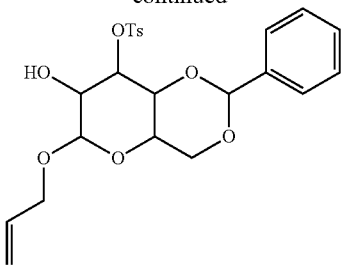

or a pharmaceutically acceptable salt thereof.

Protection of certain amino and hydroxyl groups can improve solubility of the formula (XXIII) compounds. For example, preparation of acetyl derivatives of formula (XXIII) can improve solubility and increase product isolation yield.

As indicated above, $R_4$ can be a leaving group. For this purpose, $R_4$ may include any suitable hydroxyl leaving group chosen by a person skilled in the chemical arts. For example, non-limiting examples of hydroxyl protecting groups may include tosylates, brosylates, nosylates, mesylates, oxoniums, triflates, nonaflates, and tresylates.

A compound of formula (XXIII) may be prepared by known methods or purchased commercially.

As will be understood, the isomeric form of the formula (XXIII) structure may govern the stereospecificity of subsequent intermediates in the successive steps of the synthesis of formula (I) or formula (XIII). Accordingly, a particular isomer may be isolated at this step of the synthesis or, alternatively, isomeric mixtures of formula (XXIII) may be carried through and isolated at later stages of the synthesis.

In one embodiment, the compound of formula (XXIII) includes the isomer:

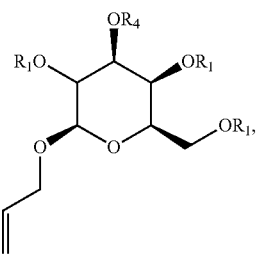

or pharmaceutically acceptable salts or hydrates thereof.

Compounds of Formula (XXIV)

Another embodiment relates to a compound of formula (XXIV):

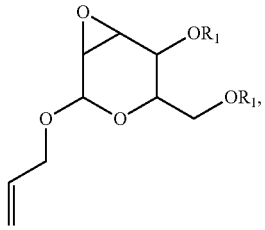

(XXIV)

or pharmaceutically acceptable salts or hydrates thereof, wherein each $R_1$ is independently H or a protecting group.

As indicated, the hydroxyl groups in the compound of formula (XXIV) may be in protected or unprotected form. For example, in an unprotected form, the compound for formula (XXIV) may include the compound 2-(allyloxy)-4-(hydroxymethyl)-3,7-dioxabicyclo[4.1.0]heptan-5-ol:

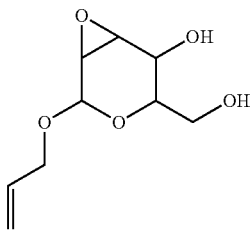

2-(allyloxy)-4-(hydroxymethyl)-3,7-dioxabicyclo[4.1.0]heptan-5-ol, or a pharmaceutically acceptable salt thereof.

Certain hydroxyl groups of the formula (XXIV) structure may be protected with an $R_1$ protecting group. For this purpose, $R_1$ may include any suitable hydroxyl functional group chosen by a person skilled in the chemical arts. For example, non-limiting examples of hydroxyl protecting groups may include ether, ester, carbonate, or sulfonate protecting groups. The $R_1$ protecting groups may be the same or different.

The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose ring component of formula (XXIV) can combine to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, a compound of formula (XXIV) can include a compound:

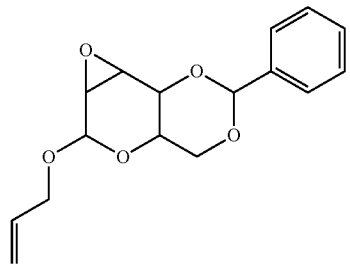 [SMILES: C=CCOC1OC2COC(c3ccccc3)OC2C2OC12]

or a pharmaceutically acceptable salt thereof.

Protection of certain amino and hydroxyl groups can improve solubility of the formula (XXIV) compounds. For example, preparation of acetyl derivatives of formula (XXIV) can improve solubility and increase product isolation yield.

A compound of formula (XXIV) may be prepared by reacting a compound of formula (XXIII):

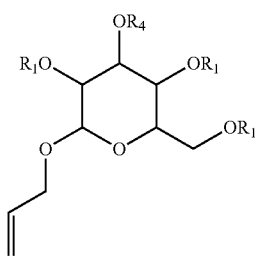

with a base to prepare a compound of formula (XXIV):

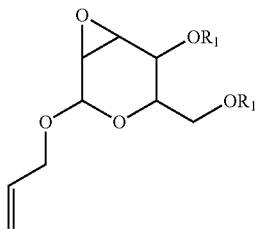

wherein $R_1$ is independently H or a protecting group, and $R_4$ is H or a leaving group, as defined above.

In this synthesis, a compound of formula (XXIV) may be prepared by reacting a compound of formula (XXIII) with any base proper to selectively form the epoxide of formula (XXIV). Suitable bases and conditions can be readily determined by those of ordinary skill in the art. For example, a compound of formula (XXIV) may be formed upon treatment of a compound of formula (XXIII) with a strong base, such as sodium hydroxide. Other bases, such as potassium hydroxide, barium hydroxide, cesium hydroxide, strontium hydroxide, calcium hydroxide, magnesium hydroxide, lithium hydroxide, rubidium hydroxide, butyl lithium, lithium diisopropylamide, lithium diethylamide, sodium amide, sodium hydride, and lithium bis(trimethylsilyl)amide may also be used.

For example, the reaction may be carried out by treating a compound of formula (XXIII) with sodium hydroxide in organic solvent at about 0° C. then warming to room temperature overnight to afford a compound of formula (XXIV).

As will be understood, the isomeric form of the formula (XXIV) structure may govern the stereospecificity of subsequent intermediates in the successive steps of the synthesis of formula (I) or formula (XIII). Accordingly, a particular isomer may be isolated at this step of the synthesis or, alternatively, isomeric mixtures of formula (XXIV) may be carried through and isolated at later stages of the synthesis.

In one embodiment, the compound of formula (XXIV) includes the isomer:

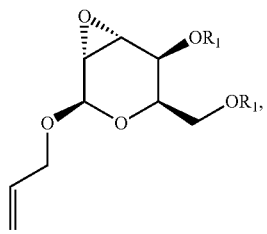

or pharmaceutically acceptable salts or hydrates thereof.

Compounds of Formula (XXV)

Another embodiment relates to a compound of formula (XXV):

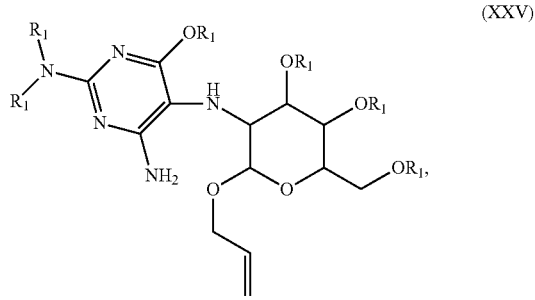

(XXV)

or pharmaceutically acceptable salts or hydrates thereof, wherein each $R_1$ is independently H or a protecting group.

As indicated, the hydroxyl groups in the compound of formula (XXV) may be in protected or unprotected form. For example, in unprotected form, the compound for formula (XXV) may include the compound 6-(allyloxy)-5-[2,4-d] amino-6-hydroxypyrimidin-5-yl)amino)-2-(hydroxymethyl) tetrahydro-2H-pyran-3,4-diol:

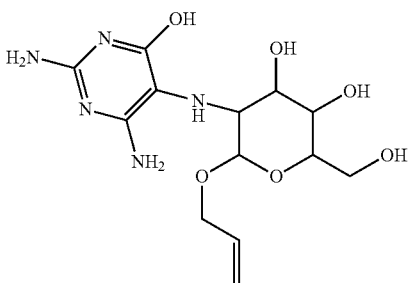

6-(allyloxy)-5-((2,4-diamino-6-hydroxypyrimidin-5-yl)amino)-2-(hydroxymethyl)tetrahydro-2H-pyran-3,4-diol or a pharmaceutically acceptable salt thereof. Alternatively, one or more of the hydroxyl groups may be protected. For example, the compound of formula (XXV) may include a compound of formula (XXV-A):

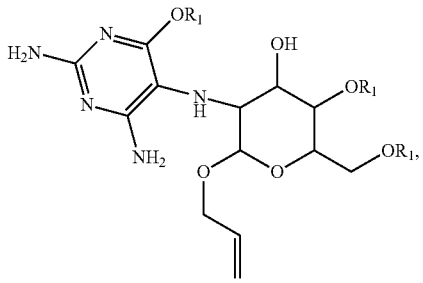

such as the compound 6-(allyloxy)-7-((2,4-diamino-6-(benzyloxy)pyrimidin-5-yl)amino)-2-phenylhexahydropyrano[3,2-d][1,3]dioxin-8-ol:

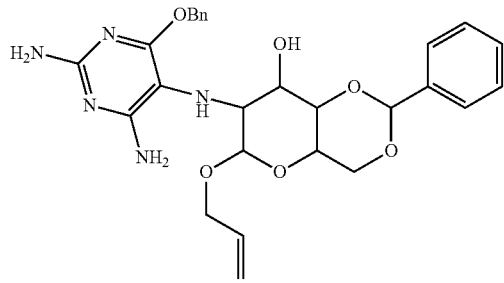

6-(allyloxy)-7-((2,4-diamino-6-(benzyloxy)pyrimidin-5-yl)amino)-2-, phenylhexahydropyrano[3,2-d][1,3]dioxin-8-ol or a pharmaceutically acceptable salt thereof.

As indicated, certain amino and/or hydroxyl groups of the formula (XXV) structure may be protected with an $R_1$ protecting group. For this purpose, $R_1$ may include any suitable amino or hydroxyl functional group chosen by a person skilled in the chemical arts. For example, amino protecting groups within the scope of the present disclosure include, but are not limited to, carbamate, amide, N-alkyl, or N-aryl-derived protecting groups. Non-limiting examples of hydroxyl protecting groups may include ether, ester, carbonate, or sulfonate protecting groups. The $R_1$ protecting groups may be the same or different.

In particular, the carbamate protecting group may include, for example, 9-fluorenylmethyl carbamate (Fmoc), t-butyl carbamate (Boc), carboxybenzyl carbamate (cbz), methyl carbamate, ethyl carbamate, 9-(2-sulfo)fluorenylmethyl carbamate, dibromo)fluorenylmethyl carbamate, 17-tetrabenzo[a,c,g,i]fluorenylmethyl carbamate (Tbfmoc), 2-chloro-3-indenylmethyl carbamate (Climoc), 2,7-di-t-butyl[9-(10,10-dioxo-10,10,10,10-tetrahydrothioxanthyl)]methyl carbamate (DBD-Tmoc), 1,1-dioxobenzo[b]thiophene-2-ylmethyl carbamate (Bsmoc), 2,2,2-trichloroethyl carbamate (Troc), 2-trimethylsilylethyl carbamate (Teoc), 2-phenylethyl carbamate (hZ), 1,1-dimethyl-2-haloethyl carbamate, 1,1-dimethyl-2,2-dibromoethyl carbamate (DB-t-boc), 1,1-dimethyl-2,2,2-trichloroethyl carbamate (TCBoc), 1-methyl-1-(4-biphenylyl)ethyl carbamate (Bpoc), 1-(3,5-di-t-butylphenyl)-1-methylethyl carbamate (t-Bumeoc), N-2-pivaloylamino)-1,1-dimethylethyl carbamate, 2-[(2-nitrophenyl)dithio]-1-phenylethyl carbamate (NpSSPeoc), 2-(N,N-dicyclohexylcarboxamido)ethyl carbamate, 1-adamantyl carbamate (1-Adoc), vinyl carbamate (Voc), 1-isopropylallyl carbamate (Ipaoc), 4-nitrocinnamyl carbamate (Noc), 3-(3'pyridyl)prop-2-enyl carbamate (Paloc), 8-quinolyl carbamate, alkyldithio carbamate, p-methoxybenzyl carbamate (Moz), p-nitrobenzyl carbamate (Pnz), p-bromobenzyl carbamate, p-chlorobenzyl carbamate, 2,4-dichlorobenzyl carbamate, 4-methylsulfinylbenzyl carbamate (Msz), diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 1,1-dimethyl-2-cyanoethyl carbamate, 2-(4-nitrophenyl)ethyl carbamate, 4-phenylacetoxybenzyl carbamate (PhAcOZ), and m-chloro-p-acyloxybenzyl carbamate. In some embodiments, a carbamate protecting group is chosen from 9-fluorenylmethyl carbamate (Fmoc), t-butyl carbamate (Boc), and carboxybenzyl carbamate (cbz) protecting groups.

The amide protecting group may include, for example, acetamide, phenylacetamide, 3-phenylpropanamide, pent-4-enamide, picolinamide, 3-pyridylcarboxamide, benzamide, p-phenylbenzamide, 2-methyl-2-(o-phenylazophenoxy)propanamide), 4-chlorobutanamide, acetoacetamide, 3-(p-hydroxyphenyl)propanamide), and (N'-dithiobenzyloxycarbonylamino)acetamide.

The ether protecting group may include methyl, methoxy methyl (MOM), benzyloxymethyl (BOM), methoxyethoxymethyl (MEM), 2-(trimethylsilyl)ethoxymethyl (SEM), methylthiomethyl (MTM), phenylthiomethyl (PTM), azidomethyl, cyanomethyl, 2,2-dichloro-1,1-difluoroethyl, 2-chloroethyl, 2-bromoethyl, tetrahydropyranyl (THP), 1-ethoxyethyl (EE), phenacyl, 4-bromophenacyl, cyclopropylmethyl, allyl, propargyl, isopropyl, cyclohexyl, t-butyl, benzyl, 2,6-dimethylbenzyl, 4-methoxybenzyl (MPM-OAr), o-nitrobenzyl, 2,6-dichlorobenzyl, 3,4-dichlorobenzyl, 4-(dimethylamino)carbonylbenzyl, 4-methylsulfinylbenzyl (Msib), 9-anthrylmethyl, 4-picolyl, heptafluoro-p-tolyl, tetrafluoro-4-pyridyl, trimethylsilyl (TMS), t-butyldimethylsilyl (TBDMS), t-butyldiphenylsilyl (TBDPS), and triisopropylsilyl (TIPS) protecting groups.

The ester protecting group may include acetoxy (OAc), aryl formate, aryl acetate, aryl levulinate, aryl pivaloate, aryl benzoate, and aryl 9-fluoroenecarboxylate. In one embodiment, the ester protecting group is an acetoxy group.

The carbonate protecting group may include aryl methyl carbonate, 1-adamantyl carbonate (Adoc-OAr), t-butyl carbonate (BOC—OAr), 4-methylsulfinylbenzyl carbonate (Msz-OAr), 2,4-dimethylpent-3-yl carbonate (Doc-OAr), aryl 2,2,2-trichloroethyl carbonate, aryl vinyl carbonate, aryl benzyl carbonate, and aryl carbonate.

The sulfonate protecting groups may include aryl methanesulfonate, aryl toluenesulfonate, and aryl 2-formylbenzenesulfonate.

In some embodiments, the $R_1$ protecting group is t-butyl carbamate (Boc).

In some embodiments, two adjacent $R_1$ groups come together to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, the $R_1$ groups at the 4- and 5-positions of the hexose ring component of formula (XXV) can combine to form an isopropylidine acetal, benzylidine acetal, 1,5-dioxaspiro[5.5]undecane (cyclohexylidene acetal), 6,10-dioxaspiro[4.5]decane (cyclopentylidene acetal), or 2-isobutyl-2-methyl-1,3-dioxane moiety. For example, a compound of formula (XXV) can include a compound:

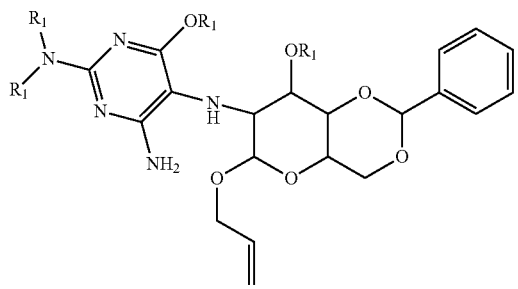

or a pharmaceutically acceptable salt thereof.

Protection of certain amino and hydroxyl groups can improve solubility of the formula (XXV) compounds. For example, preparation of acetyl derivatives of formula (XXV) can improve solubility and increase product isolation yield.

A compound of formula (XXV) may be prepared by reacting a compound of formula (XXIV):

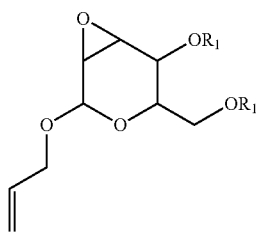

with a compound of formula (II):

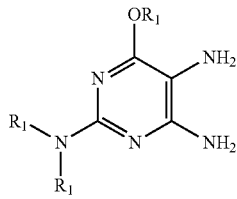

to afford a compound of formula (XXV):

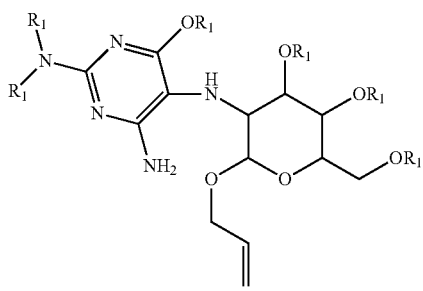

wherein $R_1$ is independently H or a protecting group, as defined above.

In this synthesis, a compound of formula (XXV) may be prepared by coupling a compound of formula (XXIV) with a compound of formula (II) to form the compound of formula (XXV). Suitable reaction conditions can be readily determined by those of ordinary skill in the art. For example, a compound of formula (XXV) may be formed upon treatment of a compound of formula (XXIV) and (II) in the presence of an oxidant, such as lithium perchlorate. Other oxidants, such as $RuO_4^-$/NMO, Dess-Martin's reagent, DMSO/triflic anhydride, TFAA/DMSO, PDC, hydrogen peroxide, inorganic peroxides, nitric acid, nitrates, chlorite, chlorate, perchlorate, hypochlorite, peroxide, iodine, ozone, nitrous oxide, silver oxide, permanganate salts, hexavalent chromium compounds, chromic acid, dichromic acids, chromium trioxide, pyridinium chlorochromate, persulfuric acid, sulfoxides, sulfuric acid, Tollens' reagent, 2,2'-dipyridyldisulfide (DPS), and osmium tetroxide may also be used.

For example, the oxidation reaction may be carried out by treating a mixture of a compound of formula (XXIV) and (II) with lithium perchlorate in organic solvent while heating (e.g., at about 90° C.) to afford a compound of formula (XXV).

As will be understood, the isomeric form of the formula (XXV) structure may govern the stereospecificity of subsequent intermediates in the successive steps of the synthesis of formula (I) or formula (XIII). Accordingly, a particular isomer may be isolated at this step of the synthesis or, alternatively, isomeric mixtures of formula (XXV) may be carried through and isolated at later stages of the synthesis.

In one embodiment, the compound of formula (XXV) includes the isomer:

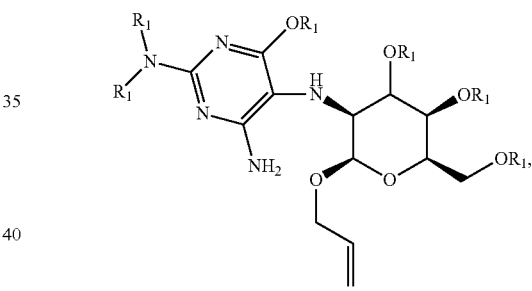

or pharmaceutically acceptable salts or hydrates thereof.

The compound of formula (XXV) can then be used to produce a compound of formula (IV). A compound of formula (IV) may be prepared by reacting a compound of formula (XXV):

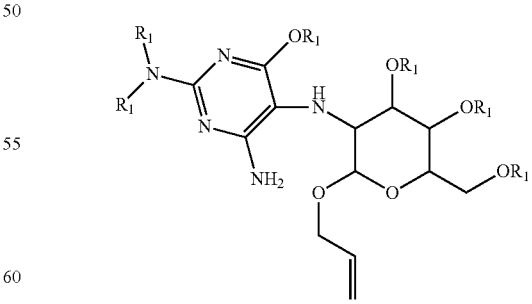

with 1,3-dimethylbarbituric acid to afford a compound of formula (IV), wherein each $R_1$ is independently H or a protecting group, as defined above.

In this synthesis, a compound of formula (IV) may be prepared by reacting a compound of formula (XXV) with 1,3-dimethylbarbituric acid in the presence of a catalyst to form the compound of formula (IV). Suitable catalysts and reaction conditions can be readily determined by those of ordinary skill in the art. For example, a compound of formula (XXV) may be formed upon treatment of a compound of formula (XXIV) and (II) in the presence of a catalyst, such as tetrakis(triphenylphosphine)palladium(0). Other catalysts may also be used.

Pharmaceutical Formulations and Dosage Forms

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal, intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also provides pharmaceutical compositions which contain, as the active ingredient, a compound provided herein or a pharmaceutically acceptable salt thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds provided herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions provided herein can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound provided herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient provided herein.

The tablets or pills provided herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In some embodiments, the compounds provided herein are formulated for intravenous administration. Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound provided herein. The topical formulations can be suitably packaged in tubes of, for example, 100 g which are optionally associated with instructions for the treatment of the select indication.

In one embodiment, the compounds provided herein are prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions provided herein contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions provided herein contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions provided herein contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses provided herein.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The therapeutic dosage of a compound provided herein can vary according to, for example, the particular use for which the treatment is made, the manner of administration of the compound, the health and condition of the patient, and the judgment of the prescribing physician. The proportion or concentration of a compound provided herein in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 mg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

EXAMPLES

Example 1

Preparation of Precursor Z (cPMP)

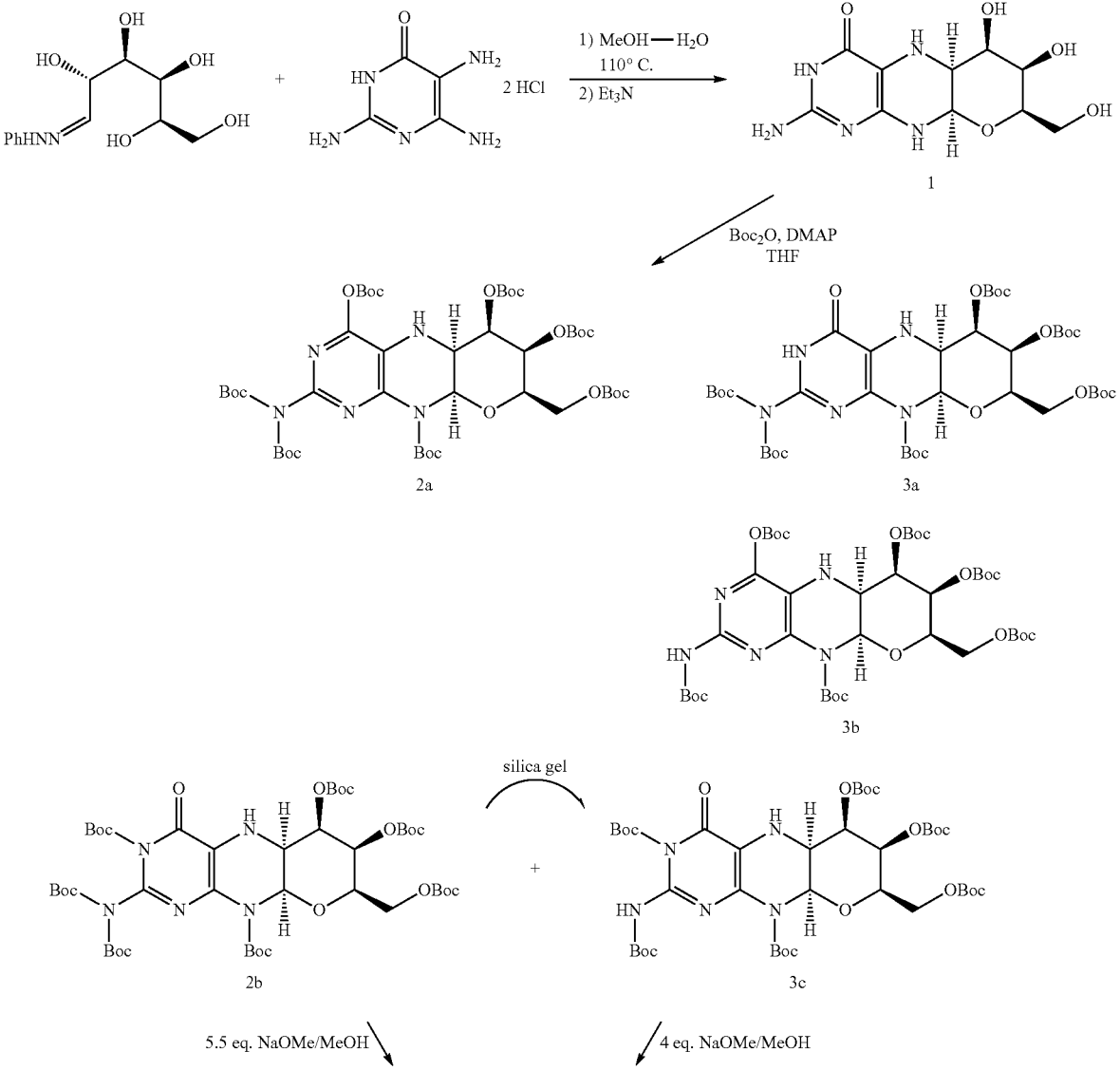

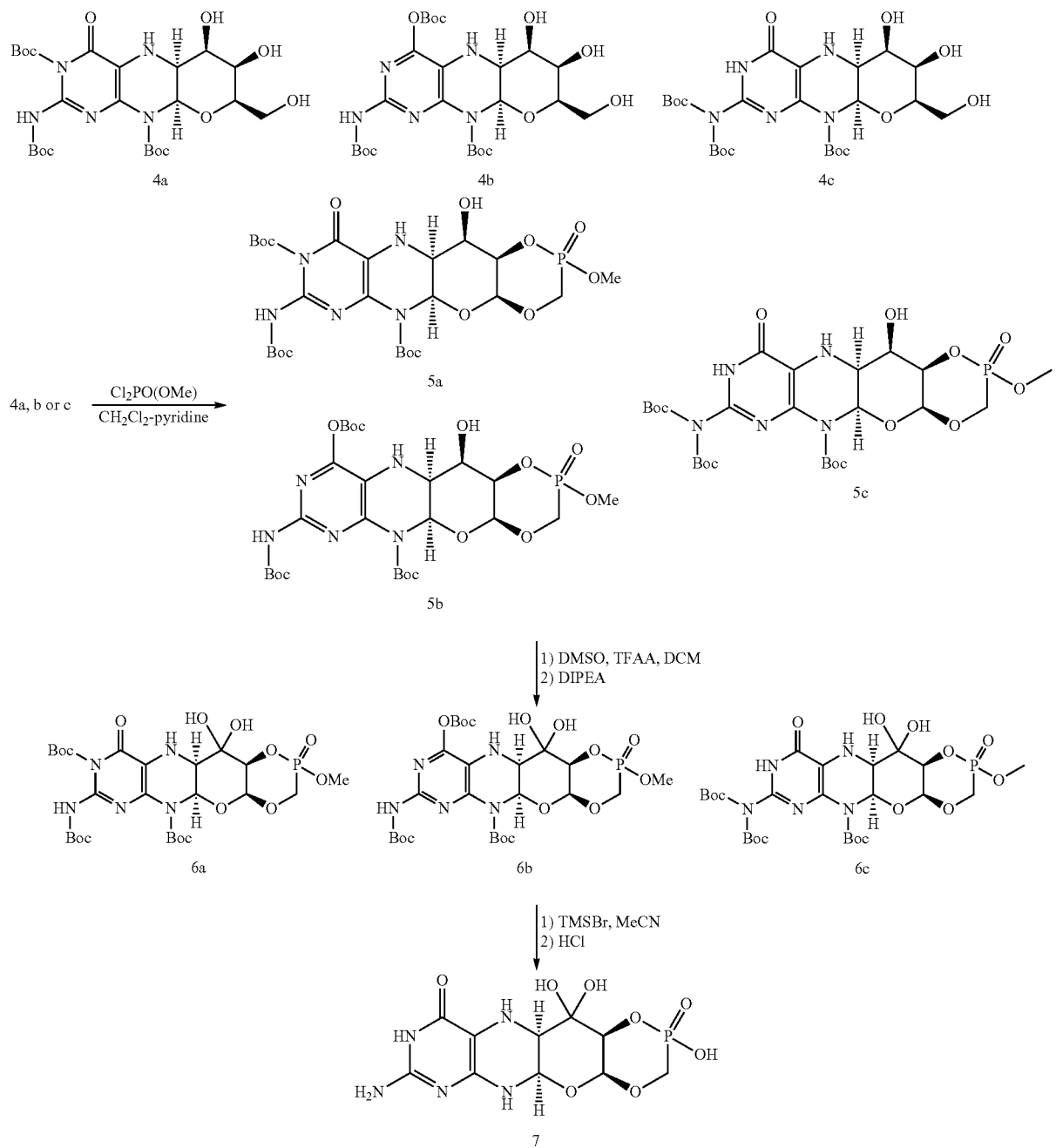

Experimental

Air sensitive reactions were performed under argon. Organic solutions were dried over anhydrous $MgSO_4$ and the solvents were evaporated under reduced pressure. Anhydrous and chromatography solvents were obtained commercially (anhydrous grade solvent from Sigma-Aldrich Fine Chemicals) and used without any further purification. Thin layer chromatography (t.l.c.) was performed on glass or aluminum sheets coated with 60 $F_{254}$ silica gel. Organic compounds were visualized under UV light or with use of a dip of ammonium molybdate (5 wt %) and cerium(IV) sulfate $4H_2O$ (0.2 wt %) in aq. $H_2SO_4$ (2M), one of $I_2$ (0.2%) and KI (7%) in $H_2SO_4$ (1M), or 0.1% ninhydrin in EtOH. Chromatography (flash column) was performed on silica gel (40-63 μm) or on an automated system with continuous gradient facility. Optical rotations were recorded at a path length of 1 dm and are in units of $10^{-1}$ deg $cm^2$ $g^{-1}$; concentrations are in g/100 mL. $^1H$ NMR spectra were measured in $CDCl_3$, $CD_3OD$ (internal $Me_4Si$, δ 0 ppm) or $D_2O$(HOD, δ 4.79 ppm), and $^{13}C$ NMR spectra in $CDCl_3$ (center line, δ 77.0 ppm), $CD_3OD$ (center line, δ 49.0 ppm) or DMSO $d_6$ (center line δ 39.7 ppm), $D_2O$ (no internal reference or internal $CH_3CN$, δ 1.47 ppm where stated). Assignments of $^1H$ and $^{13}C$ resonances were based on 2D ($^1H$—$^1H$ DQF-COSY, $^1H$—$^{13}C$ HSQC, HMBC) and DEPT experiments. $^{31}P$ NMR were run at 202.3 MHz and are reported without reference. High resolution electrospray mass spectra (ESI-HRMS) were recorded on a Q-TOF Tandem Mass Spectrometer. Microanalyses were performed by the Campbell Microanalytical Department, University of Otago, Dunedin, New Zealand.

A. Preparation of (5aS,6R,7R,8R,9aR)-2-amino-6,7-dihydroxy-8-(hydroxymethyl)-3H,4H,5H,5aH,6H,7H,8H,9aH,10H-pyrano[3,2-g]pteridin-4-one mono hydrate (1)

2,5,6-Triamino-3,4-dihydropyrimidin-4-one dihydrochloride (Pfleiderer, W.; *Chem. Ber.* 1957, 90, 2272; *Org. Synth.* 1952, 32, 45; *Org. Synth.* 1963, *Coll. Vol.* 4, 245, 10.0 g, 46.7 mmol), D-galactose phenylhydrazone (Goswami, S.; Adak, A. K. *Tetrahedron Lett.* 2005, 46, 221-224, 15.78 g, 58.4 mmol) and 2-mercaptoethanol (1 mL) were stirred and heated to reflux (bath temp 110° C.) in a 1:1 mixture of MeOH—$H_2O$ (400 mL) for 2 h. After cooling to ambient temperature, diethyl ether (500 mL) was added, the flask was shaken and the diethyl ether layer decanted off and discarded. The process was repeated with two further portions of diethyl ether (500 mL) and then the remaining volatiles were evaporated. Methanol (40 mL), $H_2O$ (40 mL) and triethylamine (39.4 mL, 280 mmol) were successively added and the mixture seeded with a few milligrams of 1. After 5 min a yellow solid was filtered off, washed with a little MeOH and dried to give 1 as a monohydrate (5.05 g, 36%) of suitable purity for further use. An analytical portion was recrystallized from DMSO-EtOH or boiling $H_2O$. MPt 226 dec. $[\alpha]_D^{20}$ +135.6 (c1.13, DMSO). $^1$H NMR (DMSO $d_6$): δ 10.19 (bs, exchanged $D_2O$, 1H), 7.29 (d, J=5.0 Hz, slowly exchanged $D_2O$, 1H), 5.90 (s, exchanged $D_2O$, 2H), 5.33 (d, J=5.4 Hz, exchanged $D_2O$, 1H), 4.66 (ddd, J~5.0, ~1.3, ~1.3 Hz, 1H), 4.59 (t, J=5.6 Hz, exchanged $D_2O$, 1H), 4.39 (d, J=10.3 Hz, exchanged $D_2O$, 1H), 3.80 (bt, J~1.8 Hz, exchanged $D_2O$, 1H), 3.70 (m, 1H), 3.58 (dd, J=10.3, 3.0 Hz, 1H), 3.53 (dt, J=10.7, 6.4 Hz, 1H), 3.43 (ddd, J=11.2, 5.9, 5.9 Hz, 1H), 3.35 (t, J=6.4 Hz, 1H), 3.04 (br m, 1H). $^{13}$C NMR (DMSO $d_6$ center line 6 39.7): δ 156.3 (C), 150.4 (C), 148.4 (C), 99.0 (C), 79.4 (CH), 76.5 (CH), 68.9 (CH), 68.6 (CH), 60.6 ($CH_2$), 53.9 (CH). Anal. calcd. for $C_{10}H_{15}N_5O_5H_2O$ 39.60; C, 5.65; H, 23.09; N. found 39.64; C, 5.71; H, 22.83; N.

B. Preparation of Compounds 2 (a or b) and 3 (a, b or c)

Di-tert-butyl dicarbonate (10.33 g, 47.3 mmol) and DMAP (0.321 g, 2.63 mmol) were added to a stirred suspension of 1 (1.5 g, 5.26 mmol) in anhydrous THF (90 mL) at 50° C. under Ar. After 20 h a clear solution resulted. The solvent was evaporated and the residue chromatographed on silica gel (gradient of 0 to 40% EtOAc in hexanes) to give two product fractions. The first product to elute was a yellow foam (1.46 g). The product was observed to be a mixture of two compounds by $^1$H NMR containing mainly a product with seven Boc groups (2a or 2b). A sample was crystallized from EtOAc-hexanes to give 2a or 2b as a fine crystalline solid. MPt 189-191° C. $[\alpha]_D^{20}$ −43.6 (c 0.99, MeOH). $^1$H NMR (500 MHz, $CDCl_3$): δ 5.71 (t, J=1.7 Hz, 1H), 5.15 (dt, J=3.5, ~1.0, 1H), 4.97 (t, J=3.8 Hz, 1H), 4.35 (br t, J=~1.7, 1H), 4.09-3.97 (m, 3H), 3.91 (m, 1H), 1.55, 1.52, 1.51, 1.50, 1.45 (5s, 45H), 1.40 (s, 18H). $^{13}$C NMR (125.7 MHz, $CDCl_3$): δ 152.84 (C), 152.78 (C), 151.5 (C), 150.9 (C), 150.7 (2×C), 150.3 (C), 149.1 (C), 144.8 (C), 144.7 (C), 118.0 (C), 84.6 (C), 83.6 (C), 83.5 (C), 82.7 (3×C), 82.6 (C), 76.3 (CH), 73.0 (CH), 71.4 (CH), 67.2 (CH), 64.0 ($CH_2$), 51.4 (CH), 28.1 ($CH_3$), 27.8 (2×$CH_3$), 27.7 ($CH_3$), 27.6 (3×$CH_3$). MS-ESI+ for $C_{45}H_{72}N_5O_{19}^+$, $(M+H)^+$, Calcd. 986.4817. found 986.4818. Anal. calcd. for $C_{45}H_{71}N_5O_{19}H_2O$ 54.39; C, 7.39; H, 6.34; N. found 54.66; C, 7.17; H, 7.05; N. A second fraction was obtained as a yellow foam (2.68 g) which by $^1$H NMR was a product with six Boc groups present (3a, 3b or 3c). A small amount was crystallized from EtOAc-hexanes to give colorless crystals. $[\alpha]_D^{20}$ −47.6 (c, 1.17, $CHCl_3$). $^1$H NMR (500 MHz, $CDCl_3$): δ 11.10 (br s, exchanged $D_2O$, 1H), 5.58 (t, J=1.8 Hz, 1H), 5.17 (d, J=3.4 Hz, 1H), 4.97 (t, J=3.9 Hz, 1H), 4.62 (s, exchanged $D_2O$, 1H), 4.16 (dd, J=11.3, 5.9 Hz, 1H), 4.12 (dd, J=11.3, 6.4 Hz, 1H), 3.95 (dt, J=6.1, 1.1 Hz, 1H), 3.76 (m, 1H), 1.51, 1.50, 1.49, 1.48, 1.46 (5s, 54H). $^{13}$C NMR (125.7 MHz, $CDCl_3$): δ 156.6 (C), 153.0 (C), 152.9 (C), 151.9 (C), 150.6 (C), 149.4 (2×C), 136.2 (C), 131.8 (C), 116.9 (C), 85.0 (2×C), 83.3 (C), 82.8 (C), 82.49 (C), 82.46 (C), 73.3 (CH), 71.5 (CH), 67.2 (CH), 64.5 ($CH_2$), 51.3 (CH), 28.0, 27.72, 27.68, 27.6 (4×$CH_3$). MS-ESI+ for $C_{40}H_{64}N_5O_{17}^+$, $(M+H)^+$ calcd. 886.4287. found 886.4289.

C. Preparation of Compound 4a, 4b or 4c

Step 1—The first fraction from B above containing mainly compounds 2a or 2b (1.46 g, 1.481 mmol) was dissolved in MeOH (29 mL) and sodium methoxide in MeOH (1M, 8.14 mL, 8.14 mmol) added. After leaving at ambient temperature for 20 h the solution was neutralized with Dowex 50WX8 ($H^+$) resin then the solids filtered off and the solvent evaporated.

Step 2—The second fraction from B above containing mainly 3a, 3b or 3c (2.68 g, 3.02 mmol) was dissolved in MeOH (54 mL) and sodium methoxide in MeOH (1M, 12.10 mL, 12.10 mmol) added. After leaving at ambient temperature for 20 h the solution was neutralized with Dowex 50WX8 ($H^+$) resin then the solids filtered off and the solvent evaporated.

The products from step 1 and step 2 above were combined and chromatographed on silica gel (gradient of 0 to 15% MeOH in $CHCl_3$) to give 4a, 4b or 4c as a cream colored solid (1.97 g). $^1$H NMR (500 MHz, DMSO $d_6$): δ 12.67 (br s, exchanged $D_2O$, 1H), 5.48 (d, J=5.2 Hz, exchanged $D_2O$, 1H), 5.43 (t, J=~1.9 Hz, after $D_2O$ exchange became a d, J=1.9 Hz, 1H), 5.00 (br s, exchanged $D_2O$, 1H), 4.62 (d, J=5.7 Hz, exchanged $D_2O$, 1H), 4.27 (d, J=6.0 Hz, exchanged $D_2O$, 1H), 3.89 (dt, J=5.2, 3.8 Hz, after $D_2O$ became a t, J=3.9 Hz, 1H), 3.62 (dd, J=6.0, 3.7 Hz, after $D_2O$ exchange became a d, J=3.7 Hz, 1H), 3.52-3.39 (m, 4H), 1.42 (s, 9H), 1.41 (s, 18H). $^{13}$C NMR (125.7 MHz, DMSO $d_6$): δ 157.9 (C), 151.1, (C), 149.8 (2×C), 134.6 (C), 131.4 (C), 118.8 (C), 83.5 (2×C), 81.3 (C), 78.2 (CH), 76.5 (CH), 68.1 (CH), 66.8 (CH), 60.6 ($CH_2$), 54.4 (CH), 27.9 ($CH_3$), 27.6 (2×$CH_3$). MS-ESI+ for $C_{25}H_{40}N_5O_{11}^+$, $(M+H)^+$ calcd. 586.2719. found 586.2717.

D. Preparation of Compound 5a, 5b or 5c

Compound 4a, 4b or 4c (992 mg, 1.69 mmol) was dissolved in anhydrous pyridine and concentrated. The residue was dissolved in anhydrous $CH_2Cl_2$ (10 mL) and pyridine (5 mL) under a nitrogen atmosphere and the solution was cooled to −42° C. in an acetonitrile/dry ice bath. Methyl dichlorophosphate (187 µL, 1.86 mmol) was added dropwise and the mixture was stirred for 2 h 20 min. Water (10 mL) was added to the cold solution which was then removed from the cold bath and diluted with ethyl acetate (50 mL) and saturated NaCl solution (30 mL). The organic portion was separated and washed with saturated NaCl solution. The combined aqueous portions were extracted twice further with ethyl acetate and the combined organic portions were dried over $MgSO_4$ and concentrated. Purification by silica gel flash column chromatography (eluting with 2-20% methanol in ethyl acetate) gave the cyclic methyl phosphate 5a, 5b or 5c (731 mg, 65%). $^1H$ NMR (500 MHz, $CDCl_3$,): δ 11.72 (bs, exchanged $D_2O$, 1H), 5.63 (t, J=1.8 Hz, 1H), 5.41 (s, exchanged $D_2O$, 1H), 4.95 (d, J=3.2 Hz, 1H), 4.70 (dt, J=12.4, 1.8 Hz, 1H), 4.42 (dd, J=22.1, 12.1 Hz, 1H). 4.15 (q, J=3.7 Hz, 1H), 3.82 (s, 1H), 3.75 (s, 1H), 3.58 (d, J=11.7 Hz, 3H), 2.10 (bs, exchanged $D_{20}$, 1H+$H_2O$), 1.50 (s, 9H), 1.46 (s, 18H). $^{13}C$ NMR (125.7 MHz, $CDCl_3$, centre line δ 77.0): δ 157.5 (C), 151.2 (C), 149.6 (2×C), 134.5 (C), 132.3 (C), 117.6 (C), 84.7 (2×C), 82.8 (C), 77.3 (CH), 74.8 (d, J=4.1 Hz, CH), 69.7 ($CH_2$), 68.8 (d, J=4.1 Hz, CH), 68.6 (d, J=5.9 Hz, CH), 56.0 (d, J=7.4 Hz, $CH_3$), 51.8 (CH), 28.1 ($CH_3$), 27.8 ($CH_3$). MS-ESI+ for $C_{26}H_{40}N_5NaO_{13}P^+$ $(M+Na)^+$, calcd. 684.2252. found 684.2251.

E. Preparation of Compound 6a, 6b or 6c

Compound 5a, 5b or 5c (223 mg, 0.34 mmol) was dissolved in anhydrous $CH_2Cl_2$ (7 mL) under a nitrogen atmosphere. Anhydrous DMSO (104 µL, 1.46 mmol) was added and the solution was cooled to −78° C. Trifluoroacetic anhydride (104 µL, 0.74 mmol) was added dropwise and the mixture was stirred for 40 min. N,N-diisopropylethylamine (513 µL, 2.94 mmol) was added and the stirring was continued for 50 min at −78° C. Saturated NaCl solution (20 mL) was added and the mixture removed from the cold bath and diluted with $CH_2Cl_2$ (30 mL). Glacial acetic acid (170 µL, 8.75 mmol) was added and the mixture was stirred for 10 min. The layers were separated and the aqueous phase was washed with $CH_2Cl_2$ (10 mL). The combined organic phases were washed with 5% aqueous HCl, 3:1 saturated NaCl solution:10% $NaHCO_3$ solution and saturated NaCl solution successively, dried over $MgSO_4$, and concentrated to give compound 6a, 6b or 6c (228 mg, quant.) of suitable purity for further use. $^1H$ NMR (500 MHz, $CDCl_3$): δ 5.86 (m, 1 H), 5.07 (m, 1 H), 4.70-4.64 (m, 2 H), 4.49-4.40 (m, 1 H), 4.27 (m, 1 H), 3.56, m, 4 H), 1.49 (s, 9 H), 1.46 (s, 18 H) ppm. $^{13}C$ NMR (500 MHz, $CDCl_3$): δ 157.5 (C), 151.1 (C), 150.6 (2 C), 134.6 (C), 132.7 (C), 116.6 (C), 92.0 (C), 84.6 (2 C), 83.6 (C), 78.0 (CH), 76.0 (CH), 70.4 ($CH_2$), 67.9 (CH), 56.2 ($CH_3$) δ6.0 (CH), 28.2 (3$CH_3$), 26.8 (6 $CH_3$) ppm. $^{31}P$ NMR (500 MHz, $CDCl_3$): δ−6.3 ppm.

F. Preparation of compound 7: (4aR,5aR,11aR, 12aS)-1,3,2-Dioxaphosphorino[4',5':5,6]pyrano[3,2-g]pteridin-10(4H)-one,8-amino-4-a,5a,6,9,11,11a,12, 12a-octahydro-2,12,12-trihydroxy-2-oxide Compound 6a, 6b or 6c (10 mg, 14.8 µmol was dissolved in dry acetonitrile (0.2 mL) and cooled to 0° C. Bromotrimethylsilane (19.2 µL, 148 µmol) was added dropwise and the mixture was allowed to warm to ambient temperature and stirred for 5 h during which time a precipitate formed. $HCl_{(aq)}$ (10 µl, 37%) was added and the mixture was stirred for a further 15 min. The mixture was centrifuged for 15 min (3000 g) and the resulting precipitate collected. Acetonitrile (0.5 mL) was added and the mixture was centrifuged for a further 15 min. The acetonitrile wash and centrifugation was repeated a further two times and the resulting solid was dried under high vacuum to give compound 7 (4 mg, 75%). $^1H$ NMR (500 MHz, $D_2O$): δ 5.22 (d, J=1.6 Hz, 1H), 4.34 (dt, J=13, 1.6 Hz, 1H), 4.29-4.27 (m, 1H), 4.24-4.18 (m, 1H), 3.94 (br m, 1H), 3.44 (t, J=1.4 Hz, 1H). $^{31}P$ NMR (500 MHz, $D_2O$): δ −4.8 MS-ESI+ for $C_{10}H_{15}N_5O_8P^+$, $(M+H)^+$calcd. 364.0653. found 364.0652.

Example 2

Comparison of Precursor Z (cPMP) Prepared Synthetically to that Prepared from *E. Coli* in the In vitro Synthesis of Moco In vitro synthesis of Moco was compared using samples of synthetic precursor Z (cPMP) and cPMP purified from *E. coli*. Moco synthesis also involved the use of the purified components *E. coli* MPT synthase, gephyrin, molybdate, ATP, and apo-sulfite oxidase. See U.S. Pat. No. 7,504,095 and "Biosynthesis and molecular biology of the molybdenum cofactor (Moco)" in Metal Ions in Biological Systems, Mendel, Ralf R. and Schwarz, Gunter, Informa Plc, 2002, Vol. 39, pages 317-68. The assay is based on the conversion of cPMP into MPT, the subsequent molybdate insertion using recombinant gephyrin and ATP, and finally the reconstitution of human apo-sulfite oxidase.

As shown in FIG. 1, Moco synthesis from synthetic cPMP was confirmed, and no differences in Moco conversion were found in comparison to *E. coli* purified cPMP.

Example 3

Comparison of Precursor Z (cPMP) Prepared Synthetically to that Prepared from *E. coli* in the In vitro Synthesis of MPT In vitro synthesis of MPT was compared using samples of synthetic precursor Z (cPMP) and cPMP purified from *E. coli*. MPT synthesis also involved the use of in vitro assembled MPT synthase from *E. coli*. See U.S. Pat. No. 7,504,095 and "Biosynthesis and molecular biology of the molybdenum cofactor (Moco)" in Metal Ions in Biological Systems, Mendel, Ralf R. and Schwarz, Gunter, Informa Plc, 2002, Vol. 39, pages 317-68. Three repetitions of each experiment were performed and are shown in FIGS. 2 and 3.

Figure 2:
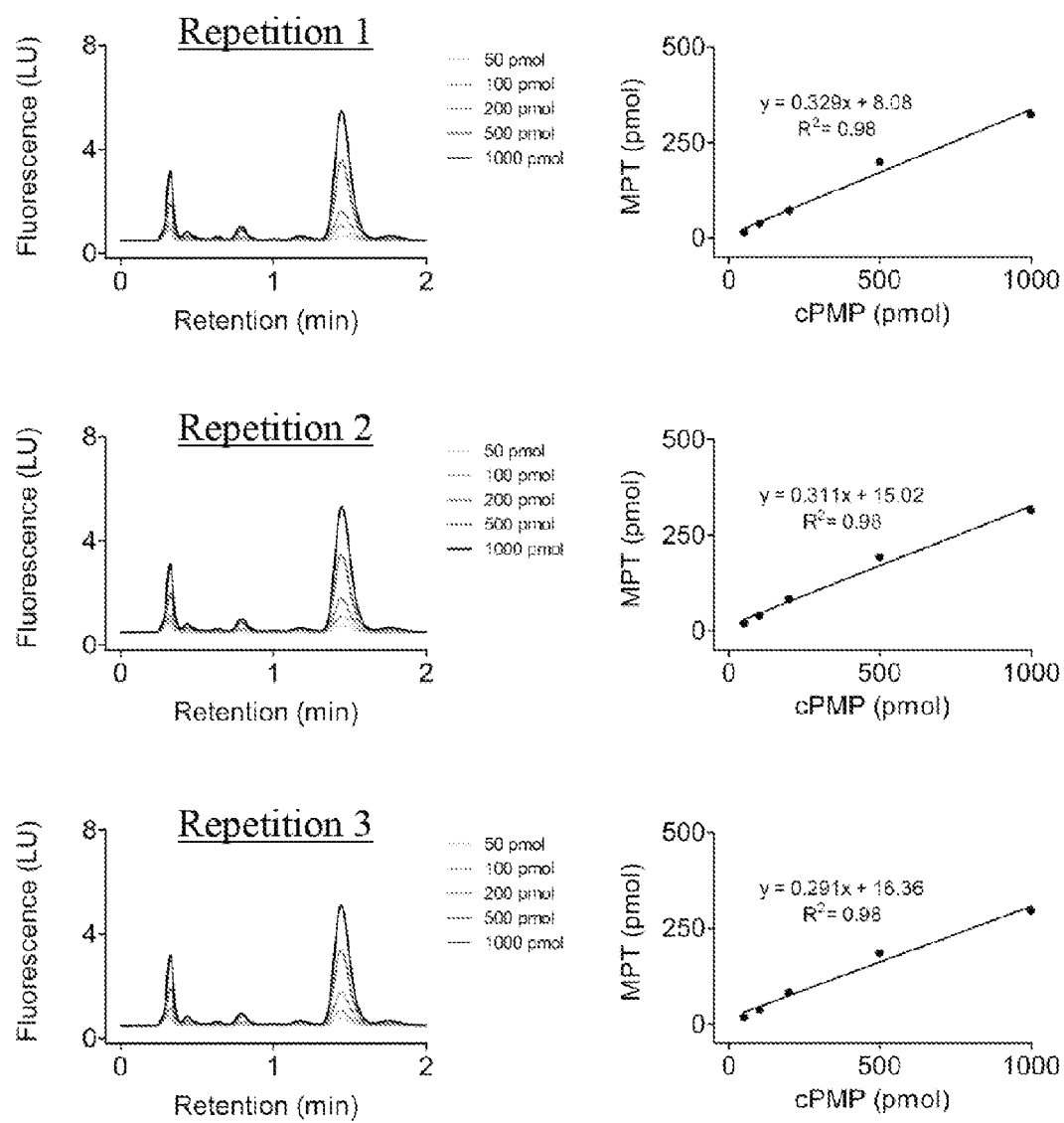
FIG. 2 provides the data from three repetitions of in vitro synthesis of MPT from synthetic precursor Z (cPMP).
Figure 3:
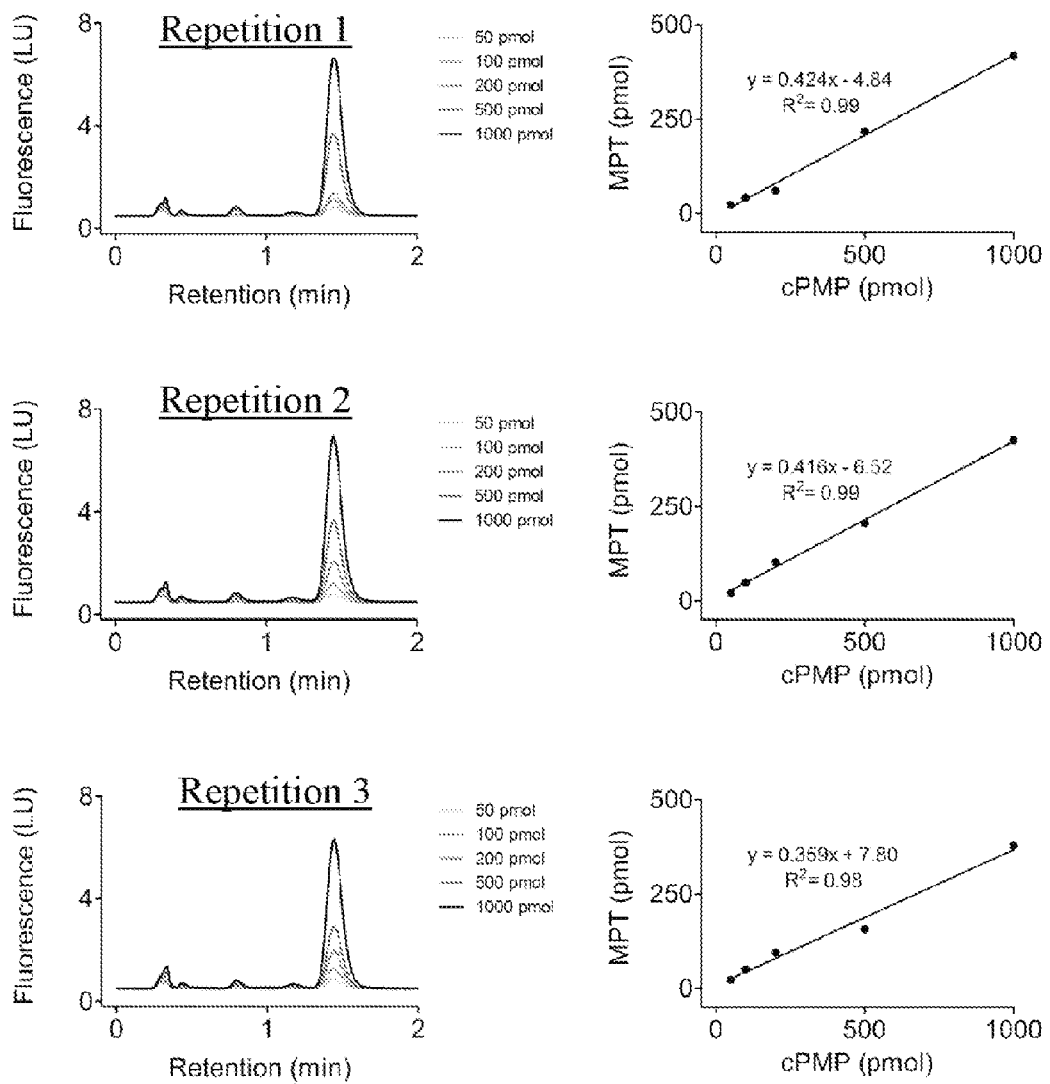
FIG. 3 provides the data from three repetitions of in vitro synthesis of MPT from precursor Z (cPMP) prepared and purified from a fermentation process using *E. coli*.

As shown in FIGS. 2 and 3, MPT synthesis from synthetic cPMP confirmed, and no apparent differences in MPT conversion were found when compared to *E. coli* purified cPMP. A linear conversion of cPMP into MPT is seen in all samples confirming the identity of synthetic cPMP (see FIG. 2). Slight differences between the repetitions are believed to be due to an inaccurate concentration determination of synthetic cPMP given the presence of interfering chromophores.

Example 4
Preparation of Precursor Z (cPMP)
A. Preparation of Starting Materials
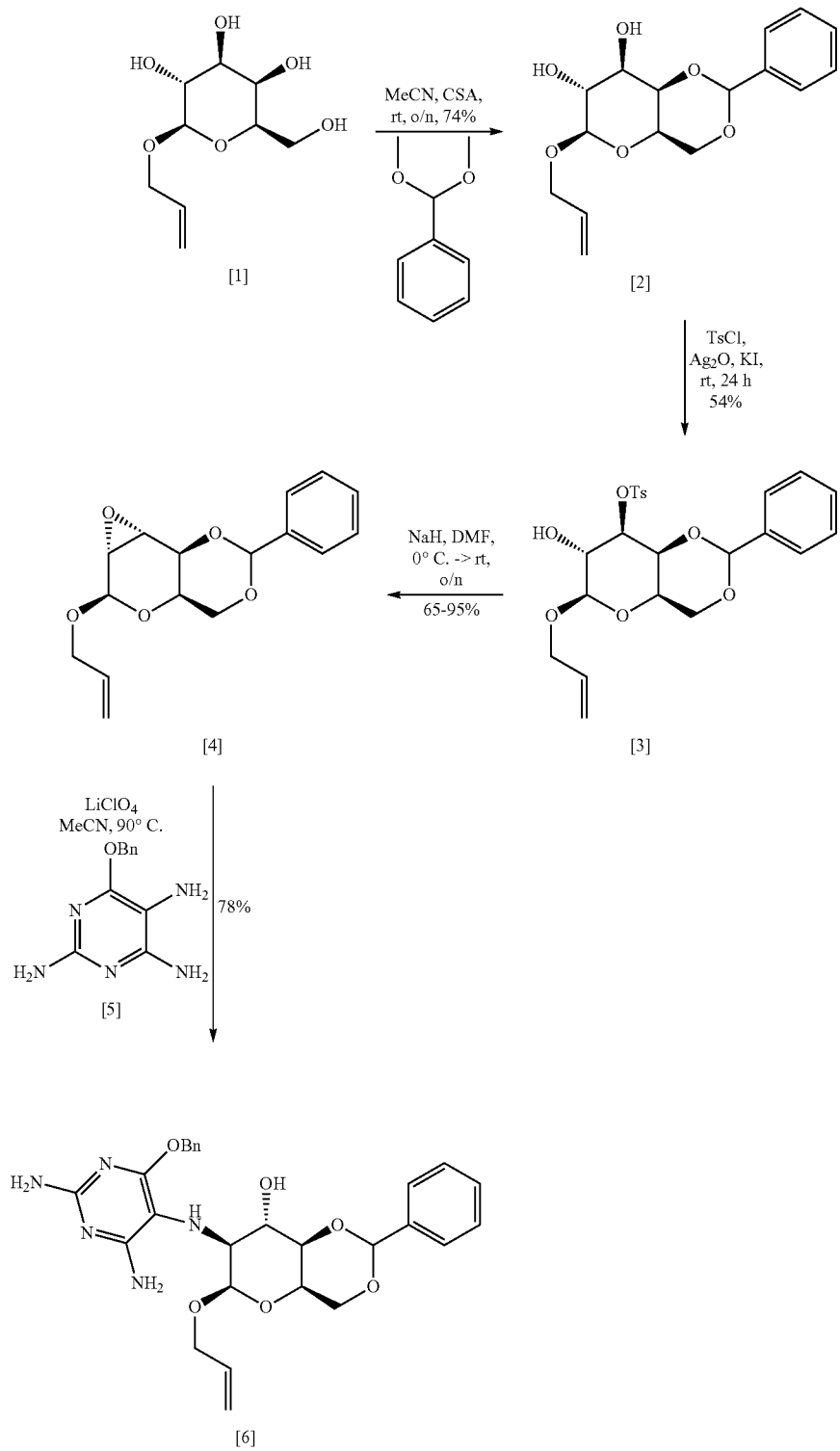
Scheme 22.

B. Introduction of the protected Phosphate
Scheme 23.
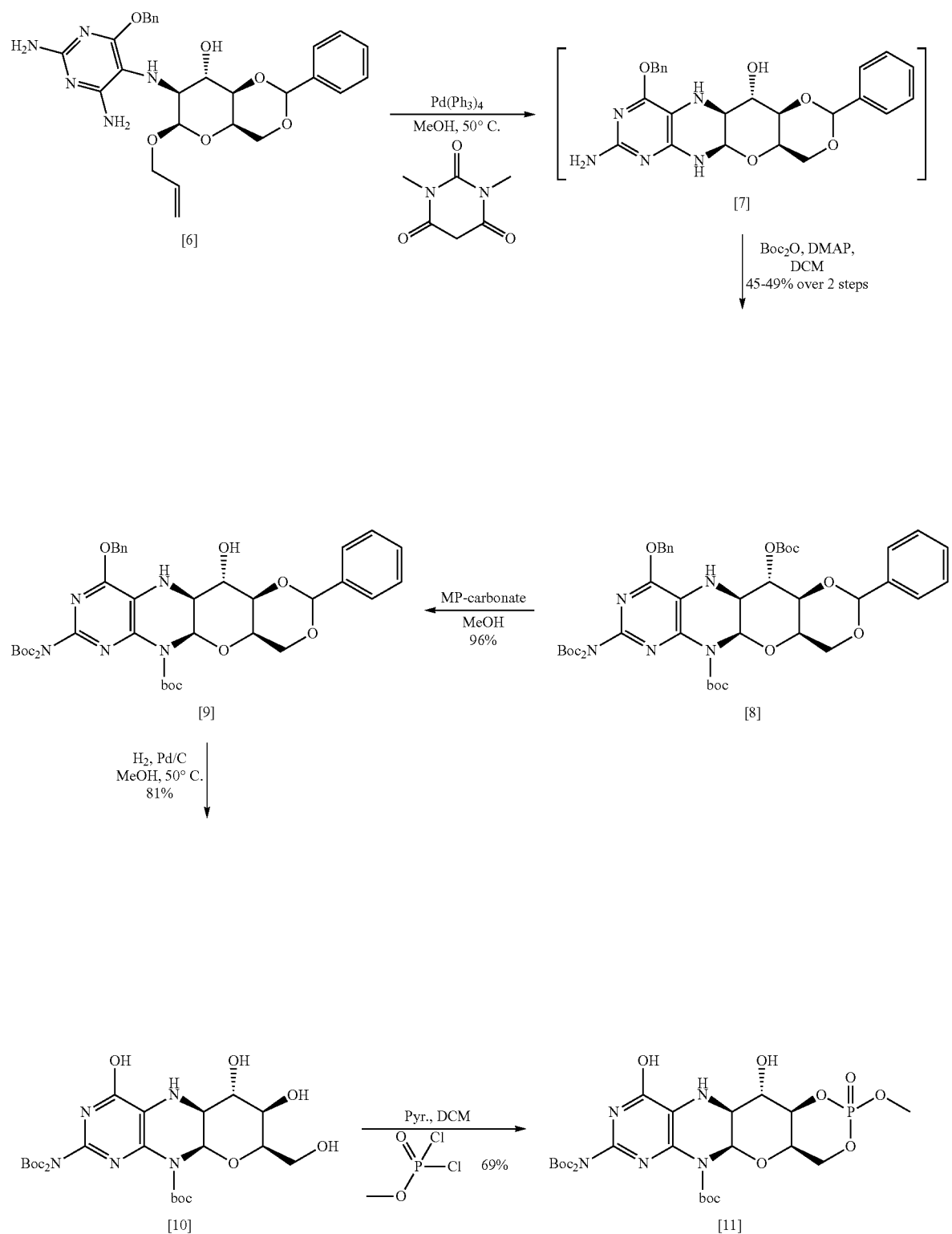
The formation of the cyclic phosphate using intermediate [10] (630 mg) gave the desired product [11] as a 1:1 mixture of diastereoisomers (494 mg, 69%).

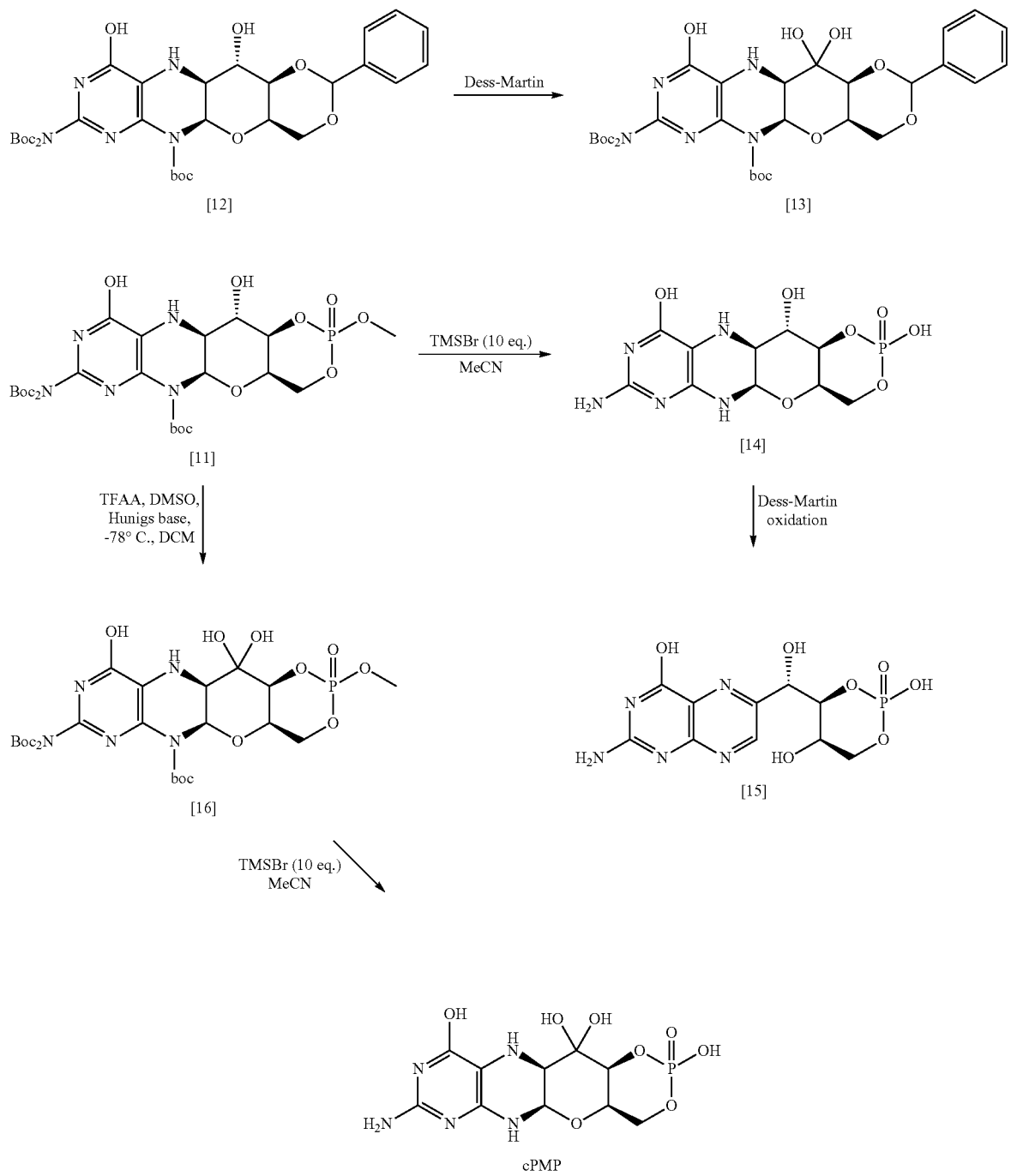

Scheme 24.

C. Oxidation and Overall Deprotection of the Molecule

Oxidation of the secondary alcohol to the gem-diol did prove successful on intermediate [12], but the oxidized product [13] did show significant instability and could not be purified. For this reason, deprotection of the phosphate was attempted before the oxidation. However, the reaction of intermediate [11] with TMSBr led to complete deprotection of the molecule giving intermediate [14]. An attempt to oxidize the alcohol to the gem-diol using Dess-Martin periodinane gave the aromatized pteridine [15].

Oxidation of intermediate [11] with Dess-Martin periodinane gave a mixture of starting material, oxidized product and several by-products. Finally, intermediate [11] was oxidized using the method described Example 1. Upon treatment, only partial oxidation was observed, leaving a 2:1 mixture of [11]/[16]. The crude mixture was submitted to the final deprotection. An off white solid was obtained and analyzed by $^1$H-NMR and HPLC-MS. These analyses suggest that cPMP has been produced along with the deprotected precursor [11].

Because the analytical HPLC conditions gave a good separation of cPMP from the major impurities, this method will be repeated on a prep-HPLC in order to isolate the final material.

What is claimed is:

1. A process for preparing a compound of formula (I):

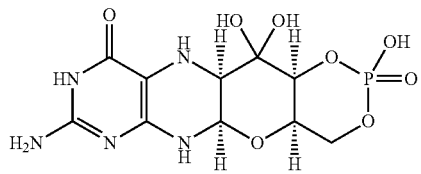 [SMILES: Nc1nc2c(c(=O)[nH]1)N[C@@H]1[C@H](N2)O[C@@H]2COP(=O)(O)O[C@@H]2C1(O)O]

or a pharmaceutically acceptable salt thereof, the process comprising:

(a) reacting a compound of formula (II):

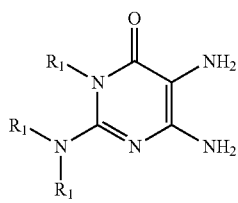

wherein:
each $R_1$ is independently H or a protecting group,
with a compound of formula (III):

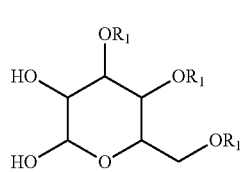

to produce a compound of formula (IV):

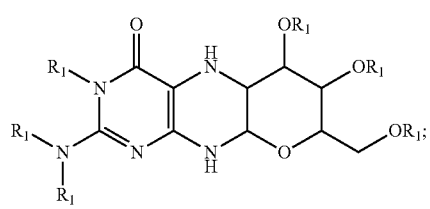

(b) selectively protecting the compound of formula (IV) to prepare a compound of formula (V):

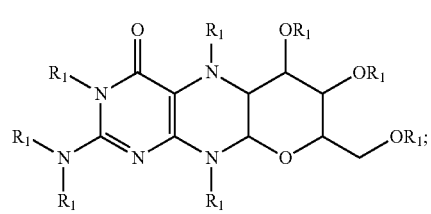

(c) phosphorylating the compound of formula (V) to prepare a compound of formula (VI):

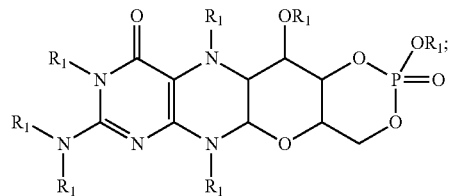

(d) oxidizing the compound of formula (VI) to prepare a compound of formula (VII):

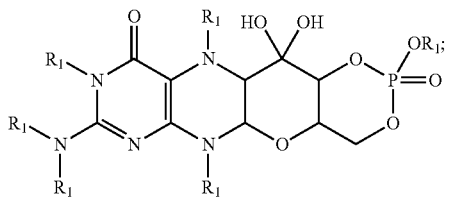

and (e) deprotecting the compound of formula (VII) to prepare the compound of formula (I).

2. The process of claim 1, wherein the pharmaceutically acceptable salt is an HCl salt.

3. The process of claim 1, wherein the compound of formula (II) is:

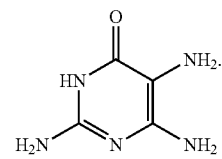

4. The process of claim 1, wherein the compound of formula (III) is a protected or unprotected galactose, mannose, glucose, or gulose.

5. The process of claim 1, wherein the compound of formula (III) is:

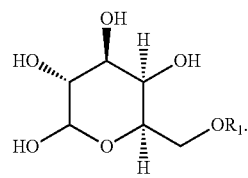

6. The process of claim 1, wherein two adjacent $R_1$ groups come together to form an isopropylidine acetal or benzylidine acetal moiety.

7. The process of claim 1, wherein step (a) comprises reacting the compound of formula (II) and the compound of formula (III) in the presence of a hydrazine.

8. The process of claim 7, wherein the hydrazine is selected from the group consisting of phenylhydrazines and alkylhydrazines.

9. The process of claim 8, wherein the hydrazine is phenylhydrazine.

10. The process of claim 1, wherein the phosphorylation of step (c) comprises reacting the compound of formula (V) with a P(V) phosphorylating agent.

11. The process of claim 10, wherein the P(V) phosphorylating agent is selected from the group consisting of: $POCl_3$; $H_3PO_4$; $PO(OBn)_xCl_{3-x}$; $Cl_3CCH_2OP(O)Cl_2$; and $(BnO)_2P(O)OP(O)(OBn)_2$.

12. The process of claim 10, wherein the P(V) phosphorylating agent is $POCl_3$.

13. The process of claim 1, wherein the phosphorylation of step (c) comprises reacting the compound of formula (V) with a P(III) phosphitylating agent.

14. The process of claim 13, wherein the P(III) phosphitylating agent is selected from the group consisting of: $P(OCH_2CH_2CN)_2Cl$; $P(OCH_2CH_2CN)(NPr_2\text{-}i)Cl$; and cyanoethyl-O—$P[N(i\text{-}Pr)_2]_2$.

15. The process of claim 13, wherein step (c) further comprises oxidizing the resulting phosphite to prepare the phosphate of compound (VI).

16. The process of claim 1, wherein step (d) comprises reacting the compound of formula (VI) with an oxidizing agent selected from the group consisting of: $RuO_4$; Dess-Martin; DMSO/triflic anhydride; and PDC.

17. The process of claim 1, wherein the deprotection of the compound of formula (VII) is performed under anaerobic conditions.

18. The process of claim 1, wherein the compound of formula (IV) is:

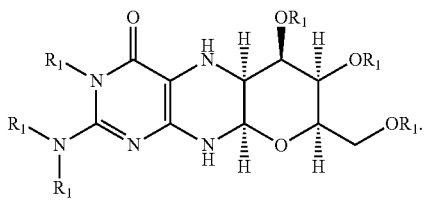

19. The process of claim 1, wherein the compound of formula (V) is:

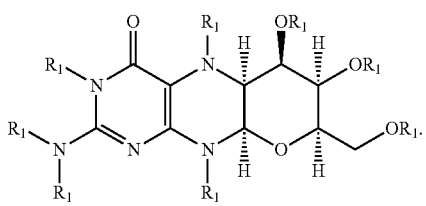

20. The process of claim 1, wherein the compound formula (VI) is:

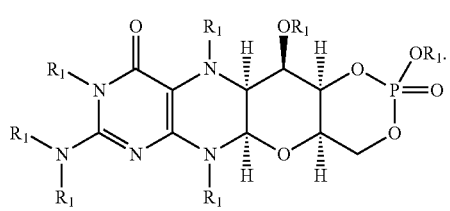

21. The process of claim 1, wherein the compound of formula (VII) is:

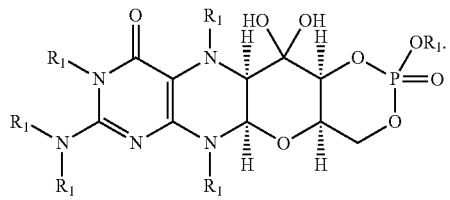

22. The process of claim 1, wherein the process further comprises formulating the compound of formula (I) as a pharmaceutical composition.

23. A compound of formula (IV):

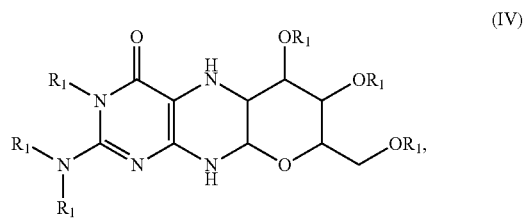

or a pharmaceutically acceptable salt form thereof, wherein:

each $R_1$ is independently H or a protecting group.

24. A compound of formula (V):

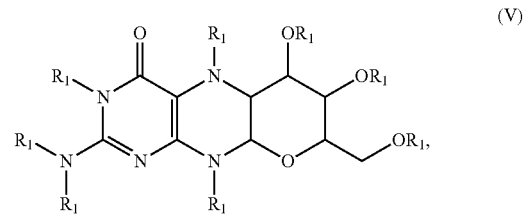

or a pharmaceutically acceptable salt form thereof, wherein:

each $R_1$ is independently H or a protecting group.

25. A compound of formula (VI):

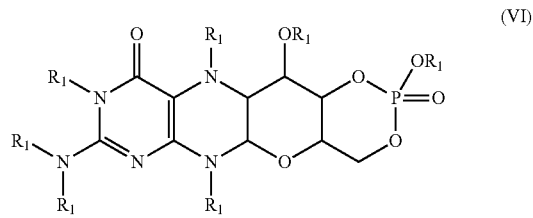

or a pharmaceutically acceptable salt form thereof, wherein:

each $R_1$ is independently H or a protecting group, and at least $R_1$ is a protecting group.

26. A compound of formula (VII):

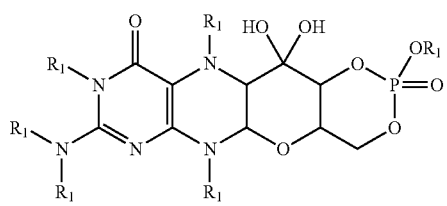

or a pharmaceutically acceptable salt form thereof, wherein:
each $R_1$ is independently H or a protecting group; and at least one $R_1$ is a protecting group.

27. A process for preparing a compound of formula (XIII):

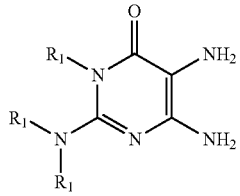

or a pharmaceutically acceptable salt form thereof, the process comprising:
(a) reacting a compound of formula (II):

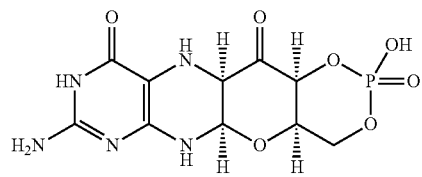

with a compound of formula (III):

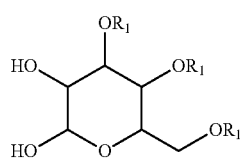

to produce a compound of formula (IV):

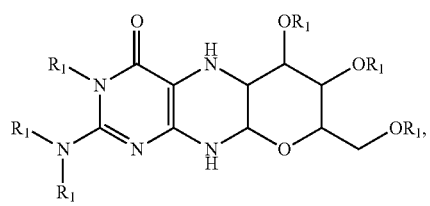

wherein:
each $R_1$ is independently H or a protecting group;
(b) selectively protecting the compound of formula (IV) to prepare a compound of formula (V):

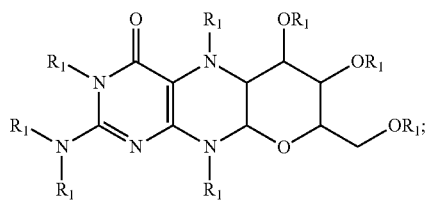

(c) phosphorylating the compound of formula (V) to prepare a compound of formula (VI):

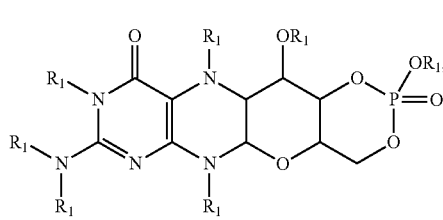

(d) oxidizing the compound of formula (VI) to prepare a compound of formula (XIV):

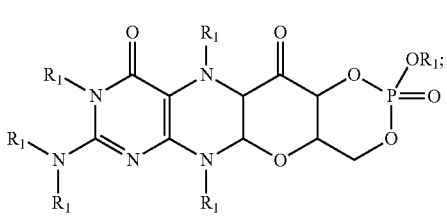

and (e) deprotecting the compound of formula (XIV) to prepare the compound of formula (XIII).

28. The process of claim 27, wherein the pharmaceutically acceptable salt is an HCl salt.

29. The process of claim 27, wherein the compound of formula (II) is:

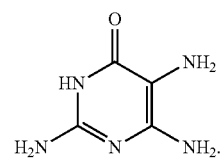

30. The process of claim 27, wherein the compound of formula (III) is a protected or unprotected galactose, mannose, glucose, or gulose.

31. The process of claim 27, wherein the compound of formula (III) is:

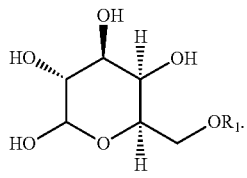

32. The process of claim 27, wherein two adjacent $R_1$ groups come together to form an isopropylidine acetal or benzylidine acetal moiety.

33. The process of claim 27, wherein step (a) comprises reacting the compound of formula (II) and the compound of formula (III) in the presence of a hydrazine.

34. The process of claim 33, wherein the hydrazine is selected from the group consisting of phenylhydrazines and alkylhdrazines.

35. The process of claim 34, wherein the hydrazine is phenylhydrazine.

36. The process of claim 27, wherein the phosphorylation of step (c) comprises reacting the compound of formula (V) with a P(V) phosphorylating agent.

37. The process of claim 36, wherein the P(V) phosphorylating agent is selected from the group consisting of: $POCl_3$; $H_3PO_4$; $PO(OBn)_xCl_{3-x}$; $Cl_3CCH_2OP(O)Cl_2$; and $(BnO)_2P(O)OP(O)(OBn)_2$.

38. The process of claim 37, wherein the P(V) phosphorylating agent is $POCl_3$.

39. The process of claim 27, wherein the phosphorylation of step (c) comprises reacting the compound of formula (V) with a P(III) phosphitylating agent.

40. The process of claim 39, wherein the P(III) phosphitylating agent is selected from the group consisting of: $P(OCH_2CH_2CN)_2Cl$; $P(OCH_2CH_2CN)(NPr_2\text{-}i)Cl$; and cyanoethyl-O—$P[N(i\text{-}Pr)_2]_2$.

41. The process of claim 39, wherein step (c) further comprises oxidizing the resulting phosphite to prepare the phosphate of compound (VI).

42. The process of claim 27, wherein step (d) comprises reacting the compound of formula (VI) with an oxidizing agent selected from the group consisting of: $RuO_4$; Dess-Martin; DMSO/triflic anhydride; and PDC.

43. The process of claim 27, wherein the deprotection of the compound of formula (XIV) is performed under anaerobic conditions.

44. The process of claim 27, wherein the compound of formula (IV) is:

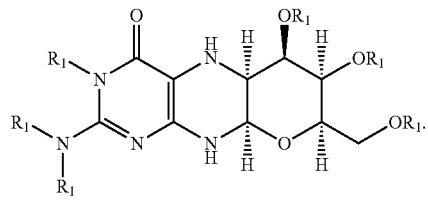

45. The process of claim 27, wherein the compound of formula (V) is:

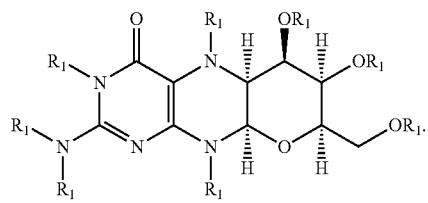

46. The process of claim 27, wherein the compound formula (VI) is:

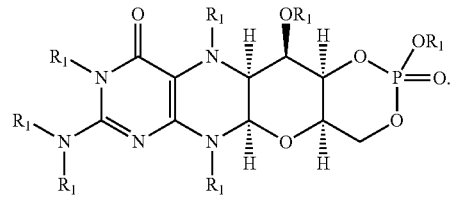

47. The process of claim 27, wherein the compound of formula (XIV) is:

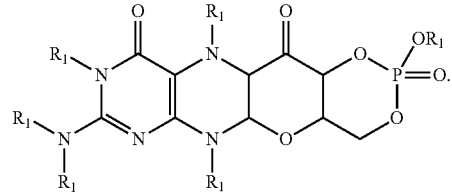

48. The process of claim 27, wherein the process further comprises formulating the compound of formula (XIII) as a pharmaceutical composition.

* * * * *